United States Patent
Brochu et al.

(10) Patent No.: US 9,340,539 B2
(45) Date of Patent: May 17, 2016

(54) HEPATITIS C INHIBITOR COMPOUNDS

(75) Inventors: Christian Brochu, Blainville (CA); Chantal Grand-Maitre, Boisbriand (CA); Lee Fader, New Milford, CT (US); Cyrille Kuhn, Ridgefield, CT (US); Megan Bertrand-Laperle, Laval (CA); Marc Pesant, St. Colomban (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/240,641

(22) PCT Filed: Aug. 22, 2012

(86) PCT No.: PCT/CA2012/050578
§ 371 (c)(1),
(2), (4) Date: Jun. 9, 2014

(87) PCT Pub. No.: WO2013/026163
PCT Pub. Date: Feb. 28, 2013

(65) Prior Publication Data
US 2014/0343077 A1    Nov. 20, 2014

Related U.S. Application Data

(60) Provisional application No. 61/526,955, filed on Aug. 24, 2011.

(51) Int. Cl.

| | |
|---|---|
| *C07D 487/04* | (2006.01) |
| *A61K 45/06* | (2006.01) |
| *A61K 31/403* | (2006.01) |
| *C07D 471/04* | (2006.01) |
| *C07D 403/12* | (2006.01) |
| *C07D 401/14* | (2006.01) |
| *C07D 405/14* | (2006.01) |
| *C07D 413/14* | (2006.01) |
| *C07D 401/12* | (2006.01) |
| *C07D 403/06* | (2006.01) |
| *C07D 403/14* | (2006.01) |
| *C07D 409/12* | (2006.01) |
| *C07D 409/14* | (2006.01) |
| *C07D 413/04* | (2006.01) |
| *C07D 417/14* | (2006.01) |
| *C07D 491/107* | (2006.01) |
| *A61K 31/4155* | (2006.01) |
| *A61K 31/4178* | (2006.01) |
| *A61K 31/4196* | (2006.01) |
| *A61K 31/433* | (2006.01) |
| *A61K 31/437* | (2006.01) |
| *A61K 31/4439* | (2006.01) |
| *A61K 31/497* | (2006.01) |
| *C07D 405/12* | (2006.01) |

(52) U.S. Cl.
CPC ............ *C07D 471/04* (2013.01); *A61K 31/403* (2013.01); *A61K 31/4155* (2013.01); *A61K 31/4178* (2013.01); *A61K 31/4196* (2013.01); *A61K 31/433* (2013.01); *A61K 31/437* (2013.01); *A61K 31/4439* (2013.01); *A61K 31/497* (2013.01); *A61K 45/06* (2013.01); *C07D 401/12* (2013.01); *C07D 401/14* (2013.01); *C07D 403/06* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01); *C07D 413/04* (2013.01); *C07D 413/14* (2013.01); *C07D 417/14* (2013.01); *C07D 487/04* (2013.01); *C07D 491/107* (2013.01)

(58) Field of Classification Search
CPC ..... C07D 487/04; A61K 31/403; A61K 45/06
See application file for complete search history.

(56) References Cited

U.S. PATENT DOCUMENTS

2006/0276496 A1* 12/2006 Goldberg ............. C07D 471/02
514/291

OTHER PUBLICATIONS

International Search Report, form PCT/ISA/210, and Written Opinion, form PCT/ISA/237, for corresponding application PCT/CA2012/050578, date of mailing Nov. 8, 2012.

*Primary Examiner* — Erich A Lesser
(74) *Attorney, Agent, or Firm* — Michael P. Morris; Edward S. Lazer

(57) ABSTRACT

A compound of formula (I) useful for the treatment or prevention of hepatitis C viral infection, (Formula (I)) wherein: $X^1$ and $X^2$ are each independently $CR^B$ or N; $R^B$ is H, $(C_{1-6})$alkyl, $(C_{1-6})$haloalkyl, halo. —O—$(C_{1-6})$alkyl, $NH_2$, $NH(C_{1-6})$alkyl or $N((C_{1-6})alkyl)_2$; $R^1$ and $R^2$ are each independently $(C_{1-6})$alkyl optionally mono- or di-substituted with —O—$(C_{1-6})$alkyl, $NH_2$, $NH(C_{1-6})$alkyl or $N((C_{1-6})alkyl)_2$; or $R^1$ and $R^2$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl; $R^A$ is —C(=O)N($R^3$)($R^4$), —C(=O)O($R^4$), heterocyclyl or heteroaryl, wherein each said heterocyclyl and heteroaryl is optionally substituted 1 to 3 times with $R^{41}$; $R^5$ and $R^6$ are each independently H or $(C_{1-6})$alkyl optionally mono- or di-substituted with —O—$(C_{1-6})$alkyl, $NH_2$, $NH(C_{1-6})$alkyl or $N((C_{1-6})alkyl)_2$; or $R^5$ and $R^6$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl; and n is 0, 1 or 2.

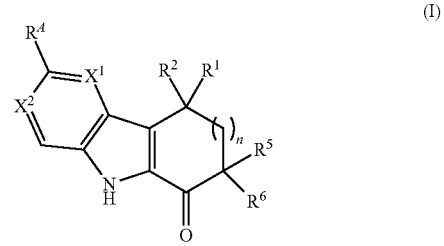

(I)

13 Claims, No Drawings

HEPATITIS C INHIBITOR COMPOUNDS

RELATED APPLICATION

This application claims benefit of U.S. Ser. No. 61/526,955 filed Aug. 24, 2011, which is herein incorporated by reference.

FIELD OF THE INVENTION

This invention relates to tetrahydro-carbazolone analogs and their use in inhibiting entry of hepatitis C virus (HCV) into a cell, pharmaceutical compositions containing the same, and methods of using the same as agents for treatment of HCV infection.

BACKGROUND OF THE INVENTION

It is estimated that at least 170 million persons worldwide are infected with the hepatitis C virus. Acute HCV infection progresses to chronic infection in a high number of cases, and, in some infected individuals, chronic infection leads to serious liver diseases such as cirrhosis and hepatocellular carcinoma.

WO 2009/103022 discloses derivatives of substituted fused ring cycloindoles which inhibit entry of a hepatitis C virus into a cell. US 2010-0190773 discloses heterocyclic compounds for use as inhibitors of mitogen-activated protein kinase-activated protein kinase-2.

SUMMARY OF THE INVENTION

This invention provides novel compounds which inhibit entry of hepatitis C virus into a cell as measured by a HCV pseudo-particle/luciferase assay.

Further objects of this invention arise for the one skilled in the art from the following description and the examples.

Representative embodiments of the compound aspect of the invention are described below, while other embodiments of the compound aspect of the invention are described throughout the specification, for example under the heading "Preferred Embodiments" beginning on page 17.

Embodiment 1 provides a compound of Formula (I) or salt thereof:

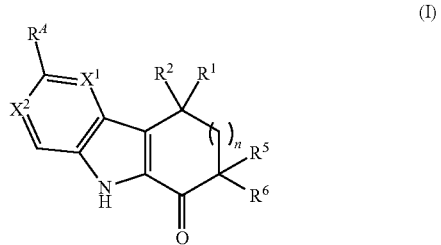

(I)

wherein:

$X^1$ and $X^2$ are each independently $CR^B$ or N;

$R^B$ is H, $(C_{1-6})$alkyl, $(C_{1-6})$haloalkyl, halo, —O—$(C_{1-6})$alkyl, $NH_2$, $NH(C_{1-6})$alkyl or $N((C_{1-6})$alkyl$)_2$;

$R^1$ and $R^2$ are each independently $(C_{1-6})$alkyl optionally mono- or di-substituted with —O—$(C_{1-6})$alkyl, $NH_2$, $NH(C_{1-6})$alkyl or $N((C_{1-6})$alkyl$)_2$; or $R^1$ and $R^2$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl;

$R^4$ is —C(=O)N($R^3$)($R^4$), —C(=O)O($R^4$), heterocyclyl or heteroaryl, wherein each said heterocyclyl and heteroaryl is optionally substituted 1 to 3 times with $R^{41}$;

$R^3$ is H or $(C_{1-6})$alkyl optionally mono- or di-substituted with —O—$(C_{1-6})$alkyl, $NH_2$, $NH(C_{1-6})$alkyl, $N((C_{1-6})$alkyl$)_2$, —C(=O)—$(C_{1-6})$alkyl, —$SO_2NH_2$, —$SO_2$—NH$(C_{1-6})$alkyl, —$SO_2$—N$((C_{1-6})$alkyl$)_2$, —$SO_2(C_{1-6})$alkyl, —C(=O)—$NH_2$, —C(=O)—NH$(C_{1-6})$alkyl or —C(=O)—N$((C_{1-6})$alkyl$)_2$;

$R^4$ is H, $(C_{1-6})$alkyl, $(C_{3-7})$cycloalkyl, —$(C_{1-6})$alkyl-aryl, —$(C_{1-6})$alkyl-heterocyclyl, —$(C_{1-6})$alkyl-heteroaryl, aryl, heterocyclyl or heteroaryl, wherein each said alkyl, cycloalkyl, aryl, heterocyclyl and heteroaryl, either alone or in combination with another radical, is optionally substituted 1 to 3 times with $R^{41}$, or $R^3$ and $R^4$, together with the N atom to which they are attached, are linked to form a heterocyclyl or heteroaryl, wherein said heterocyclyl and heteroaryl are optionally substituted 1 to 3 times with $R^{41}$;

$R^{41}$ is each independently selected from the group consisting of halo, oxo, cyano, nitro, $R^{42}$, —C(=O)—$R^{42}$, —C(=O)O$R^{42}$, —O$R^{42}$, —S$R^{42}$, —SO$R^{42}$, —$SO_2R^{42}$, —N($R^{43}$)$R^{42}$, —C(=O)—N($R^{43}$)$R^{42}$, —N($R^{43}$)—C(=O)$R^{42}$, —O—C(=O)—N($R^{43}$)$R^{42}$ and —$SO_2$—N($R^{43}$)$R^{42}$;

$R^{42}$ is each independently selected from the group consisting of H, $(C_{1-6})$alkyl, $(C_{3-7})$cycloalkyl, —$(C_{1-6})$alkyl-aryl, —$(C_{1-6})$alkyl-heterocyclyl, —$(C_{1-6})$alkyl-heteroaryl, aryl, heterocyclyl and heteroaryl, wherein each said alkyl, cycloalkyl, aryl, heterocyclyl and heteroaryl, either alone or in combination with another radical, is optionally substituted with 1 to 3 substituents each independently selected from the group consisting of:

halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —$SO_2NH_2$, —$SO_2$—NH$(C_{1-6})$alkyl, —$SO_2$—N$((C_{1-6})$alkyl$)_2$, —$SO_2(C_{1-6})$alkyl, —C(=O)—$NH_2$, —C(=O)—NH$(C_{1-6})$alkyl, —C(=O)—N$((C_{1-6})$alkyl$)_2$, —$NH_2$, —NH$(C_{1-6})$alkyl, —N$((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl;

$R^{43}$ is H or $(C_{1-6})$alkyl;

$R^5$ and $R^6$ are each independently H or $(C_{1-6})$alkyl optionally mono- or di-substituted with —O—$(C_{1-6})$alkyl, $NH_2$, $NH(C_{1-6})$alkyl or $N((C_{1-6})$alkyl$)_2$; or $R^5$ and $R^6$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl; and n is 0, 1 or 2.

Embodiment 2 provides a compound of Formula (I), or a pharmaceutically acceptable salt thereof, wherein $X^1$ and $X^2$ are each independently $CR^B$ or N;

$R^B$ is H, $(C_{1-6})$alkyl, $(C_{1-6})$haloalkyl, halo, —O—$(C_{1-6})$alkyl, $NH_2$, $NH(C_{1-6})$alkyl or $N((C_{1-6})$alkyl$)_2$;

$R^1$ and $R^2$ are each independently $(C_{1-6})$alkyl optionally mono- or di-substituted with —O—$(C_{1-6})$alkyl, $NH_2$, $NH(C_{1-6})$alkyl or $N((C_{1-6})$alkyl$)_2$; or $R^1$ and $R^2$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl;

$R^4$ is —C(=O)N($R^3$)($R^4$);

$R^3$ is H or $(C_{1-6})$alkyl optionally mono- or di-substituted with —O—$(C_{1-6})$alkyl, $NH_2$, $NH(C_{1-6})$alkyl, $N((C_{1-6})$alkyl$)_2$, —C(=O)—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—$NH(C_{1-6})$alkyl or —C(=O)—$N((C_{1-6})$alkyl$)_2$;

$R^4$ is $(C_{3-7})$cycloalkyl, aryl, heterocyclyl or heteroaryl, wherein each said cycloalkyl, aryl, heterocyclyl and heteroaryl, either alone or in combination with another radical, is mono-substituted with —C(=O)—$R^{42}$;

$R^{42}$ is each independently selected from the group consisting of $(C_{1-6})$alkyl, $(C_{3-7})$cycloalkyl, —$(C_{1-6})$alkyl-aryl, —$(C_{1-6})$alkyl-heterocyclyl, —$(C_{1-6})$alkyl-heteroaryl, aryl and heteroaryl, wherein each said alkyl, cycloalkyl, aryl, heterocyclyl and heteroaryl, either alone or in combination with another radical, is optionally substituted with 1 to 3 substituents each independently selected from the group consisting of:

halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—$NH(C_{1-6})$alkyl, —C(=O)—$N((C_{1-6})$alkyl$)_2$, —$NH_2$, —$NH(C_{1-6})$alkyl, —$N((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl;

$R^5$ and $R^6$ are each independently H or $(C_{1-6})$alkyl optionally mono- or di-substituted with —O—$(C_{1-6})$alkyl, $NH_2$, $NH(C_{1-6})$alkyl or $N((C_{1-6})$alkyl$)_2$; or $R^5$ and $R^6$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl; and n is 0, 1 or 2.

Embodiment 3 provides a compound of embodiment 1 or 2, or a pharmaceutically acceptable salt thereof, wherein $X^1$ and $X^2$ are each independently $CR^B$ or N;

$R^B$ is H, $(C_{1-6})$alkyl, $(C_{1-6})$haloalkyl, halo, —O—$(C_{1-6})$alkyl, $NH_2$, $NH(C_{1-6})$alkyl or $N((C_{1-6})$alkyl$)_2$.

Embodiment 4 provides a compound of embodiment 1, 2 or 3, or a pharmaceutically acceptable salt thereof, wherein $X^1$ and $X^2$ are each independently CH or N.

Embodiment 5 provides a compound of any one of embodiments 1-4 or a pharmaceutically acceptable salt thereof, wherein $X^1$ and $X^2$ are CH.

Embodiment 6 provides a compound of any one of embodiments 1-5 or a pharmaceutically acceptable salt thereof, wherein $R^1$ and $R^2$ are each independently $(C_{1-3})$alkyl optionally mono-substituted with —O—$(C_{1-3})$alkyl, $NH_2$, $NH(C_{1-3})$alkyl or $N((C_{1-3})$alkyl$)_2$; or $R^1$ and $R^2$ and the carbon to which they are attached are linked to form a $(C_{3-7})$cycloalkyl group.

Embodiment 7 provides a compound of any one of embodiments 1-6 or a pharmaceutically acceptable salt thereof, wherein $R^1$ and $R^2$ are each independently $(C_{1-3})$alkyl optionally mono-substituted with —O—$(C_{1-3})$alkyl; or $R^1$ and $R^2$ and the carbon to which they are attached are linked to form a $(C_{3-4})$cycloalkyl group.

Embodiment 8 provides a compound of any one of embodiments 1 or 3-7, or a pharmaceutically acceptable salt thereof, wherein $R^A$ is —C(=O)$N(R^3)(R^4)$, heterocyclyl or heteroaryl, wherein each said heterocyclyl and heteroaryl is optionally substituted 1 or 2 times with $R^{41}$;

$R^{41}$ is each independently selected from the group consisting of —C(=O)—$R^{42}$ and —$N(R^{43})R^{42}$;

$R^{42}$ is each independently selected from the group consisting of $(C_{3-7})$cycloalkyl, —$(C_{1-6})$alkyl-heterocyclyl, —$(C_{1-6})$alkyl-heteroaryl, heterocyclyl and heteroaryl, wherein each said alkyl, cycloalkyl, heterocyclyl and heteroaryl, either alone or in combination with another radical, is optionally mono- or di-substituted with substituents each independently selected from the group consisting of:

halo, OH, $(C_{1-6})$haloalkyl, —O—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —$NH_2$, —$NH(C_{1-6})$alkyl, —$N((C_{1-6})$alkyl$)_2$, —NH—C(=O)$(C_{1-6})$alkyl, —C(=O)$NH_2$ and $(C_{1-6})$alkyl;

$R^{43}$ is H or $(C_{1-6})$alkyl.

Embodiment 9 provides a compound of any one of embodiments 1 and 3-8, or a pharmaceutically acceptable salt thereof, wherein $R^A$ is —C(=O)$N(R^3)(R^4)$.

Embodiment 10 provides a compound of any one of embodiments 1-9, or a pharmaceutically acceptable salt thereof, wherein $R^3$ is H.

Embodiment 11 provides a compound of any one of embodiments 1 and 3-10, or a pharmaceutically acceptable salt thereof, wherein $R^4$ is $(C_{3-7})$cycloalkyl, aryl, heterocyclyl or heteroaryl, wherein each said cycloalkyl, aryl, heterocyclyl and heteroaryl, either alone or in combination with another radical, is mono-substituted with —C(=O)—$R^{42}$;

$R^{42}$ is each independently selected from the group consisting of $(C_{1-6})$alkyl, $(C_{3-7})$cycloalkyl, —$(C_{1-6})$alkyl-aryl, —$(C_{1-6})$alkyl-heterocyclyl, —$(C_{1-6})$alkyl-heteroaryl, aryl and heteroaryl, wherein each said alkyl, cycloalkyl, aryl, heterocyclyl and heteroaryl, either alone or in combination with another radical, is optionally substituted with 1 to 3 substituents each independently selected from the group consisting of:

halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—$NH(C_{1-6})$alkyl, —C(=O)—$N((C_{1-6})$alkyl$)_2$, —$NH_2$, —$NH(C_{1-6})$alkyl, —$N((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl.

Embodiment 12 provides a compound of any one of embodiments 1-11, or a pharmaceutically acceptable salt thereof, wherein $R^4$ is heterocyclyl mono-substituted with —C(=O)—$R^{42}$;

$R^{42}$ is each independently selected from the group consisting of $(C_{5-7})$cycloalkyl, —$(C_{1-4})$alkyl-heterocyclyl, —$(C_{1-4})$alkyl-heteroaryl and heteroaryl, wherein each said alkyl, cycloalkyl, heterocyclyl and heteroaryl, either alone or in combination with another radical, is optionally mono- or di-substituted with substituents each independently selected from the group consisting of:

halo, OH, —O—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —$NH_2$, —$NH(C_{1-6})$alkyl, —$N((C_{1-6})$alkyl$)_2$, —NH—C(=O)$(C_{1-6})$alkyl and $(C_{1-6})$alkyl.

Embodiment 13 provides a compound of any one of embodiments 1-12, or a pharmaceutically acceptable salt thereof, wherein $R^4$ is heterocyclyl mono-substituted with —C(=O)-heteroaryl, wherein said heteroaryl is optionally mono- or di-substituted with substituents each independently selected from the group consisting of:

halo, OH, —O—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —$NH_2$, —$NH(C_{1-6})$alkyl, —$N((C_{1-6})$alkyl$)_2$, —NH—C(=O)$(C_{1-6})$alkyl and $(C_{1-6})$alkyl.

Embodiment 14 provides a compound of any one of embodiments 1-13, or a pharmaceutically acceptable salt thereof, wherein $R^5$ and $R^6$ are each independently $(C_{1-3})$ alkyl optionally mono-substituted with —O—$(C_{1-3})$alkyl; or $R^5$ and $R^6$ and the carbon to which they are attached are linked to form a $(C_3$-4)cycloalkyl group or a 4- to 6-membered heterocyclyl.

Embodiment 15 provides a compound of any one of embodiments 1-14, or a pharmaceutically acceptable salt thereof, wherein n is 1.

Another aspect of this invention provide a compound of any one of embodiments 1-15, or a pharmaceutically acceptable salt thereof, as a medicament.

Also within the scope of this invention is the use of a compound of Formula (I), or a pharmaceutically acceptable salt thereof, for the manufacture of a medicament for the treatment or prevention of hepatitis C viral infection in a human being.

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a hepatitis C viral infection in a human being having or at risk of having the infection.

Another aspect of the invention involves a method of treating or preventing a hepatitis C viral infection in a human being by administering to the human being an anti-hepatitis C virally effective amount of a compound of the invention, a pharmaceutically acceptable salt thereof, or a composition as described above, alone or in combination with at least one other antiviral agent, administered together or separately.

Still another aspect of this invention relates to a method of inhibiting the entry of hepatitis C virus into a cell comprising exposing the virus to an effective amount of the compound of the invention, or a salt thereof, under conditions where entry of hepatitis C virus into a cell is inhibited.

Further included in the scope of the invention is the use of a compound of the invention, or a salt thereof, to inhibit the entry of hepatitis C virus into a cell.

Yet another aspect of this invention provides a method of inhibiting replication of hepatitis C virus through the entry pathway in a human being by administering a compound of the invention, including a pharmaceutically acceptable salt thereof.

Another aspect of this invention provides a method of inhibiting the entry of the hepatitis C virus into a cell in a human being by administering a compound of the invention, including a pharmaceutically acceptable salt thereof.

DETAILED DESCRIPTION OF PREFERRED EMBODIMENTS

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "—$C_{1-3}$-alkyl-aryl" means an aryl group which is bound to a $C_{1-3}$-alkyl-group, with the $C_{1-3}$-alky group bound to the core. Unless specifically stated otherwise, for groups comprising two or more subgroups, the substituent may be attached to either subgroup.

In case a compound of the present invention is depicted in form of a chemical name and as a formula in case of any discrepancy the formula shall prevail. An asterisk or the designation, - - - - , may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

One skilled in the art would know how to separate, enrich, or selectively prepare the enantiomers of the compounds of the present invention. Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

The term "halo" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-3}$-alkyl embraces the radicals $H_3C$—, $H_3C$—$CH_2$—, $H_3C$—$CH_2$—$CH_2$— and $H_3C$—$CH(CH_3)$—.

The term "carbocyclyl" or "carbocycle" as used herein, either alone or in combination with another radical, means a mono-, bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

The term "$C_{3-n}$-cycloalkyl", wherein n is an integer 4 to n, either alone or in combination with another radical, denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to at least one other 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring system including aromatic ring systems containing one or more heteroatoms selected from N, O or $S(O)_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms.

Thus, the term "heterocyclyl" or "heterocyclyl" includes the following exemplary structures which are not depicted as radicals as each form may be attached through a covalent bond to any atom so long as appropriate valences are maintained:

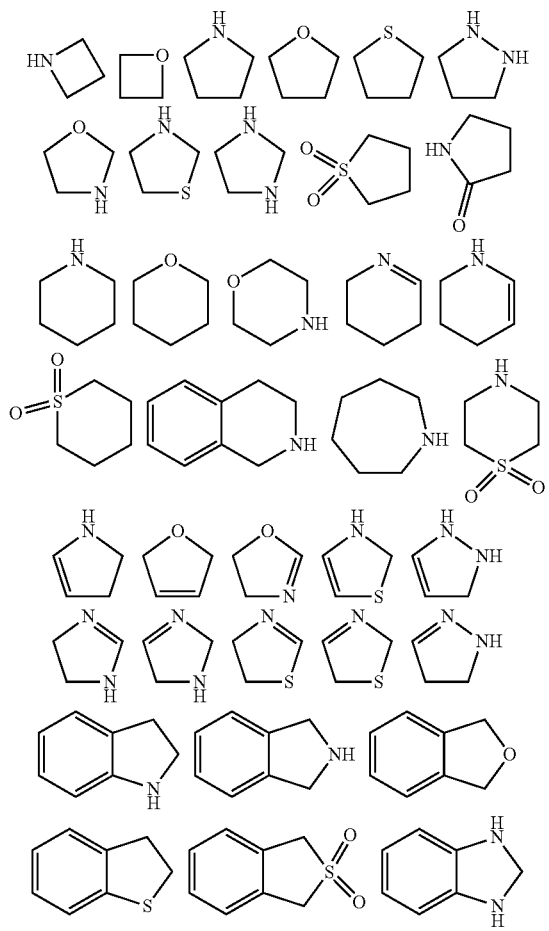

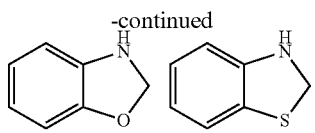

The term "heteroaryl" means a mono- or polycyclic-ring system containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

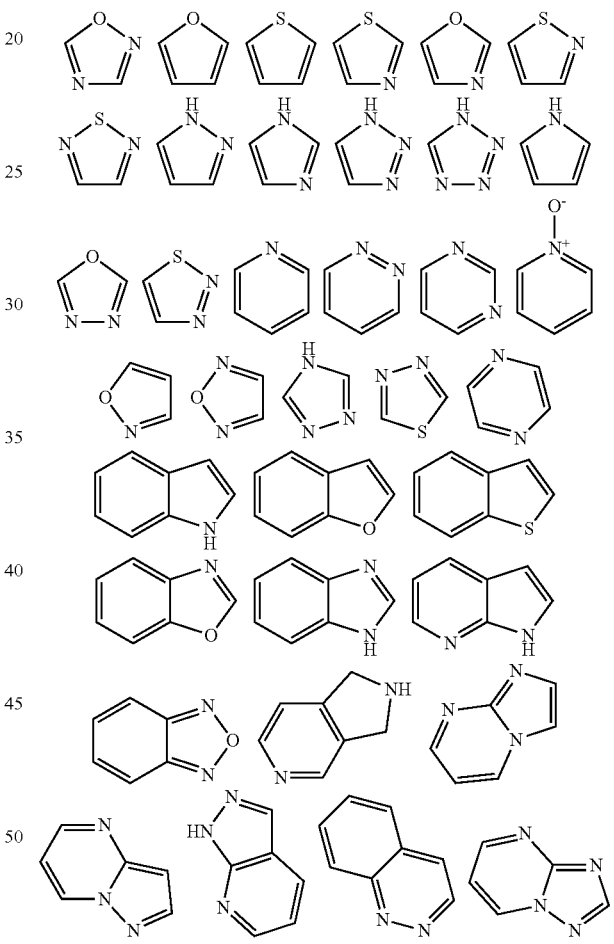

Many of the terms given above may be used repeatedly in the definition of a formula or group and in each case have one of the meanings given above, independently of one another.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term "antiviral agent" as used herein means an agent (compound or biological) that is effective to inhibit the formation and/or replication of a virus in a human being. This includes agents that interfere with either host or viral mechanisms necessary for the formation and/or replication of a virus in a human being. Such agents can be selected from: another anti-HCV agent, HIV inhibitor, HAV inhibitor and HBV inhibitor.

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, inhibitors of HCV NS5A, inhibitors of HCV polymerase or inhibitors of another target in the HCV life cycle. Examples of anti-HCV agents include, α-(alpha), β-(beta), δ-(delta), γ-(gamma), ω-(omega) or τ-(tau) interferon, pegylated α-interferon, ribavirin, amantadine, taribavirin (Viramidine), Nitazoxannide, ABT-267 and BMS-791325.

The term "immunomodulatory agent" as used herein includes those agents (compounds or biologicals) that are effective to enhance or potentiate the immune system response in a human being. Immunomodulatory agents include, but are not limited to, inosine monophosphate dehydrogenase inhibitors, class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, α-, β-, δ-, ω-, and τ-interferons, while examples of class II interferons include, but are not limited to, γ-interferons.

The term "inhibitor of HCV NS3 protease" as used herein means an agent (compound or biological) that is effective to inhibit the function of HCV NS3 protease in a human being. Inhibitors of HCV NS3 protease include, for example, the candidates telaprevir, boceprevir, danoprevir, vaniprevir, ABT-450, ACH-1625, BMS-650032, BI 201335, GS9256, IDX320, MK-5172, VX-985, ACH-2684, GS9541, and TMC43530.

The term "inhibitor of HCV polymerase" as used herein means an agent (compound or biological) that is effective to inhibit the function of an HCV polymerase in a human being. This includes, for example, nucleoside analogs or non-nucleosides inhibitors of HCV polymerase and inhibitors of HCV NS5B polymerase. Inhibitors of HCV polymerase include for example, the candidates tegobuvir, filibuvir, BI 207127, RG-7128, IDX184, PSI-7977, MK-3281, VX-222, ANA598, ABT-333, ABT-072, INX189, PSI-938, RG-7348, JTK-853, RG-7432, TMC-649128, GS-6620, BMS-791325 and IDX-375.

The term "inhibitor of HCV NS5A" as used herein means an agent (compound or biological) that is effective to inhibit the function of HCV NS5A in a human being. Inhibitors of HCV NS5A include, for example, ABT-267, BMS-824393, BMS-790052, ITMN-10050, ITMN-9916, EDP-239, AZD7295, GS-5885, GSK-2336805, IDX-380, IDX-719, ACH-2928, PPI-437, PPI-668, PPI-833 and PPI-461.

The term "inhibitor of another target in the HCV life cycle" as used herein means an agent (compound or biological) that is effective to inhibit the formation and/or replication of HCV in a human being by interfering with either host or HCV viral targets necessary for the HCV life cycle or agents which specifically inhibit in HCV cell culture assays through an undefined or incompletely defined mechanism. Inhibitors of another target in the HCV life cycle include, for example, agents that inhibit viral targets such as Core, E1, E2, p7, NS2/3 protease, NS3 helicase, NS4A, NS5A, NS5B polymerase, and internal ribosome entry site (IRES), or host targets such as cyclophilin A or B, phosphatidylinositol 4-kinase IIIα, CD81, SR-B1, Claudin 1, VAP-A, VAP-B. Specific examples of inhibitors of another target in the HCV life cycle include SCY-635, ITX5061, NOV-205, AZD7295, BIT-225, NA808, MK-1220, PF-4878691, MX-3253, GS 9450, TMC-647055, CF-102, ISIS-14803, GS9190, NIM-811, and DEBIO-025.

The term "HIV inhibitor" as used herein means an agent (compound or biological) that is effective to inhibit the formation and/or replication of HIV in a human being. This includes agents that interfere with either host or viral mechanisms necessary for the formation and/or replication of HIV in a human being. HIV inhibitors include, for example, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a human being. This includes agents that interfere with either host or viral mechanisms necessary for the formation and/or replication of HAV in a human being. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a human being. This includes agents that interfere with either host or viral mechanisms necessary for the formation and/or replication of HBV in a human being. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Preferred Embodiments

In the following preferred embodiments, groups and substituents of the compounds of Formula (I) according to this invention are described in detail.

(I)

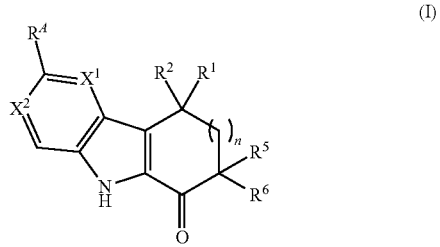

Any and each of the definitions below may be combined with each other.

$X^1$:

$X^1$-A: $X^1$ is $CR^B$ or N;

$R^B$ is H, $(C_{1-6})$alkyl, $(C_{1-6})$haloalkyl, halo, —O—$(C_{1-6})$alkyl, $NH_2$, $NH(C_{1-6})$alkyl or $N((C_{1-6})$alkyl$)_2$.

$X^1$—B: $X^1$ is CH or N.

$X^1$—C: $X^1$ is CH.

$X^2$:

$X^2$-A: $X^2$ is $CR^B$ or N;

$R^B$ is H, $(C_{1-6})$alkyl, $(C_{1-6})$haloalkyl, halo, —O—$(C_{1-6})$alkyl, $NH_2$, $NH(C_{1-6})$alkyl or $N((C_{1-6})$alkyl$)_2$.

$X^2$—B: $X^2$ is CH or N.

$X^2$—C: $X^2$ is CH.

$R^1/R^2$:

$R^1/R^2$-A: $R^1$ and $R^2$ are each independently $(C_{1-6})$alkyl optionally mono- or di-substituted with —O—$(C_{1-6})$alkyl, $NH_2$, $NH(C_{1-6})$alkyl or $N((C_{1-6})$alkyl$)_2$; or $R^1$ and $R^2$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl.

$R^1/R^2$—B: $R^1$ and $R^2$ are each independently $(C_{1-3})$alkyl optionally mono-substituted with —O—$(C_{1-3})$alkyl, $NH_2$, $NH(C_{1-3})$alkyl or $N((C_{1-3})$alkyl$)_2$; or $R^1$ and $R^2$ and the carbon to which they are attached are linked to form a $(C_{3-7})$cycloalkyl group.

$R^1/R^2$—C: $R^1$ and $R^2$ are each independently $(C_{1-3})$alkyl optionally mono-substituted with —O—$(C_{1-3})$alkyl; or $R^1$ and $R^2$ and the carbon to which they are attached are linked to form a $(C_3-4)$cycloalkyl group.

$R^A$:

$R^A$-A: $R^A$ is —C(=O)N($R^3$)($R^4$), —C(=O)O($R^4$), heterocyclyl or heteroaryl, wherein each said heterocyclyl and heteroaryl is optionally substituted 1 to 3 times with $R^{41}$;

$R^{41}$ is each independently selected from the group consisting of halo, oxo, cyano, nitro, $R^{42}$, —C(=O)—$R^{42}$, —C(=O)O$R^{42}$, —O$R^{42}$, —S$R^{42}$, —SO$R^{42}$, —SO$_2$$R^{42}$, —N($R^{43}$)$R^{42}$, —C(=O)—N($R^{43}$)$R^{42}$, —N($R^{43}$)—C(=O)$R^{42}$, —O—C(=O)—N($R^{43}$)$R^{42}$ and —SO$_2$—N($R^{43}$)$R^{42}$;

$R^{42}$ is each independently selected from the group consisting of H, $(C_{1-6})$alkyl, $(C_{3-7})$cycloalkyl, —$(C_{1-6})$alkyl-aryl, —$(C_{1-6})$alkyl-heterocyclyl, —$(C_{1-6})$alkyl-heteroaryl, aryl, heterocyclyl and heteroaryl, wherein each said alkyl, cycloalkyl, aryl, heterocyclyl and heteroaryl, either alone or in combination with another radical, is optionally substituted with 1 to 3 substituents each independently selected from the group consisting of: halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —SO$_2$$NH_2$, —SO$_2$—NH$(C_{1-6})$alkyl, —SO$_2$—N(($C_{1-6})$alkyl$)_2$, —SO$_2$$(C_{1-6})$alkyl, —C(=O)—$NH_2$, —C(=O)—NH$(C_{1-6})$alkyl, —C(=O)—N(($C_{1-6})$ alkyl)$_2$, —NH$_2$, —NH(C$_{1-6}$)alkyl, —N((C$_{1-6}$)alkyl)$_2$, —NH—C(=O)(C$_{1-6}$)alkyl and (C$_{1-6}$)alkyl optionally mono- or di-substituted with OH or —O—(C$_{1-6}$)alkyl;
R$^{43}$ is H or (C$_{1-6}$)alkyl.

R$^A$—B: R$^A$ is —C(=O)N(R$^3$)(R$^4$), heterocyclyl or heteroaryl, wherein each said heterocyclyl and heteroaryl is optionally substituted 1 or 2 times with R$^{41}$;

R$^{41}$ is each independently selected from the group consisting of —C(=O)—R$^{42}$ and —N(R$^{43}$)R$^{42}$;

R$^{42}$ is each independently selected from the group consisting of (C$_{3-7}$)cycloalkyl, —(C$_{1-6}$)alkyl-heterocyclyl, —(C$_{1-6}$)alkyl-heteroaryl, heterocyclyl and heteroaryl, wherein each said alkyl, cycloalkyl, heterocyclyl and heteroaryl, either alone or in combination with another radical, is optionally mono- or di-substituted with substitutents each independently selected from the group consisting of:

halo, OH, (C$_{1-6}$)haloalkyl, —O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —NH$_2$, —NH(C$_{1-6}$)alkyl, —N((C$_{1-6}$)alkyl)$_2$, —NH—C(=O)(C$_{1-6}$)alkyl, —C(=O)NH$_2$ and (C$_{1-6}$)alkyl;

R$^{43}$ is H or (C$_{1-6}$)alkyl.

R$^A$—C: R$^A$ is —C(=O)N(R$^3$)(R$^4$).

R$^3$:

R$^3$-A: R$^3$ is H or (C$_{1-6}$)alkyl optionally mono- or di-substituted with —O—(C$_{1-6}$)alkyl, NH$_2$, NH(C$_{1-6}$)alkyl, N((C$_{1-6}$)alkyl)$_2$, —C(=O)—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —C(=O)—NH$_2$, —C(=O)—NH(C$_{1-6}$)alkyl or —C(=O)—N((C$_{1-6}$)alkyl)$_2$.

R$^3$—B: R$^3$ is H or (C$_{1-6}$)alkyl.

R$^3$—C: R$^3$ is H.

R$^4$:

R$^4$-A: R$^4$ is H, (C$_{1-6}$)alkyl, (C$_{3-7}$)cycloalkyl, —(C$_{1-6}$)alkyl-aryl, —(C$_{1-6}$)alkyl-heterocyclyl, —(C$_{1-6}$)alkyl-heteroaryl, aryl, heterocyclyl or heteroaryl, wherein each said alkyl, cycloalkyl, aryl, heterocyclyl and heteroaryl, either alone or in combination with another radical, is optionally substituted 1 to 3 times with R$^{41}$, or R$^3$ and R$^4$, together with the N atom to which they are attached, are linked to form a heterocyclyl or heteroaryl, wherein said heterocyclyl and heteroaryl are optionally substituted 1 to 3 times with R$^{41}$;

R$^{41}$ is each independently selected from the group consisting of halo, oxo, cyano, nitro, R$^{42}$, —C(=O)—R$^{42}$, —C(=O)OR$^{42}$, —OR$^{42}$, —SR$^{42}$, —SOR$^{42}$, —SO$_2$R$^{42}$, —N(R$^{43}$)R$^{42}$, —C(=O)—N(R$^{43}$)R$^{42}$, —N(R$^{43}$)—C(=O)R$^{42}$, —O—C(=O)—N(R$^{43}$)R$^{42}$ and —SO$_2$—N(R$^{43}$)R$^{42}$;

R$^{42}$ is each independently selected from the group consisting of H, (C$_{1-6}$)alkyl, (C$_{3-7}$)cycloalkyl, —(C$_{1-6}$)alkyl-aryl, —(C$_{1-6}$)alkyl-heterocyclyl, —(C$_{1-6}$)alkyl-heteroaryl, aryl, heterocyclyl and heteroaryl, wherein each said alkyl, cycloalkyl, aryl, heterocyclyl and heteroaryl, either alone or in combination with another radical, is optionally substituted with 1 to 3 substituents each independently selected from the group consisting of: halo, cyano, OH, —COOH, —O—(C$_{1-6}$)alkyl, (C$_{3-7}$)cycloalkyl, (C$_{1-6}$)haloalkyl, —C(=O)—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —C(=O)—NH$_2$, —C(=O)—NH(C$_{1-6}$)alkyl, —C(=O)—N((C$_{1-6}$)alkyl)$_2$, —NH$_2$, —NH(C$_{1-6}$)alkyl, —N((C$_{1-6}$)alkyl)$_2$, —NH—C(=O)(C$_{1-6}$)alkyl and (C$_{1-6}$)alkyl optionally mono- or di-substituted with OH or —O—(C$_{1-6}$)alkyl;

R$^{43}$ is H or (C$_{1-6}$)alkyl.

R$^4$—B: R$^4$ is (C$_{3-7}$)cycloalkyl, aryl, heterocyclyl or heteroaryl, wherein each said cycloalkyl, aryl, heterocyclyl and heteroaryl, either alone or in combination with another radical, is mono-substituted with —C(=O)—R$^{42}$;

R$^{42}$ is each independently selected from the group consisting of (C$_{1-6}$)alkyl, (C$_{3-7}$)cycloalkyl, —(C$_{1-6}$)alkyl-aryl, —(C$_{1-6}$)alkyl-heterocyclyl, —(C$_{1-6}$)alkyl-heteroaryl, aryl and heteroaryl, wherein each said alkyl, cycloalkyl, aryl, heterocyclyl and heteroaryl, either alone or in combination with another radical, is optionally substituted with 1 to 3 substituents each independently selected from the group consisting of:

halo, cyano, OH, —COOH, —O—(C$_{1-6}$)alkyl, (C$_{3-7}$)cycloalkyl, (C$_{1-6}$)haloalkyl, —C(=O)—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —C(=O)—NH$_2$, —C(=O)—NH(C$_{1-6}$)alkyl, —C(=O)—N((C$_{1-6}$)alkyl)$_2$, —NH$_2$, —NH(C$_{1-6}$)alkyl, —N((C$_{1-6}$)alkyl)$_2$, —NH—C(=O)(C$_{1-6}$)alkyl and (C$_{1-6}$)alkyl optionally mono- or di-substituted with OH or —O—(C$_{1-6}$)alkyl.

R$^4$—C: R$^4$ is heterocyclyl mono-substituted with —C(=O)—R$^{42}$;

R$^{42}$ is each independently selected from the group consisting of (C$_{5-7}$)cycloalkyl, —(C$_{1-4}$)alkyl-heterocyclyl, —(C$_{1-4}$)alkyl-heteroaryl and heteroaryl, wherein each said alkyl, cycloalkyl, heterocyclyl and heteroaryl, either alone or in combination with another radical, is optionally mono- or di-substituted with substitutents each independently selected from the group consisting of:

halo, OH, —O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —NH$_2$, —NH(C$_{1-6}$)alkyl, —N((C$_{1-6}$)alkyl)$_2$, —NH—C(=O)(C$_{1-6}$)alkyl and (C$_{1-6}$)alkyl.

R$^4$-D: R$^4$ is heterocyclyl mono-substituted with —C(=O)-heteroaryl, wherein said heteroaryl is optionally mono- or di-substituted with substitutents each independently selected from the group consisting of:

halo, OH, —O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO$_2$(C$_{1-6}$)alkyl, —NH$_2$, —NH(C$_{1-6}$)alkyl, —N((C$_{1-6}$)alkyl)$_2$, —NH—C(=O)(C$_{1-6}$)alkyl and (C$_{1-6}$)alkyl.

R$^5$/R$^6$:

R$^5$/R$^6$-A: R$^5$ and R$^6$ are each independently H or (C$_{1-6}$)alkyl optionally mono- or di-substituted with —O—(C$_{1-6}$)alkyl, NH$_2$, NH(C$_{1-6}$)alkyl or N((C$_{1-6}$)alkyl)$_2$; or R$^5$ and R$^6$, together with the carbon to which they are attached, are linked to form a (C$_{3-7}$)cycloalkyl group or a 3- to 7-membered heterocyclyl, said cycloalkyl and heterocyclyl being optionally mono- or di-substituted with —(C$_{1-6}$)alkyl.

R$^5$/R$^6$—B: R$^5$ and R$^6$ are each independently (C$_{1-3}$)alkyl optionally mono-substituted with —O—(C$_{1-3}$)alkyl, NH$_2$, NH(C$_{1-3}$)alkyl or N((C$_{1-3}$)alkyl)$_2$; or R$^5$ and R$^6$ and the carbon to which they are attached are linked to form a (C$_{3-6}$)cycloalkyl group or a 4- to 6-membered heterocyclyl.

R$^5$/R$^6$—C: R$^5$ and R$^6$ are each independently (C$_{1-3}$)alkyl optionally mono-substituted with —O—(C$_1$-3)alkyl; or R$^5$ and R$^6$ and the carbon to which they are attached are linked to form a (C$_{3-4}$)cycloalkyl group or a 4- to 6-membered heterocyclyl.

n:

n-A: n is 0, 1 or 2.

n-B: n is 1.

Examples of preferred subgeneric embodiments of the present invention are set forth in the following table, wherein each substituent group of each embodiment is defined according to the definitions set forth above:

|      | $X^1$   | $X^2$   | $R^1/R^2$   | $R^4$   | $R^3$   | $R^4$   | $R^5/R^6$   | n   |
|------|---------|---------|-------------|---------|---------|---------|-------------|-----|
| E-1  | $X^1$-A | $X^2$-A | $R^1/R^2$-A | $R^4$-A | $R^3$-A | $R^4$-B | $R^5/R^6$-A | n-A |
| E-2  | $X^1$-A | $X^2$-A | $R^1/R^2$-B | $R^4$-B | $R^3$-A | $R^4$-B | $R^5/R^6$-B | n-A |
| E-3  | $X^1$-A | $X^2$-A | $R^1/R^2$-B | $R^4$-C | $R^3$-A | $R^4$-B | $R^5/R^6$-B | n-A |
| E-4  | $X^1$-A | $X^2$-A | $R^1/R^2$-B | $R^4$-C | $R^3$-A | $R^4$-B | $R^5/R^6$-B | n-B |
| E-5  | $X^1$-A | $X^2$-A | $R^1/R^2$-A | $R^4$-A | $R^3$-A | $R^4$-C | $R^5/R^6$-A | n-A |
| E-6  | $X^1$-B | $X^2$-B | $R^1/R^2$-B | $R^4$-B | $R^3$-B | $R^4$-B | $R^5/R^6$-B | n-A |
| E-7  | $X^1$-B | $X^2$-B | $R^1/R^2$-C | $R^4$-C | $R^3$-B | $R^4$-B | $R^5/R^6$-C | n-B |
| E-8  | $X^1$-C | $X^2$-C | $R^1/R^2$-B | $R^4$-C | $R^3$-A | $R^4$-B | $R^5/R^6$-B | n-B |
| E-9  | $X^1$-C | $X^2$-C | $R^1/R^2$-B | $R^4$-C | $R^3$-C | $R^4$-C | $R^5/R^6$-B | n-B |
| E-10 | $X^1$-C | $X^2$-C | $R^1/R^2$-C | $R^4$-C | $R^3$-C | $R^4$-C | $R^5/R^6$-C | n-B |
| E-11 | $X^1$-C | $X^2$-C | $R^1/R^2$-C | $R^4$-C | $R^3$-B | $R^4$-D | $R^5/R^6$-C | n-B |

Examples of most preferred compounds according to this invention are each single compound listed in Tables 1-10.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders. The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds according to the invention with known excipients, for example inert diluents, carriers, disintegrants, adjuvants, surfactants, binders and/or lubricants. The tablets may also consist of several layers.

Combination Therapy

Combination therapy is contemplated wherein a compound of the invention, or a pharmaceutically acceptable salt thereof, is co-administered with at least one additional agent selected from: an antiviral agent, an immunomodulatory agent, an inhibitor of HCV NS3 protease, an inhibitor of HCV polymerase, inhibitor of HCV NS5A, an inhibitor of another target in the HCV life cycle, an HIV inhibitor, an HAV inhibitor and an HBV inhibitor. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen.

EXAMPLES

Other features and advantages of the present invention will become apparent from the following more detailed Examples which illustrate, by way of example, the principles of the invention. Temperatures are given in degrees Celsius. Solution percentages express a weight to volume relationship, and solution ratios express a volume to volume relationship, unless stated otherwise.

Compounds and intermediates can be purified on a Teledyne ISCO Combiflash $R_f$ System at 254 nm using commercial normal phase silica 4-120 g Redisep $R_f$ or Silicycle columns at a flow rate of 18-85 mL/min depending on column size. Mass spectral analyses are recorded using flow injection analysis mass spectrometry or Waters Acquity Ultraperformance LC System consisting of a sample organizer, PDA detector, column manager, sample manager, binary solvent manager and SQ detector.

Preparative RP-HPLC is performed under standard conditions using one of the following specific measuring conditions:

Compounds are purified by preparative RP-HPLC under standard conditions using a Waters SunFire Prep OBD C18 column (5 um, 19×50 mm) eluting firstly with a hold period of 1 minute in initial gradient condition then eluting with a linear MeOH gradient containing 10 mM Ammonium Formate (pH 3.8) over 10 min at 30 mL/min. Fractions containing the desired product are pooled and lyophilized.

Compounds are purified by preparative RP-HPLC under standard conditions using a Waters XBridge Prep OBD C18 column (5 um, 19×50 mm) eluting firstly with a hold period of 1 minute in initial gradient condition then eluting with a linear MeOH gradient containing 10 mM Ammonium Bicarbonate (pH 10.0) over 10 min at 30 mL/min. Fractions containing the desired product are pooled and lyophilized.

Analytical UPLC is performed under standard conditions using one of the following specific measuring conditions:

Analytical UPLC is carried out under standard conditions using a Waters ACQUITY UPLC BEH C18 column (1.8 µm, 2.1×30 mm) eluting with a linear MeOH gradient containing 10 mM Ammonium Bicarbonate (pH 10) over 2.2 min at 0.75 ml/min.

Analytical UPLC is carried out under standard conditions using a Waters ACQUITY UPLC HSS C18 column (1.8 µm, 2.1×30 mm) eluting with a linear MeOH gradient containing 10 mM Ammonium Formate (pH 3.8) over 2.3 min at 0.8 ml/min.

Analytical UPLC is carried out under standard conditions using a Waters ACQUITY UPLC HSS T3 column (1.8 µm, 2.1×30 mm) eluting with a linear MeCN gradient containing 0.06% TFA (v/v) over 2.2 min at 0.9 ml/min or Waters ACQUITY UPLC BEH C18 column (1.7 µm, 2.1×30 mm) eluting with a linear MeCN gradient containing 10 mM Ammonium Bicarbonate (pH 10) over 2.2 min at 0.75 ml/min.

Abbreviations used in the examples include:
Ac: acetyl; AcOH: acetic acid; BEH: ethylene bridged hybrid; BOC or Boc: tert-butyloxycarbonyl; Bu: butyl; DCM: dichloromethane; DIPEA: diisopropylethylamine; DMAc: dimethylacetamide; DMAP: 4-dimethylaminopyridine; DMEM: Dulbecco's modified Eagle's medium; DMF: N,N-dimethylformamide; DMSO: dimethylsulfoxide; dppf: 1,1'- diphenylphosphinylferrocene; EDCI: 1-[3-(dimethylamino) propyl]-3-ethylcarbodiimide hydrochloride; Et: ethyl; Et$_2$O: diethyl ether; EtOAc: ethyl acetate; EtOH: ethanol; FBS: Fetal bovine serum; HATU: [O-(7-azabenzotriazol-1-yl)-1,1,3,3-tetramethyluronium hexafluorophosphate]; HEPES: 4-(2-hydroxyethyl)-1-piperazineethanesulfonic acid; Hex: hexanes; HPLC: high performance liquid chromatography; HSS: high strength silica; i-Pr: isopropyl; LiHMDS: lithium bis(trimethylsilyl) amide; Me: methyl; MeCN: acetonitrile; MeOH: methanol; MS: mass spectrometry (FIA MS—flow injection analysis mass spectrometry, UPLC: Ultraperformance Liquid Chromatography); [M+H]$^+$: protonated molecular ion; NEAA: non-essential amino acids; NMP: N-methyl pyrrolidinone; OBD: optimum bed density; PDA: photodiode array; Ph: phenyl; RP: reverse phase; RT: room temperature (18 to 22° C.); TEA: triethylamine; TFA: trifluoroacetic acid; THF: tetrahydrofuran; TMS: trimethylsilyl; TPAP: tetra-n-propyl ammonium perruthenate; $t_R$: retention time; VSV: vesicular stomatitis virus.

Example 1

Preparation of Intermediates 1a3 and 1a5

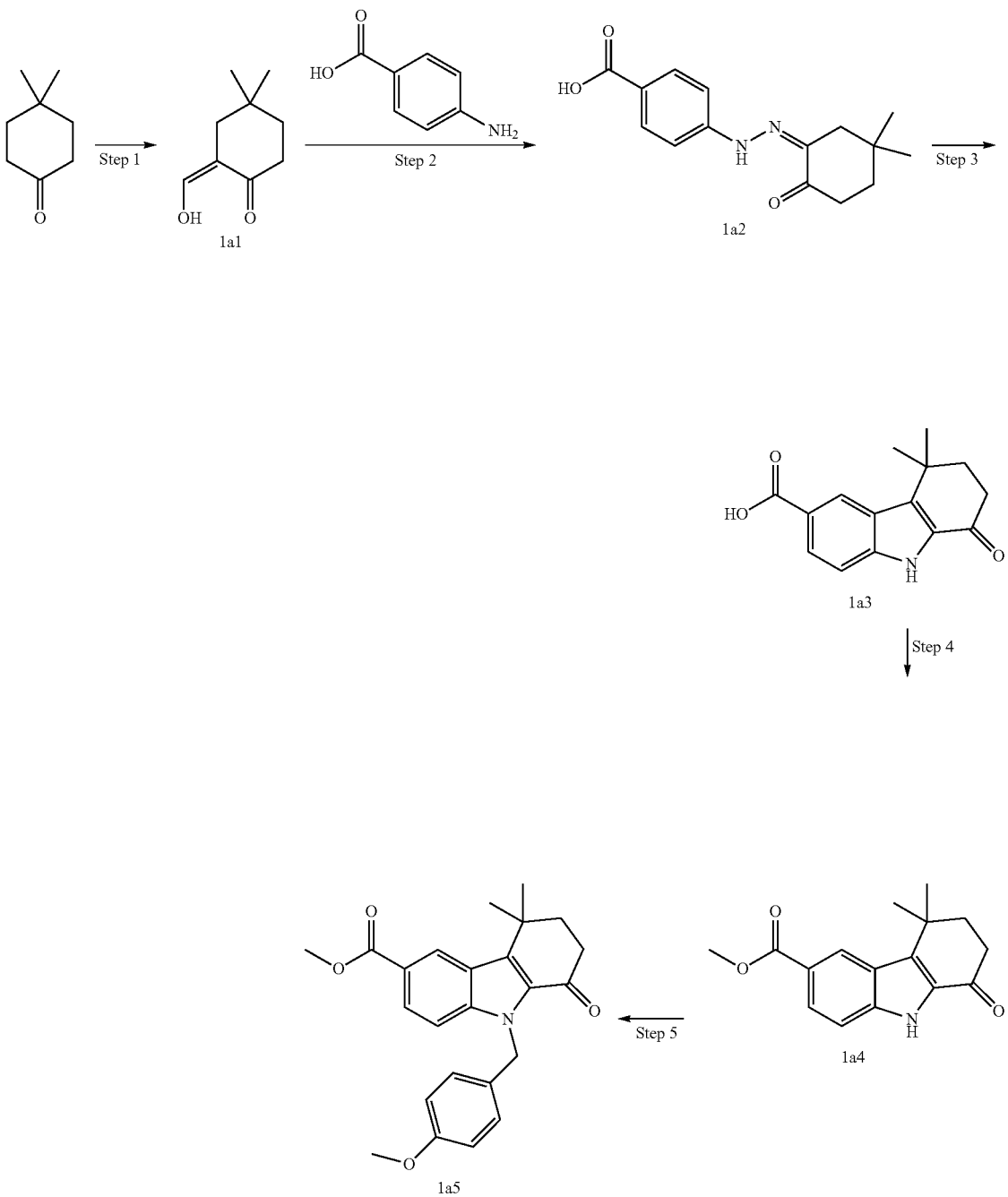

Step 1:

To a 00° C. mixture of NaH (60% in oil, 0.65 g, 15.0 mmol) in EtOH (0.1 mL) and ether (30 mL) is added a solution of cyclohexanone (1.9 g, 15.0 mmol, Combi-blocks) and ethylformate (1.8 mL, 22.5 mmol) in ether (40 mL) over a period of 1 h. The reaction mixture is allowed to warm to RT overnight. EtOH (1.5 mL) is added and the reaction mixture is stirred for 1 h. Water (40 mL) is added and the ether layer is washed with water. The aqueous layer is acidified with 6N HCl and extracted with ether. The combined organic extracts are washed with water, brine, dried over $MgSO_4$ and concentrated to afford 1a1 which is used as such in the next step.

Step 2:

1a1 (1.15 g, 7.5 mmol) is dissolved in MeOH (30 mL), NaOAc (1.4 g, 16 mmol) and water (30 mL) are added and the resulting solution 1-1 is cooled to 00° C. In a separate vessel, 4-aminobenzoic acid (1.0 g, 7.5 mmol, Aldrich) is cooled to 0° C., taken up in water (30 mL) and concentrated HCl is added (2.2 mL). To this is added a saturated solution of $NaNO_2$ (0.9 g, 15 mmol, 9 mL of water). The solution is then added to solution 1-1 and the reaction mixture is allowed to stir for 30 min. The precipitate is filtered, washed with water and dried to provide 1a2.

Step 3:

1a2 (1.75 g, 6.4 mmol) is taken up in formic acid (70 mL) and heated at 100° C. for 12 h. The reaction is cooled to RT and poured into cold water (100 mL). The resulting precipitate is filtered, washed with cold water and dried to provide 1a3.

Step 4:

1a3 suspended in MeOH (25 mL) is treated with diazomethane (0.68M, 10 mL). MeOH (50 mL) and diazomethane (15 mL) are again added and the reaction mixture is stirred at RT for 1 h. The solvents are evaporated in vacuo and the residue is dried under vacuum to provide 1a4.

Step 5:

To 1a4 (2.10 g, 7.74 mmol) in DMF (20 mL), is added NaH (60% in oil, 350 mg, 8.75 mmol). After 5 min, 4-methoxybenzyl chloride (1.16 mL, 8.55 mmol) is added and the resulting solution is stirred at RT overnight. The reaction mixture is diluted with EtOAc, then washed with an aqueous solution of saturated $NaHCO_3$, $H_2O$ (2×) and brine, dried over $MgSO_4$, concentrated and purified by Combiflash (90:10 Hex/EtOAc) to afford 1a5.

Example 2

Preparation of Intermediate 2a1

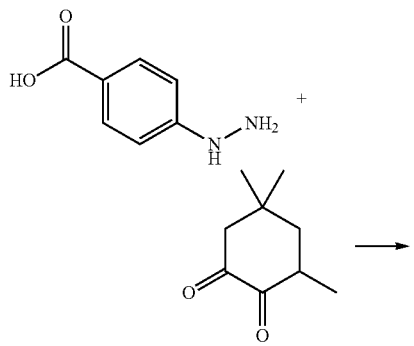

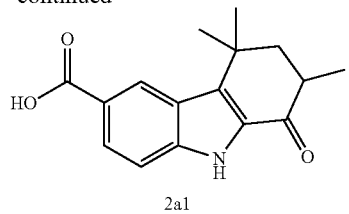

To a solution of 4-hydrazinobenzoic acid (2.0 g, 13.1 mmol, Acros) and 3,5,5-trimethyl-1,2-cyclohexdione (2.0 g, 13.1 mmol, Acros) in AcOH (40 mL) is added concentrated HCl (7.5 mL). The reaction mixture is stirred at 85° C. for 18 h then quenched with water and filtered. The residue is washed with water to provide 2a1.

Example 3

Preparation of Intermediate 3a2

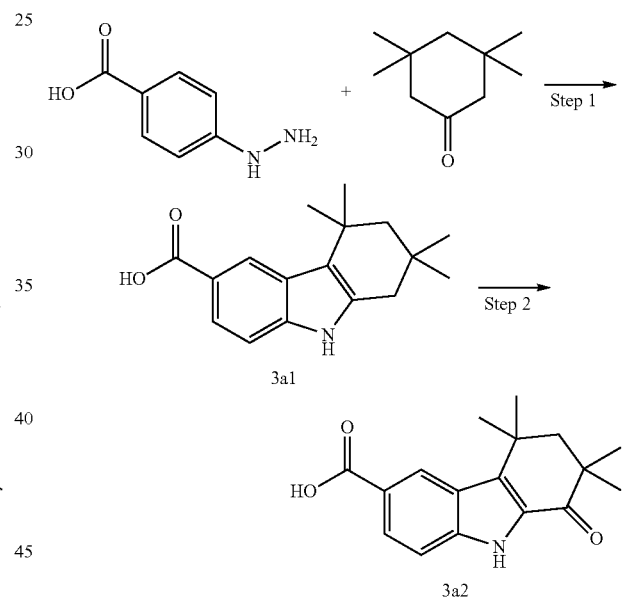

Step 1:

4-hydrazinobenzoic acid (3.0 g, 20 mmol, Acros) is added to a solution of 3,3,5,5-tetramethylcyclohexanone (3.5 mL, 20 mmol, Aldrich) in AcOH (30 mL) under nitrogen over a period of 1 h. The reaction mixture is refluxed for 1 h, and then cooled to RT and $BF_3.Et_2O$ (3.7 mL, 30 mmol, Aldrich) is added. The reaction mixture is stirred at reflux for 3 h and then concentrated. The residue is diluted with iced water and the aqueous layer is extracted with EtOAc (3×). The organic layers are combined, washed with brine, dried over $MgSO_4$, filtered, concentrated and purified by Combiflash (100% Hex to 50% EtOAc/Hex) to afford 3a1.

Step 2:

To a stirred solution of 3a1 (2.2 g, 7.9 mmol) in THF (20 mL) and water (6.0 mL) is added diiodine pentoxide (3.2 g, 9.5 mmol). The reaction mixture is stirred at 65° C. for 4 h. The solvent is removed and the residue is extracted with EtOAc. The organic layer is washed with water (pH<7), brine and dried over MgSO₄. After removal of the solvent, the residue is triturated with EtOAc to provide 3a2.
Example 4
Preparation of Intermediate 4a13
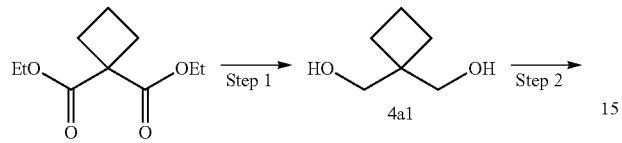
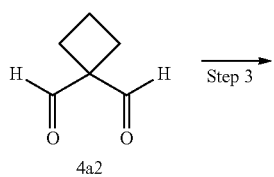
4a2
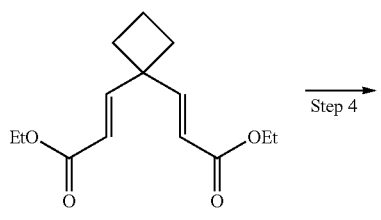
4a3
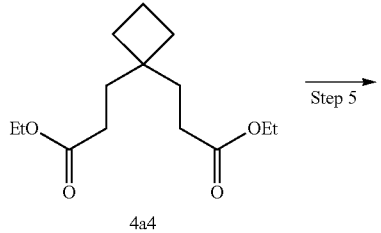
4a4
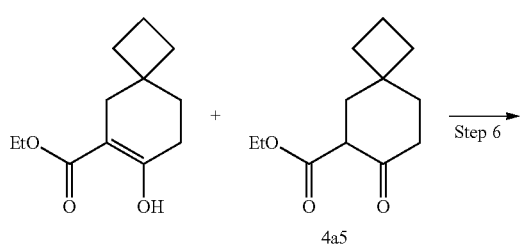
4a5
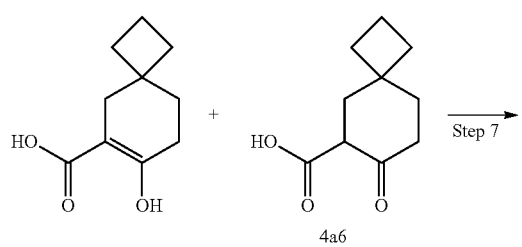
4a6
-continued
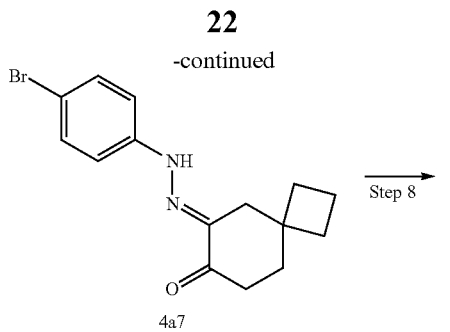
4a7
4a8
4a9
4a10
4a11

-continued

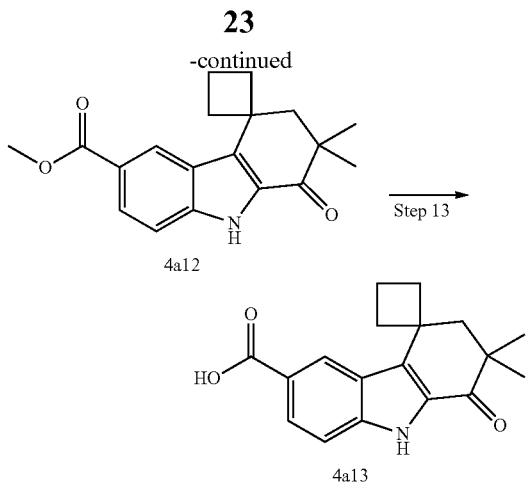

4a12

4a13

Step 1:
Lithium aluminum hydride bis(THF) (432 mL, 1.0 M in toluene, 432 mmol) is added over a period of 1.25 h to a −20° C. (internal temperature) solution of diethyl cyclobutane-1,1-dicarboxylate (57.5 g, 288 mmol, VWR) in THF (1.00 L). The reaction mixture is allowed to warm to an internal temperature of 00° C. over 1 h, and kept at 0° C. for 0.5 h. While maintaining an internal temperature of 00° C., the reaction mixture is quenched sequentially with water (60 mL), 15 wt. % aqueous NaOH (60 mL) and water (170 mL). The mixture is further diluted with THF (500 mL), and then stirred as it warms to RT. The mixture is filtered through Celite and the Celite pad is rinsed with THF. The filtrate is dried over anhydrous $Na_2SO_4$ and concentrated under reduced pressure to provide 4a1.

Step 2:
Oxalyl chloride (61.5 mL, 708 mmol) is added over 1.5 h to a −80° C. (internal temperature; $Et_2O$/dry-ice bath is used for cooling) solution of DMSO (50.2 mL, 708 mmol) in DCM (3.00 L). The reaction mixture is allowed to stir at −80° C. for 0.5 h, and then a solution of 4a1 (30.9 g, 266 mmol) in DCM (500 mL) is added over 1 h while maintaining an internal temperature of −80° C. The reaction mixture is stirred for 0.5 h at −80° C., and then TEA (297 mL, 2.13 mol) is added over 1 h while keeping an internal temperature of −80° C. The cooling bath is removed, and the reaction mixture is allowed to warm to 10° C. over 4 h. The crude material containing 4a2 is used as such in the next step.

Step 3:
The solution containing 4a2 is transferred to an addition funnel connected to a 12 L multi-neck flask fitted with a mechanical stirrer. The reaction mixture is added over 40 min to a solution of triethyl phosphonoacetate (141 mL, 708 mmol), anhydrous LiCl (60.0 g, 1.42 mol) and DIPEA (492 mL, 2.83 mol) in MeCN (2.12 L). The resulting mixture is stirred at RT for 16 h, and then concentrated under reduced pressure to ~500 mL. The suspension is diluted with $Et_2O$ (4.0 L) and water (2.0 L). The layers are separated and the aqueous phase is extracted with $Et_2O$ (4.0 L). The combined organic extracts are washed with water (2.0 L), aqueous saturated $NaHCO_3$ (2.0 L) and aqueous saturated NaCl (2.0 L), dried over anhydrous $Na_2SO_4$, filtered, concentrated under reduced pressure and purified by Combiflash (5% EtOAc/Hex) to provide 4a3.

Step 4:
Palladium on activated carbon (22.5 g, 10 wt. %, wet, Degussa type E101 NE/W, 10.6 mmol, Strem) is added to a solution of 4a3 (53.3 g, 212 mmol) in EtOAc (2.10 L). The suspension is divided approximately equally between two 2 L round-bottom flasks, and each flask is capped with an airfree adapter fitted with a balloon filled with hydrogen gas. The systems are purged with hydrogen gas (3×), and then allowed to stir under a hydrogen atmosphere for 2 days. The reaction mixtures are filtered through Celite with EtOAc washings (3×100 mL). The filtrate is concentrated under reduced pressure and purified by Combiflash (5% EtOAc/Hex) to provide 4a4.

Step 5:
Potassium tert-butoxide (39.0 g, 347 mmol) is added to a solution of 4a4 (44.5 g, 174 mmol) in THF (1.75 L). The resulting mixture is heated to reflux, and then stirred at reflux for 1 h. The reaction mixture is cooled to an internal temperature of −10° C., quenched with 1M HCl (700 mL), and then allowed to warm to RT. The solution is diluted with $Et_2O$ (4.0 L) and the layers are separated. The organic layer is washed with aqueous saturated NaCl (700 mL), dried over anhydrous $Na_2SO_4$, filtered, concentrated under reduced pressure and purified by Combiflash (2.5% EtOAc/Hex) to provide 4a5.

Step 6:
4a5 (750 mg, 3.58 mmol) is charged in a round bottom flask with water (10 mL) and 5N NaOH (0.78 mL, 3.92 mmol) and the resulting mixture is stirred for 24 h. The reaction mixture is transferred to a separatory funnel and washed with ether (2×). The aqueous layer is transferred back to its original flask, cooled to 0° C. and quenched with 1 equivalent of 6N HCl (until pH is approximately 4-5). The mixture is stirred at 0° C. for 25 min to afford 4a6 which is used as such in the next step.

Step 7:
To the aqueous solution of 4a6 (619 mg, 3.40 mmol) at 0° C. is added over 20 min a solution of 4-bromobenzenediazonium tetrafluoroborate (920 mg, 3.40 mmol) in water (12 mL). The resulting mixture is stirred at 0° C. for 10 min, and then is stirred at RT for 30 min. The reaction mixture is filtered and the residue is dissolved in EtOAc, washed with brine, dried over $MgSO_4$, filtered and concentrated under reduced pressure to provide 4a7, which is used as such in the next step.

Step 8:
4a7 (1.09 g, 3.40 mmol) is suspended in MeCN (27 mL) and 1.8M sulfuric acid (5.7 mL, 10.2 mmol) is added. The reaction mixture is stirred for 4 h at 80° C., then cooled to RT and concentrated under reduced pressure to remove approximately half of the MeCN. Water (50 mL) is added, and the mixture is stirred for 1 h. The mixture is filtered and the residue is purified by Combiflash (100% Chloroform, then Chloroform/MeOH 95%/5%) to give 4a8.

Step 9:
To a solution of 4a8 (582 mg, 1.91 mmol) in DMF (12 mL) is added 4-methoxybenzyl chloride (312 μL, 2.30 mmol). The reaction mixture is cooled to 0° C., and NaH (60% in oil, 84.2 mg, 2.11 mmol) is added. The reaction mixture is stirred for 5 min at 0° C., and then stirred at RT for 4 h. The reaction mixture is poured into 1M HCl and extracted with EtOAc. The organic layer is washed with 1M HCl, washed with brine, dried over $MgSO_4$, filtered, concentrated under reduced pressure and purified by Combiflash (100% Hex to 25% EtOAc in Hex) to give 4a9.

Step 10:
To a solution of 4a9 (631 mg, 1.49 mmol) in DMF (10 mL) at 0° C. is added NaH (60% in oil, 217 mg, 5.43 mmol), followed by iodomethane (0.29 mL, 4.65 mmol). The reaction mixture is stirred for 5 min, then the ice bath is removed, and the reaction mixture is allowed to stir at RT for 4 h. The reaction mixture is quenched with 1N HCl and extracted with EtOAc. The organic layers are combined, washed with water (2×), washed with brine (2×), dried over MgSO$_4$, filtered, concentrated under reduced pressure and purified by Combiflash (Hex/EtOAc 100:0 to 85:15) to provide 4a10.

Step 11:

To a solution of 4a10 (368 mg, 0.81 mmol) in DMSO (10 mL) and MeOH (5 mL), is added TEA (0.60 mL, 4.28 mmol). The resulting flask is fitted with a condenser and the solution is purged with CO(g) for 10 min. Pd(dppf)Cl$_2$-DCM adduct (77 mg, 0.09 mmol, Strem) is added and the reaction mixture is heated at 85° C. under 1 atmosphere of CO(g) for 8 h. The solution is cooled to RT and diluted with EtOAc. The organic phase is washed with water (3×), washed with brine, dried over MgSO$_4$ and concentrated under reduced pressure to afford crude 4a11 which is used as such in the next step.

Step 12:

To a solution of 4a11 (351 mg, 0.83 mmol) in DCM (3.0 mL) is added trifluoroacetic acid (1.5 mL). The reaction mixture is stirred at RT for 1.5 h, then concentrated under reduced pressure, diluted with MeOH and concentrated under reduced pressure (2×). The residue is purified by Combiflash (DCM/MeOH 100:0 to 9:1) to provide 4a12.

Step 13:

4a12 (868.0 mg, 2.79 mmol) is dissolved in DMSO (45.00 mL) and cooled to 0° C. A 1N NaOH solution (11.1 mL, 11.13 mmol) is added to the solution. The mixture is warmed to 45° C. and stirred for 3 h. The mixture is quenched with 1N HCl (11.1 mL, 11.13 mmol) and extracted with EtOAc. The organic layers are combined, washed with brine (2×), dried over MgSO$_4$, filtered and concentrated under reduced pressure to afford 4a13 which is used as such in subsequent reactions.

Example 5

Preparation of Intermediate 5a9

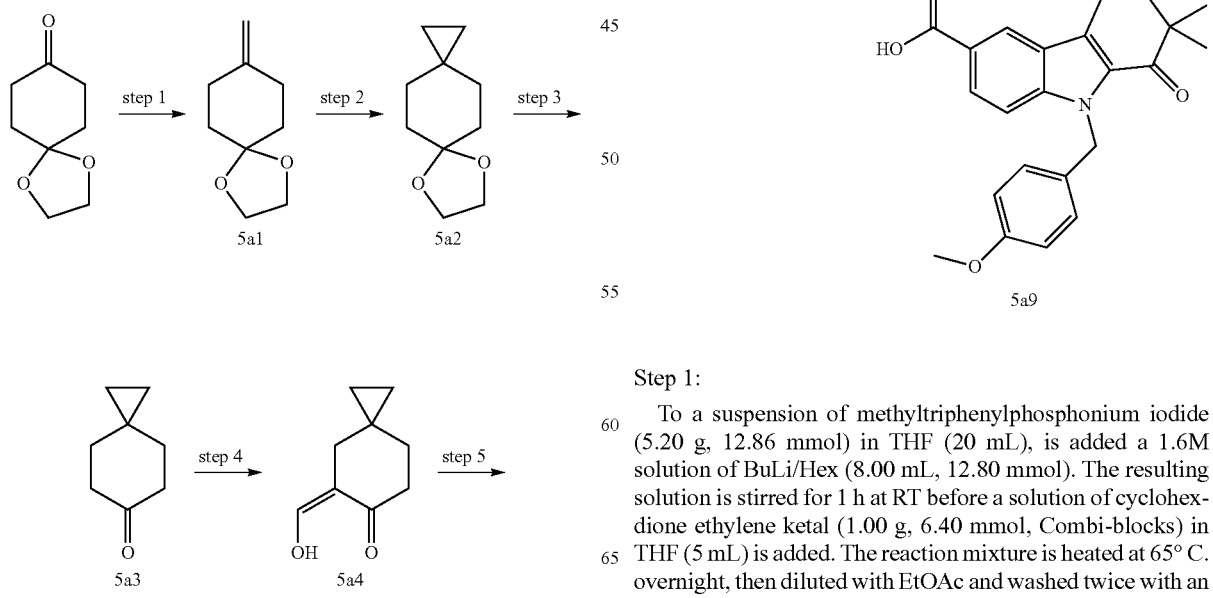

Step 1:

To a suspension of methyltriphenylphosphonium iodide (5.20 g, 12.86 mmol) in THF (20 mL), is added a 1.6M solution of BuLi/Hex (8.00 mL, 12.80 mmol). The resulting solution is stirred for 1 h at RT before a solution of cyclohexdione ethylene ketal (1.00 g, 6.40 mmol, Combi-blocks) in THF (5 mL) is added. The reaction mixture is heated at 65° C. overnight, then diluted with EtOAc and washed twice with an aqueous solution of saturated NaHCO$_3$ and brine. The filtrate is dried over anhydrous $Na_2SO_4$, concentrated under reduced pressure and purified by Combiflash (95:5 Hex/EtOAc) to provide 5a1.

Step 2:

A solution of 5a1 (0.45 g, 2.91 mmol) in ether (2.5 mL) is cooled to 0° C. then a solution of diazomethane (0.68M, 15 mL, 10.20 mmol) is added. Palladium acetate (60 mg, 0.27 mmol) is added portionwise with diazomethane (~50 mL total) being added after each portion of the catalyst. The reaction mixture is filtered and the ether is evaporated to afford 5a2.

Step 3:

To a solution of 5a2 (0.46 g, 2.73 mmol) in THF (10 mL) is added 1M HCl (10 mL, 10 mmol). The resulting solution is stirred for 4 h at RT, then diluted with $H_2O$ and extracted with ether (3×). The filtrate is dried over anhydrous $Na_2SO_4$ and concentrated under reduced pressure to provide 5a3.

Step 4:

A suspension of NaH (60% in oil, 1.10 g, 27.50 mmol) in ether (60 mL) and EtOH (0.2 mL) is cooled to 0° C. before a solution of cyclohexanone 5a3 (3.40 g, 27.38 mmol) and ethylformate (3.30 mL, 41.02 mmol) in ether (70 mL) is added over a period of 40 min. The temperature is allowed to raise to RT overnight. The reaction mixture is diluted with $H_2O$ and extracted with ether. The aqueous phase is acidified with 1M HCl and extracted with ether (2×). The filtrate is dried over anhydrous $Na_2SO_4$ and concentrated under reduced pressure to provide 5a4.

Step 5:

To 5a4 (1.44 g, 9.46 mmol) in MeOH (38 mL) is added NaOAc (1.80 g, 20.69 mmol) and $H_2O$ (38 mL). The resulting solution 5-1 is cooled to 0° C. In another flask, 4-aminobenzoic acid (1.30 g, 9.48 mmol, Aldrich) suspended in $H_2O$ (38 mL) is cooled to 0° C., and then concentrated HCl (2.8 mL) followed by a saturated solution of sodium nitrite (1.15 g, 19.16 mmol) in $H_2O$ (11.5 mL) is added. After 10 min, this solution is added to the solution 5-1 and the resulting mixture is stirred at 0° C. for 1 h. The mixture is filtered, washed with water and dried under vacuum to provide 5a5.

Step 6:

A solution of 5a5 (0.99 g, 3.63 mmol) in formic acid (50 mL) is heated for 10 h at 100° C. Heating is stopped and then the reaction mixture is allowed to reach RT before being poured into $H_2O$. The resulting precipitate is filtered to afford 5a6.

Step 7:

5a6 (270 mg, 1.06 mmol) is suspended in MeOH (10 mL) and treated with diazomethane (0.68M, 15 mL). The reaction mixture is stirred at RT for 1 h. The solvents are evaporated in vacuo and the residue is triturated with MeOH and filtered to provide 5a7.

Step 8:

To 5a7 (224 mg, 0.83 mmol) in DMF (2 mL) is added NaH (60% in oil, 40 mg, 1.00 mmol) followed, 5 min later, by 4-methoxybenzyl chloride (0.125 mL, 0.92 mmol). The resulting solution is stirred for 3 h at RT. The reaction mixture is diluted with EtOAc, washed with an aqueous solution of saturated $NaHCO_3$, $H_2O$ (2×) and brine. The filtrate is dried over anhydrous $Na_2SO_4$, concentrated under reduced pressure and purified by Combiflash (90:10 Hex/EtOAc) to provide 5a8.

Step 9:

To a solution of 5a8 (270 mg, 0.69 mmol) and MeI (0.12 mL, 1.93 mmol) in DMF (5 mL) is added NaH (60% in oil, 100 mg, 2.50 mmol). The reaction mixture is stirred for 4 h at RT. NaOH (1M, 1.4 mL, 1.40 mmol) is added and the reaction mixture is left overnight. The reaction mixture is diluted with $H_2O$ and extracted with ether. The aqueous phase is acidified with 1M HCl and extracted with EtOAc (2×). The filtrate is dried over anhydrous $Na_2SO_4$ and concentrated under reduced pressure to afford 5a9.

Example 6

Preparation of Intermediate 6a4

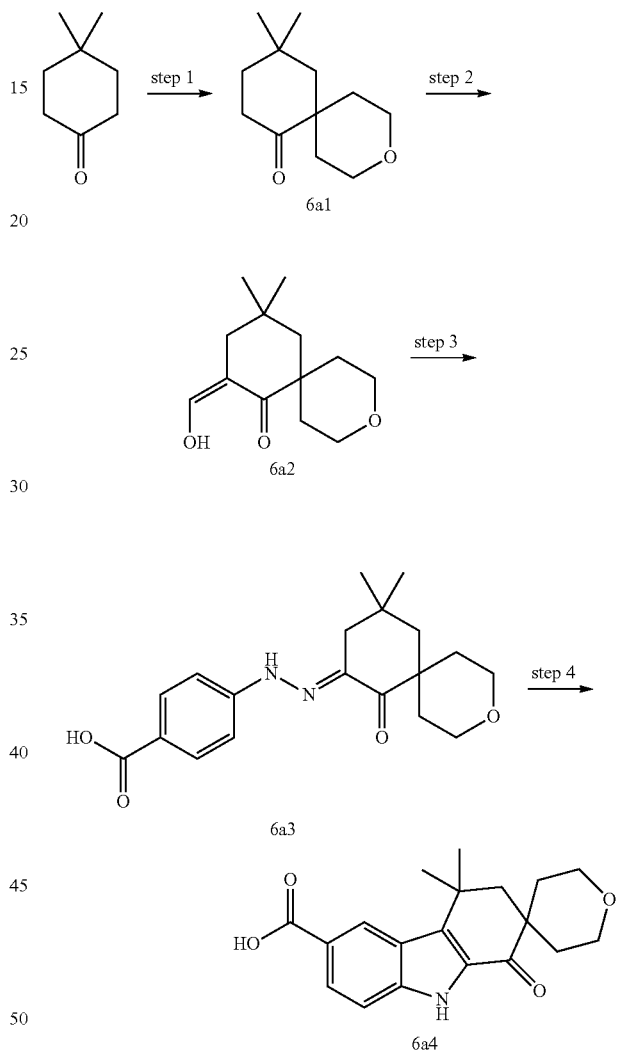

Step 1:

NaH (60% in oil, 975 mg, 24.38 mmol) is washed with pentane (3×) and then suspended in dry THF (10 mL). A solution of 4,4-dimethyl cyclohexanone (1.02 g, 8.12 mmol, Combi-Blocks) in THF (5 mL) is added, followed by bis-2-iodoethyl ether (1.25 mL, 8.80 mmol). The reaction mixture is heated to 65° C. When an exothermic reaction occurs, external heating is stopped and the reaction mixture is stirred for 1.5 h. The reaction mixture is heated at reflux for 30 min, and then is poured into water and extracted with ether. The aqueous phase is acidified to pH 6 with 1M HCl and extracted with ether (2×). The filtrate is dried over anhydrous $Na_2SO_4$, concentrated under reduced pressure and purified by Combiflash (90:10 Hex/EtOAc) to afford 6a1.

Step 2:

6a2 is prepared from 6a1 according to an analogous procedure to that described for the synthesis of 1a1 (Example 1, Step 1).

Step 3:

6a3 is prepared from 6a2 according to an analogous procedure to that described for the synthesis of 1a2 (Example 1, Step 2).

Step 4:

6a4 is prepared from 6a3 according to an analogous procedure to that described for the synthesis of 1a3 (Example 1, Step 3).

Example 7

Preparation of Intermediate 7a3

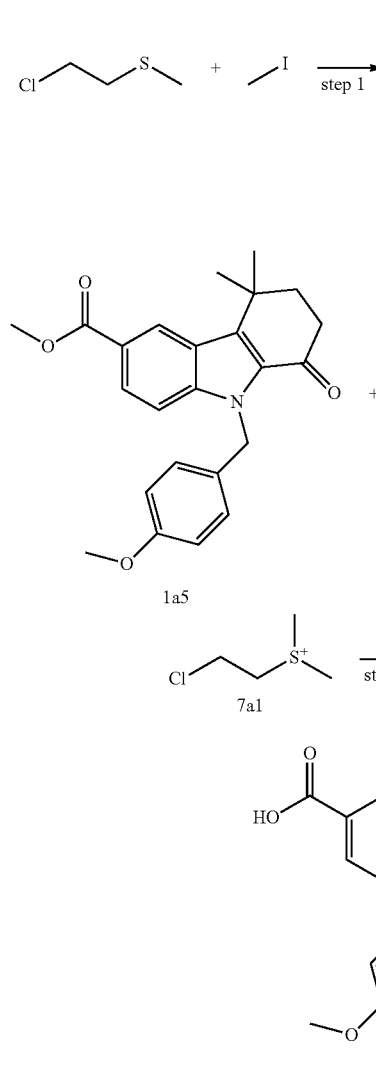

Step 1:

To methyl-2-chloroethylsulfide (1.00 mL, 10.03 mmol, Aldrich) in MeOH (3 mL) is added methyl iodide (1.25 mL, 20.08 mmol, Aldrich). The resulting solution is stirred overnight at RT, and then diluted with ether. The reaction mixture is filtered and the residue is rinsed with ether and triturated with MeOH (2×). After drying, 7a1 is obtained.

Step 2:

To a suspension of NaH (60% in oil, 67 mg, 1.67 mmol) in DMF (5 mL) is added a solution of 1a5 (250 mg, 0.64 mmol) in DMF (5 mL). 7a1 (96 mg, 0.76 mmol) is then added over a period of 15 min and the resulting solution is stirred for 3 h at RT. The reaction mixture is diluted with 1M HCl and extracted with EtOAc (2×). The organic phases are combined, washed with water (3×) and brine (1×), dried over MgSO₄, filtered, concentrated under reduced pressure and purified by preparative RP-HPLC to afford 7a3.

Example 8

Preparation of Intermediate 8a1

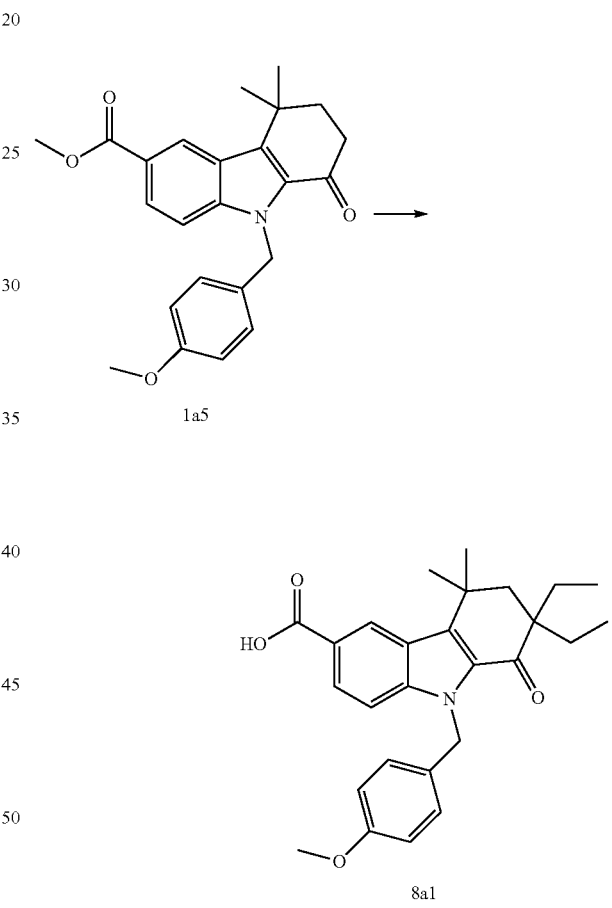

To a solution 1a5 (250 mg, 0.64 mmol) and ethyl iodide (0.153 mL, 1.91 mmol), in DMF (2.5 mL) is added NaH (60% in oil, 78 mg, 1.95 mmol). The resulting mixture is stirred for 2 h at RT, then diluted with 1M HCl and extracted with EtOAc (2×). The organic phases are combined and washed with water (3×) and brine (1×), then concentrated under reduced pressure. The residue is dissolved in THF:H₂O (2.5:1, 7 mL) and MeOH (2.5 mL), then 1M NaOH is added (1.36 mL, 1.36 mmol). The reaction mixture is stirred overnight at RT, and then heated for 3 h at 50° C. The solvents are removed in vacuo and the residue is diluted with 1M HCl and extracted

Example 9

Preparation of Intermediate 9a3

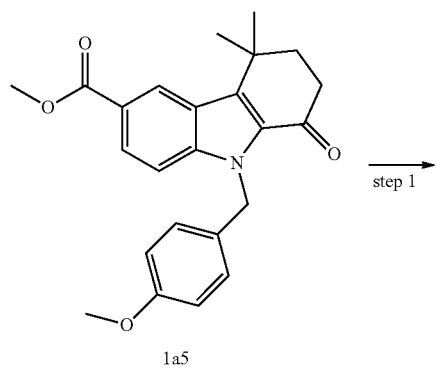
1a5 step 1 →

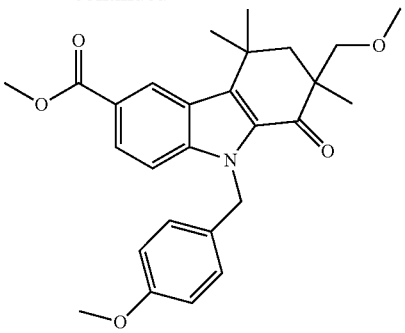
9a2 step 3 ↓

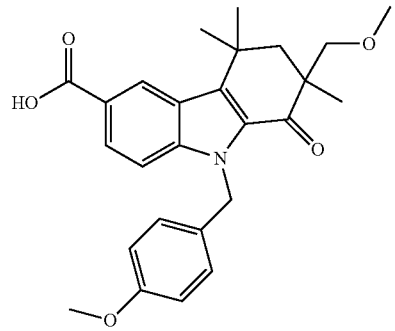
9a3

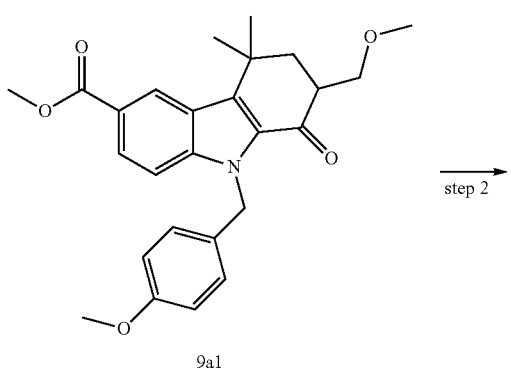
9a1 step 2 →

Step 1:

A solution of 1a5 (1.00 g, 2.55 mmol) in THF (10 mL) is cooled to −45° C. before LiHMDS (1 M, 3.00 mL, 3.00 mmol) is added. After 20 min, bromomethylmethyl ether (0.23 mL, 2.81 mmol) is added. The cooling bath is then removed and the solution is allowed to reach RT over 1 h. The reaction mixture is quenched with water, diluted with EtOAc, washed with an aqueous solution of saturated NaHCO$_3$ and brine, dried over MgSO$_4$, filtered, concentrated under reduced pressure and purified by Combiflash (30:70 Hex/DCM) to provide 9a1.

Step 2:

To a solution of 9a1 (291 mg, 0.67 mmol) and methyl iodide (0.415 mL, 6.67 mmol) in DMF (2.5 mL) is added NaH (60% in oil, 55 mg, 1.37 mmol). The resulting mixture is stirred for 1 h at RT. The reaction mixture is quenched with water, diluted with EtOAc, washed with an aqueous solution of saturated NaHCO$_3$, water and brine, dried over MgSO$_4$, filtered, concentrated under reduced pressure and purified by Combiflash (85:15 Hex/EtOAc) to afford 9a2.

Step 3:
9a3 is prepared from 9a2 according to an analogous procedure to that described in Example 5, Step 9.

Example 10

Preparation of Intermediate 10a5

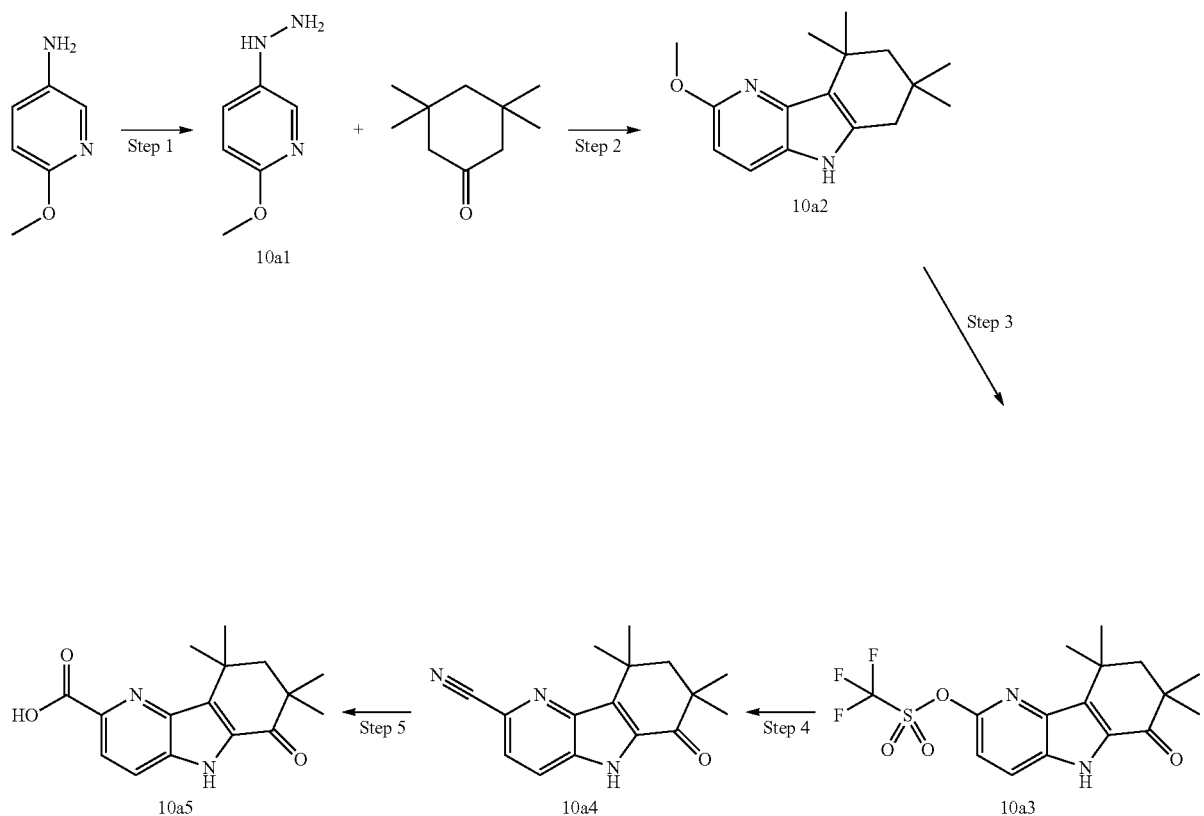

Step 1:
To a solution of 5-amino-2-methoxypyridine (3 g, 24.2 mmol, Aldrich) in 6N HCl (27 mL) at 0° C. is added a solution of sodium nitrite (1.67 g, 24.2 mmol) in water (13.2 mL). After 30 min at 0° C., a solution of $SnCl_2.2H_2O$ (13.69 g, 60.7 mmol) in 6N HCl (27 mL) is added at 00° C. This reaction mixture is stirred for 3 h at 0° C. and allowed to warm to RT for 1 h. The reaction mixture is quenched by the addition of an aqueous solution of KOH (40% w/w, until the pH turns basic, ~70 mL). The crude material is extracted with EtOAc (6×). The organic layers are combined, dried over $MgSO_4$, filtered and concentrated under reduced pressure to give 10a1.

Step 2:
To a solution of 10a1 (2.8 g, 20.1 mmol) in 4% w/w aqueous $H_2SO_4$ (42 mL) is added 3,3,5,5-tetramethylcyclohexanone (3.48 mL, 20.1 mmol, Aldrich). The reaction mixture is stirred for 2 h at 100° C., then is cooled to RT. EtOAc (600 mL) is added and the reaction mixture is washed with NaOH (until pH is basic), brine and filtered using a phase separator. The solvent is evaporated and purification by Combiflash (30% EtOAc/Hex) affords 10a2.

Step 3:
In a microwave vial, 10a2 (1.91 g, 7.39 mmol) in AcOH (35 mL) is treated with $MnO_2$ (1.29 g, 14.8 mmol). The vial is capped, and the resulting mixture is heated to 90° C. for 1 h. The reaction mixture is filtered, and then HBr (7 mL, 48%/AcOH) is added. The resulting mixture is heated to 100° C. for 5 h. The reaction mixture is allowed to cool to RT and is then concentrated. EtOAc is added, followed by water. The aqueous layer is extracted with EtOAc (2×) and the combined organic phases are filtered using a phase separator. The solvent is evaporated and to the residue in anhydrous DCM (200 mL) at 0° C. is added pyridine (5.95 mL, 73.9 mmol) followed by triflic anhydride (2.49 mL, 14.8 mmol). The resulting solution is allowed to warm to RT and is stirred overnight. A saturated aqueous solution of $NaHCO_3$ (100 mL) is added and the mixture is extracted with DCM (3×), filtered using a phase separator and the solvent is evaporated. Purification by Combiflash (20% EtOAc/Hex) affords 10a3.

Step 4:
To a solution of 10a3 (300 mg, 0.77 mmol) in anhydrous DMF (4 mL) is added zinc cyanide (180 mg, 1.54 mmol) and $Pd[P(Ph_3)]_4$ (133 mg, 0.11 mmol). The vial is capped and submitted to microwave conditions (Biotage Initiator Sixty; Vial: 2-5 mL; Pre-stirring: 10 sec; Absorption level: High; Run time: 20 min; temperature: 125° C.). EtOAc (100 ml) is added, and the mixture is washed with brine (3×). The organic layer is filtered using a phase separator and the solvent is evaporated. Purification by Combiflash (EtOAc/Hex) affords 10a4.

Step 5:

A mixture of 10a4 (156 mg, 0.58 mmol) in 10N NaOH (2.0 mL, 20.0 mmol) and EtOH (2 mL) is heated to 900° C. for 16 h. The reaction mixture is acidified using 6N HCl and extracted with EtOAc (3×). The combined organic layers are filtered using a phase separator and the solvent is evaporated to afford 10a5 that is used as is in subsequent reactions.

Example 11

Preparation of Intermediate 11a6

Step 3:

To a solution of 11a2 (600 mg, 2.02 mmol) in MeOH (20 mL) is added ammonium formate (509.2 mg, 8.08 mmol) followed by Pd/C (10% wt on activated carbon, 214.8 mg, 0.20 mmol). The reaction mixture is placed under nitrogen (balloon), and heated to 400° C. for 1 h. The reaction mixture is filtered and the filtrate is concentrated. The residue is dissolved in EtOAc, washed with water and brine and filtered using a phase separator. The solvent is evaporated and purification by Combiflash (40% EtOAc/Hex) affords 11a3.

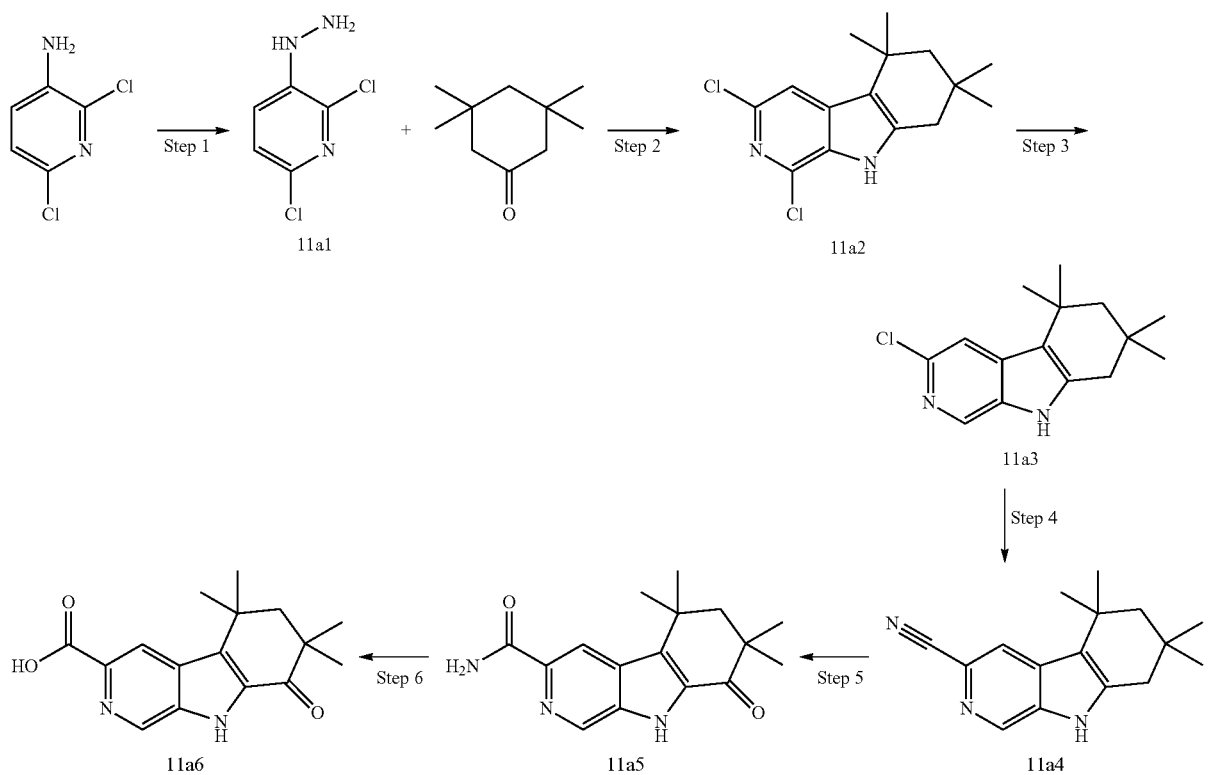

Step 1:

To a solution of 3-amino-2,6-dichloropyridine (10 g, 61.3 mmol, TCI-US) in 6N HCl (68.5 mL) at 00° C. is added a solution of sodium nitrite (4.23 g, 61.3 mmol) in water (33.3 mL). After 30 min at 00° C., a solution of SnCl$_2$.2H$_2$O (34.75 g, 154.0 mmol) in 6N HCl (69 mL) is added at 0° C. The resulting mixture is stirred for 3 h at 0° C. and then is allowed to warm to RT overnight. The reaction mixture is quenched by the addition of an aqueous solution of KOH (40% w/w, until the pH turns basic, ~70 mL). The crude material is extracted with EtOAc (6×). The organic layers are combined, dried over MgSO$_4$, filtered and concentrated under reduced pressure to give 11a1.

Step 2:

To a solution of 11a1 (9.2 g, 51.7 mmol) in NMP (42 mL) is added 3,3,5,5-tetramethylcyclohexanone (9.84 mL, 56.8 mmol, Aldrich). The resulting mixture is stirred for 1 h at 80° C. Pyridine hydrochloride is added (17.9 g, 155.0 mmol) and the resulting mixture is stirred at 160° C. for 5 h. The reaction mixture is allowed to cool to RT, then diluted with EtOAc (1 L), washed with 1N HCl (6×) and brine, dried over MgSO$_4$, filtered and the solvent is evaporated. Purification by Combiflash (10% EtOAc/Hex) affords 11a2.

Step 4:

To a solution of 11a3 (54 mg, 0.20 mmol) in anhydrous DMAc (4 mL) in a microwave vial are added zinc cyanide (54 mg, 0.46 mmol) and bis-tributylphosphine palladium(0) (53.6 mg, 0.10 mmol). The vial is capped and submitted to microwave conditions (Biotage Initiator Sixty; Vial: 2-5 mL; Pre-stirring: 10 sec; Absorption level: High; Run time: 20 min; temperature: 1400° C.). EtOAc (100 mL) is added and the mixture is washed with water (3×) to afford crude 11a4 which is used as is for the next step.

Step 5:

11a4 (72 mg, 0.21 mmol) and MnO$_2$ (400 mg, 4.60 mmol) are dissolved in AcOH (3.6 mL) and heated to 100° C. After 1 h, another portion of MnO$_2$ (150 mg, 1.73 mmol) is added. After 15 min, the reaction mixture is allowed to cool to RT, then filtered through Celite with EtOAc washing. The filtrate is evaporated to dryness (with an azetropic removal of AcOH with PhMe) to afford 11a5 that is used as such for the next step.

Step 6:

11a5 (104 mg, 0.20 mmol) is dissolved in EtOH (1 mL), treated with 10N NaOH (0.2 mL, 2.0 mmol) and then heated to 100° C. overnight. The reaction mixture is allowed to cool to RT and quenched with 4N HCl/dioxane (until acidic pH) and evaporated to dryness to afford 11a6 that is used as is in subsequent reactions.
Example 12
Preparation of Intermediate 12a10
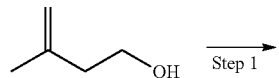
Step 1
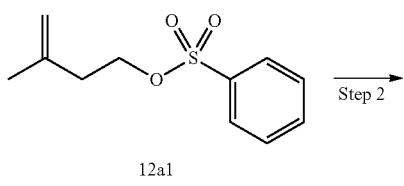
12a1
Step 2
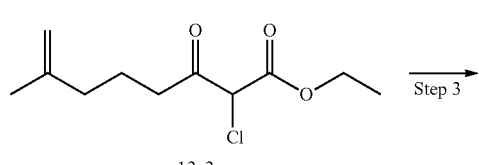
12a2
Step 3
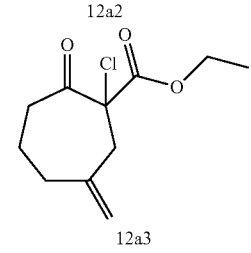
12a3
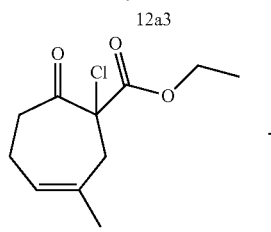
12b3
Step 4
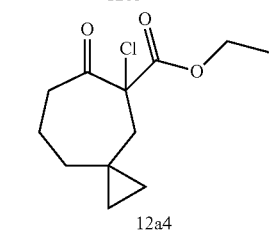
12a4
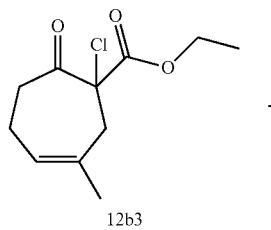
12b3
Step 5
-continued
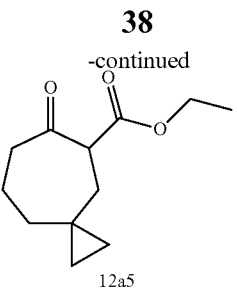
12a5
+
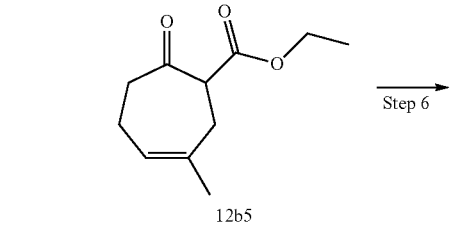
12b5
Step 6
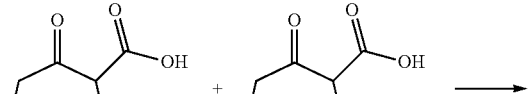
12a6       12b6
Step 7
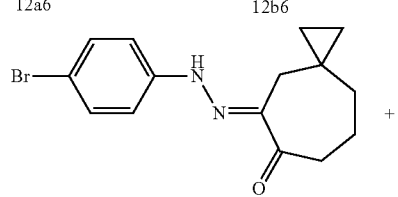
12a7
+
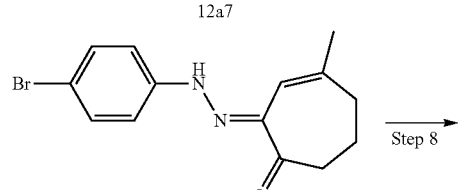
12b7
Step 8
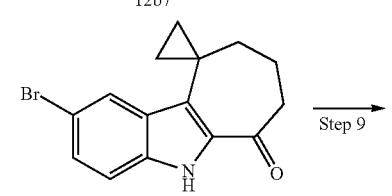
12a8
Step 9
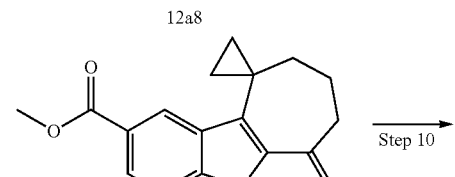
12a9
Step 10

-continued

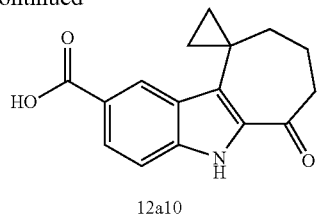

12a10

Step 1:

To a solution of 3-methyl-3-buten-1-ol (2.36 g, 27.4 mmol, Aldrich) in DCM (25.00 mL) is added TEA (7.64 mL, 54.8 mmol) and DMAP (420.0 mg, 3.44 mmol). The solution is cooled to 0° C. and benzenesulfonyl chloride (5.32 g, 30.1 mmol) is added over a period of 20 min. After warming the reaction mixture to RT and stirring for 4 h, the reaction mixture is filtered. The solution is concentrated under reduced pressure and the crude residue is passed through a silica gel plug and washed with 20% EtOAc/Hex. The filtrate is concentrated to afford 12a1 which is used as is in the next reaction.

Step 2:

NaH (60% suspension in oil, 425.1 mg, 10.6 mmol) is weighed into a flask and suspended in THF (60.00 mL). The flask is cooled in an ice bath. Ethyl 2-chloroacetoacetate (1.45 g, 8.83 mmol) is added and the resulting mixture is stirred at 0° C. for 10 min. n-Butyl lithium (1.6M in THF, 6.08 mL, 9.72 mmol) is added to the reaction mixture over a period of 5 min. The reaction mixture is cooled to −40° C., then 12a1 (2.00 g, 8.84 mmol) is added. The resulting solution is stirred for 1 h at 0° C., and then stirred at RT for 2 h. The reaction mixture is diluted with Et$_2$O and acidified with 1N HCl. The organic layer is separated, washed with saturated NaHCO$_3$, washed with brine, dried over MgSO$_4$, filtered, concentrated under reduced pressure and purified by Combiflash (Hex/EtOAc) to give 12a2.

Step 3:

To a stirred mixture of manganese(III) acetate dihydrate (3.23 g, 12.05 mmol) and copper(II) acetate hydrate (1.20 g, 6.02 mmol) in AcOH (50.00 mL) is added 12a2 (1.40 g, 6.02 mmol) in AcOH (4 mL). The reaction mixture is stirred at RT for 18 h. Water (30 mL) is added, followed by the addition of a 10% solution of NaHSO$_3$. The resulting mixture is extracted with DCM. The combined organic layers are washed with saturated NaHCO$_3$, dried over MgSO$_4$, filtered, concentrated under reduced pressure and purified by Combiflash (Hex/EtOAc) to provide 12a3+12b3.

Step 4:

To a solution of 12a3+12b3 (600 mg, 2.60 mmol) in Et$_2$O (8.00 mL, 76.20 mmol) is added diazomethane in Et$_2$O (0.60 M in Et$_2$O, 4.5 L). The solution is cooled to 0° C. and palladium acetate (116.8 mg, 0.52 mmol) is added portionwise. Diazomethane (0.60 M in Et$_2$O, 9 mL) is added and the reaction mixture is stirred at RT for 2 h. When the reaction is complete, as indicated by NMR, the solution is filtered and concentrated under vacuum to afford crude 12a4+12b3 which is used in the next step as is.

Step 5:

To a stirred solution of the mixture 12a4+12b3 (500 mg, 2.04 mmol) in AcOH (5.00 ml) is added zinc dust (200.4 mg, 3.06 mmol) at RT. The reaction mixture is stirred for 3 h at RT then filtered through Celite. The Celite pad is washed with DCM. The organic layer is transferred to a separatory funnel, washed with water, washed with saturated NaHCO$_3$, dried over MgSO$_4$, filtered and concentrated under reduced pressure. The residue is passed through a silica gel pad (Hex/EtOAc) to afford 12a5+12b5.

Step 6:

12a5+12b5 (516 mg, 2.45 mmol) is charged in a round bottom flask with water (10.00 mL) and 5N NaOH (0.614 mL, 3.07 mol), and the resulting mixture is stirred for 24 h. The reaction mixture is transferred to a separatory funnel, and washed with Et$_2$O (2×). The aqueous layer is transferred back to its original flask, cooled to 0° C. and quenched with 1 equivalent of HCl (until pH is about 4-5). The reaction mixture is stirred at 0° C. for 25 min to afford 12a6+12b6 that is used as is in the next step.

Step 7:

To 12a6+12b6 (447.0 mg, 2.45 mmol) in water (~30 mL) at 0° C. is added a solution of 4-bromobenzenediazonium tetrafluoroborate (664.4 mg, 2.45 mmol) in water (84 mL) over a period of 15-20 min. The resulting mixture is stirred at 0° C. for 10 min, and then allowed to stir at RT for 30 min. The reaction mixture is filtered and the residue is dissolved in EtOAc, washed with brine, dried over MgSO$_4$, filtered and concentrated under reduced pressure to afford 12a7+12b7 that is used as is in the next step.

Step 8:

12a7+12b7 (787 mg, 2.45 mmol) is suspended in MeCN (15.00 mL) and a 1.8M sulfuric acid solution (4.08 mL, 7.35 mmol) is added. The reaction mixture is stirred for 4 h at 80° C., then cooled to RT and concentrated under reduced pressure to remove approximately half of the MeCN. Water (50 mL) is added, and the reaction mixture is stirred for 1 h. The mixture is filtered and the residue is purified by Combiflash (100% Chloroform, then 5% MeOH/Chloroform) to obtain 12a8.

Step 9:

To a solution of 12a8 (197.0 mg, 0.65 mmol) in DMSO (10.00 mL) and MeOH (5.00 mL) is added TEA (0.48 mL, 3.41 mmol). The reaction mixture is purged with CO(g), followed by the addition of Pd(dppf)Cl$_2$-DCM adduct (61.4 mg, 0.08 mmol). The resulting solution is fitted with a condenser, purged with CO(g) and heated to 85° C. (under 1 atmosphere of CO(g)) for 8 h. The solution is cooled to RT and diluted with EtOAc. The organic phase is washed with water (3×), washed with brine, dried over Na$_2$SO$_4$, concentrated under reduced pressure and purified by Combiflash (DCM/MeOH, 100:0 to 95:5) to provide 12a9.

Example 13

(General Method A): Preparation of Intermediate 13a2

Example 13 is an example of a general method wherein the carboxylic partners, such as 3a2, are coupled with the appropriate Boc-protected partner, such as 13a0, followed by deprotection.

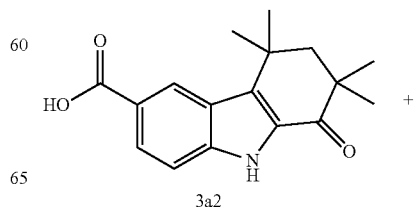

3a2

-continued

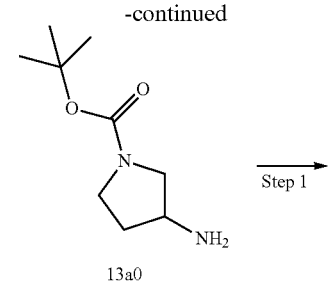
13a0

| Step 1

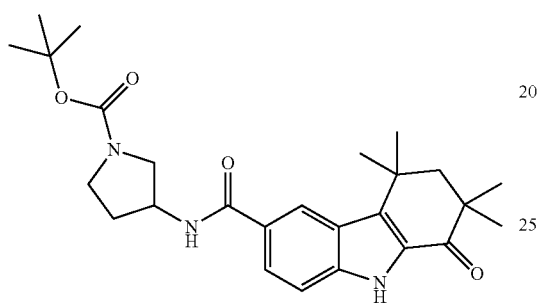
13a1

| Step 2

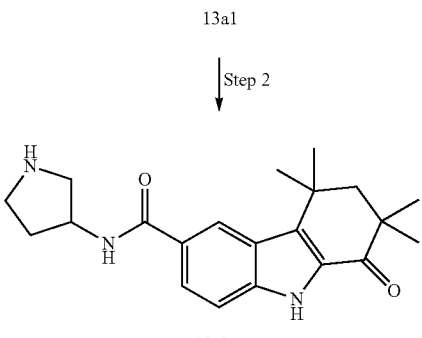
13a2

Step 1:

To a solution of 3a2 (500 mg, 1.75 mmol) and 13a0 (653 mg, 3.50 mmol, Chembridge) in DMF (10 mL) are added HATU (866 mg, 2.3 mmol) and DIPEA (1.2 mL, 7.0 mmol). The reaction mixture is stirred for 2 h at RT, quenched with AcOH (0.5 mL) and the resulting solution is diluted with water. The aqueous layer is extracted with EtOAc (3×). The organic layers are combined, washed with brine, dried over MgSO$_4$, filtered, concentrated and purified by Combiflash (30% EtOAc/Hex to 70% EtOAc/Hex) to isolate 13a1.

Step 2:

To a solution of 13a1 (795 mg, 1.8 mmol) in DCM (15 mL) is added TFA (8.5 mL, 110.3 mmol) and the resulting solution is stirred for 1 h. The reaction mixture is neutralized with a saturated aqueous solution of NaHCO$_3$ and extracted with EtOAc (3×). The organic layers are combined, washed with brine, dried with MgSO$_4$, filtered and concentrated to afford 13a2 which is used as is for subsequent reactions.

Intermediates 13b2 to 13o2 are made analogously to the procedure described in Example 13.

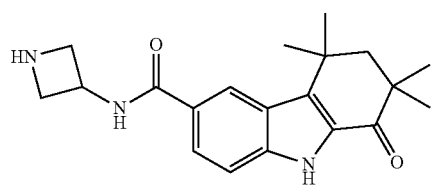
13b2

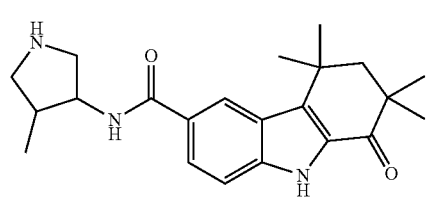
13c2

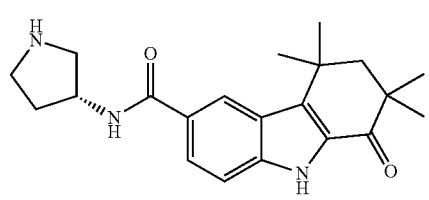
13d2

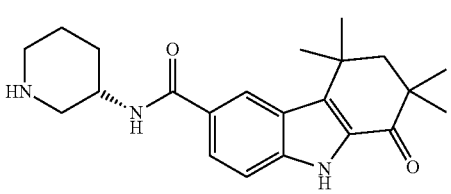
13e2

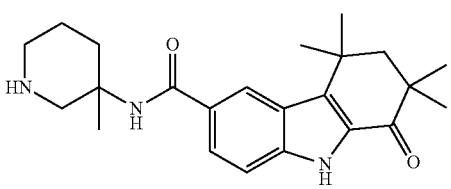
13f2

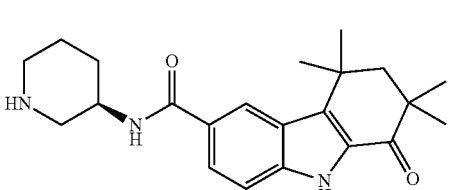
13g2

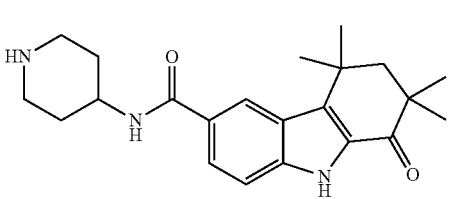
13h2

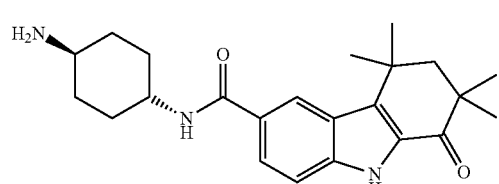
13i2 enantiomeric mixture of trans isomers

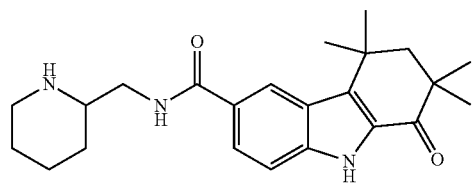
13j2

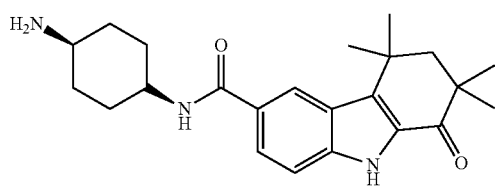
13k2 enantiomeric mixture of cis isomers

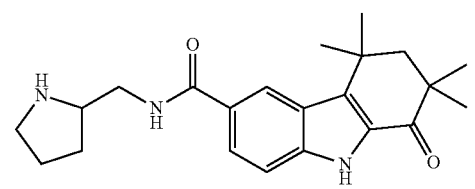
13l2

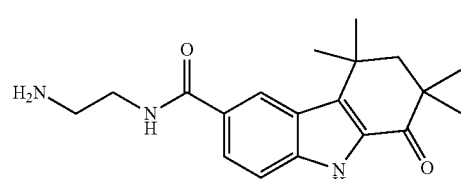
13m2

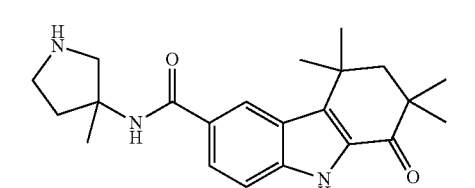
13n2

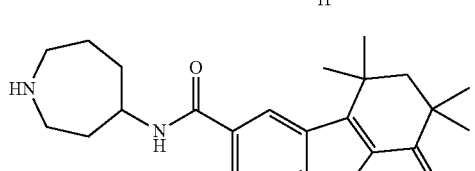
13o2

Example 14

(General Method B): Preparation of Compound 2026

Example 14 is an example of a general method wherein the intermediate (13a2 to 13o2) obtained in Example 13 (GENERAL METHOD A) is coupled with the suitable carboxylic acid partner.

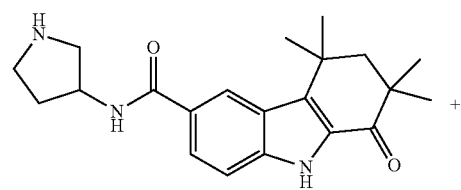
13a2

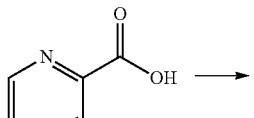
14a1

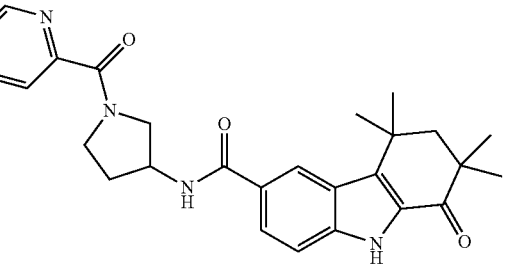
2026

To a solution of 14a1 (22 mg, 0.17 mmol, Aldrich) in DMF (1.0 mL) are added HATU (42 mg, 0.11 mmol) and DIPEA (60 µL, 0.34 mmol). The solution is stirred for 30 min, then 13a2 (30.0 mg, 0.08 mmol) is added. The reaction mixture is stirred for 2 h at RT, quenched with AcOH (0.2 mL) and purified by preparative RP-HPLC to provide compound 2026.

Example 15

Preparation of Compound 7015

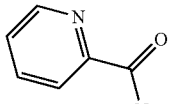

7015

To a solution of 3a2 (20.0 mg, 0.07 mmol) and 15a1 (12.2 mg, 0.14 mmol, Small-Molecule) in DMF (1 mL) are added HATU (34.6 mg, 0.09 mmol) and DIPEA (48.8 µL, 0.28 mmol). The reaction mixture is stirred for 2 h at RT, quenched with AcOH (0.1 mL) and purified by preparative RP-HPLC to provide compound 7015.

Example 16

Preparation of Intermediate 16a2

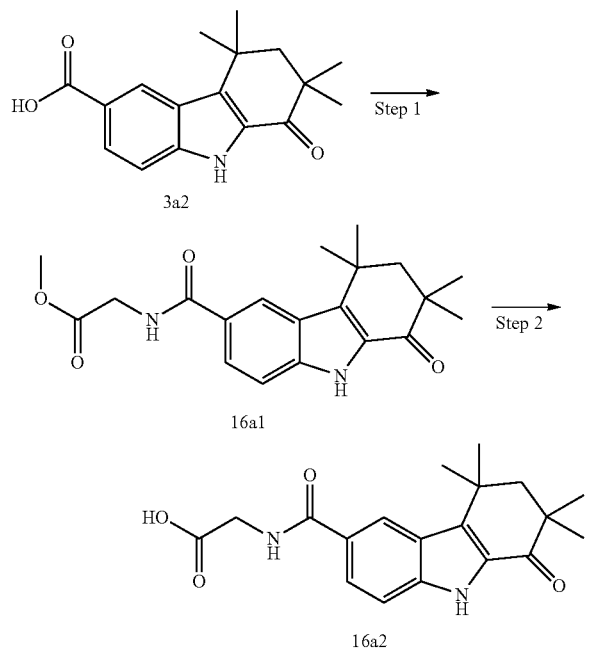

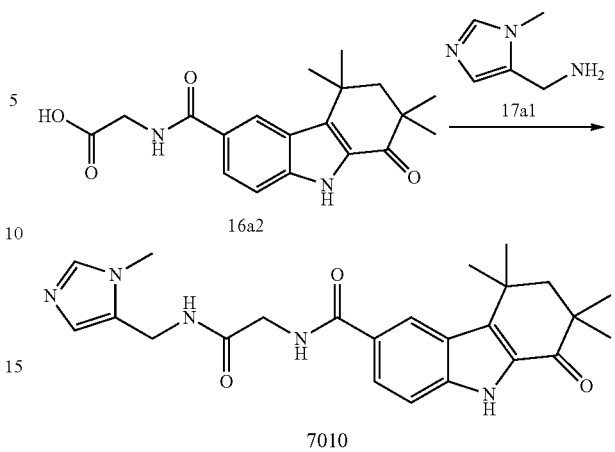

To a solution of 16a2 (20 mg, 0.06 mmol) and 17a1 (13 mg, 0.12 mmol, Chembridge) in DMF (1 mL) is added HATU (33 mg, 0.09 mmol) and DIPEA (45 μL, 0.32 mmol). The mixture is stirred for 2 h at RT, quenched with AcOH (0.1 mL) and purified by preparative RP-HPLC to provide compound 7010.

Example 18

(General Method D): Preparation of Compound 2003

Example 18 is an example of a general method wherein the intermediate obtained in Example 13 (General Method A) is alkylated.

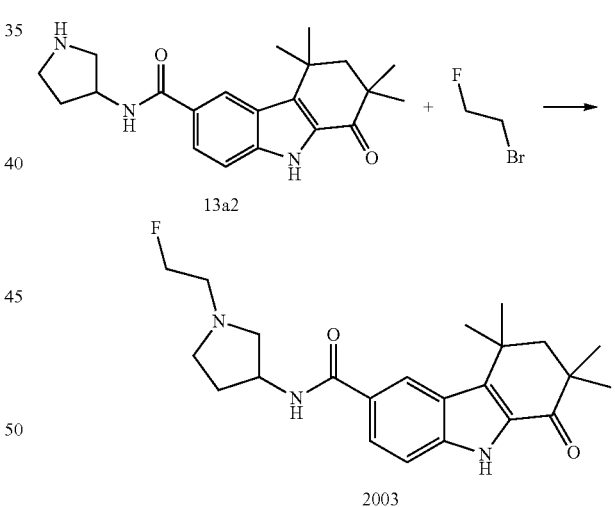

Step 1:

To a solution of 3a2 (400.0 mg, 1.40 mmol) in DMSO (5.00 mL) is added amino-acetic acid methyl ester (137.4 mg, 1.54 mmol, Princeton), TEA (293.1 mL, 2.10 mmol) and HATU (639.6 mg, 1.68 mmol). The reaction mixture is stirred at RT for 1 h, then quenched with a saturated solution of NaHCO$_3$ and extracted with EtOAc. The organic layers are combined, washed with brine, washed with a 0.5N solution of HCl, washed with brine, dried over MgSO$_4$, filtered and concentrated under reduced pressure. Purification by Combiflash (DCM/MeOH, 100:0 to 90:10) provides 16a1.

Step 2:

16a1 (351.0 mg, 0.99 mmol) is dissolved in MeOH (8.00 mL) and a 1N solution of NaOH (8.40 mL, 8.4 mmol) is added. The reaction mixture is stirred overnight at RT, quenched with 1 equivalent of 1N HCl (until pH 7.0) and concentrated almost to dryness under reduced pressure. Water is added and the residue is filtered to provide 16a2.

Example 17

(General Method C): Preparation of Compound 7010

Example 17 is an example of a general method wherein the intermediate 16a2 is coupled with the suitable amine.

To a solution of 13a2 (25 mg, 0.07 mmol) in MeCN (1.0 mL) are added TEA (39.4 μL, 0.28 mmol) followed by 1-bromo-2-fluoroethane (10.8 mg, 0.08 mmol, Amplachem). The reaction mixture is stirred at 60° C. overnight, quenched with AcOH (0.1 mL), diluted in DMSO/MeOH and purified by preparative RP-HPLC to give compound 2003.

Example 19

(General Method E): Preparation of Compound 2058

Example 19 is an example of a general method wherein the intermediate obtained in Example 13 (General Method A) is reacted with the suitable sulphonyl chloride reagent.

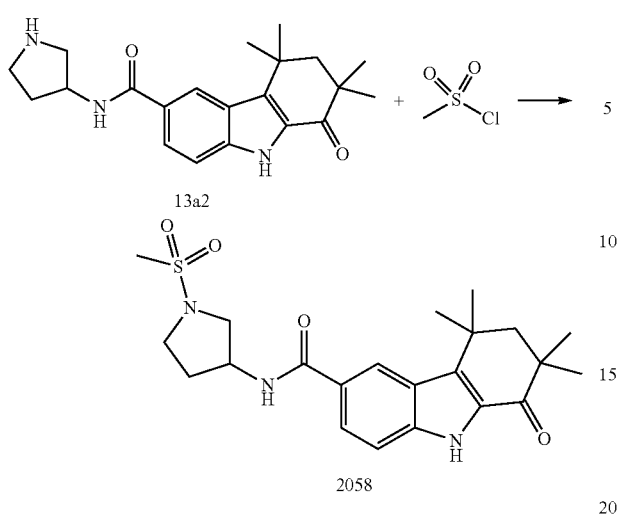

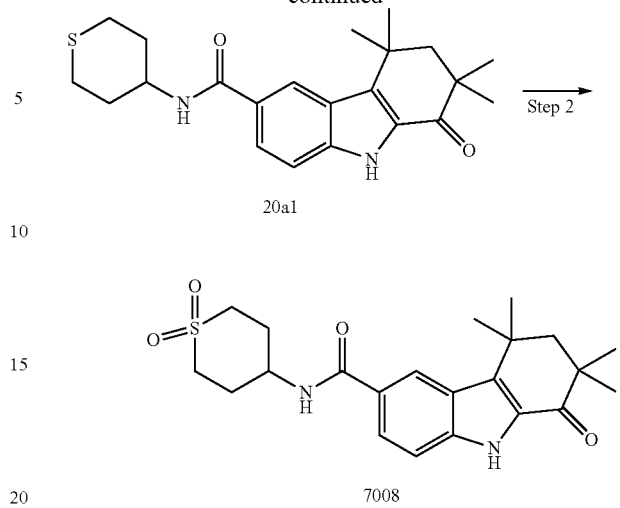

To a solution of 13a2 (25.0 mg, 0.07 mmol) in THF (1.0 mL) are added TEA (10.9 µL, 0.08 mmol) and methanesulfonyl chloride (6.0 µL, 0.08 mmol, Aldrich). The reaction mixture is stirred overnight at RT. TEA (10.9 µL, 0.08 mmol) and methanesulfonyl chloride (6.0 µL, 0.08 mmol) are added to the reaction mixture that is then stirred for 2 h. The reaction mixture is concentrated to dryness, diluted in DMSO/MeOH and purified by preparative RP-HPLC to provide compound 2058.

Example 20

Preparation of Compound 7008

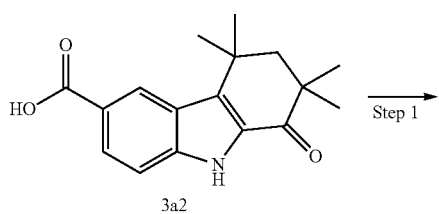

Step 1:

To a solution of 3a2 (46.5 mg, 0.16 mmol) in DMSO (2.00 mL) is added tetrahydrothiopyran-4-ylamine (21.0 mg, 0.18 mmol, Frontier), TEA (34.1 µL, 0.24 mmol) and HATU (74.4 mg, 0.20 mmol). The reaction mixture is stirred at RT for 1 h, quenched with a saturated aqueous solution of NaHCO$_3$ and extracted with EtOAc. The organic layers are combined, washed with brine (2×), dried over MgSO$_4$, filtered and concentrated under reduced pressure to provide crude 20a1.

Step 2:

To a solution of 20a1 (60.0 mg, 0.16 mmol) in MeOH (3.00 mL) is added a solution of Oxone (143.9 mg, 0.23 mmol) in water (1.50 mL). The reaction mixture is stirred at RT for 10 h. Water is added, and the reaction mixture is extracted with DCM. The organic layers are combined, washed with water (2×), washed with brine, dried over MgSO$_4$, filtered and concentrated under reduced pressure. Purification by preparative RP-HPLC affords compound 7008.

Example 21

Preparation of Compound 2007

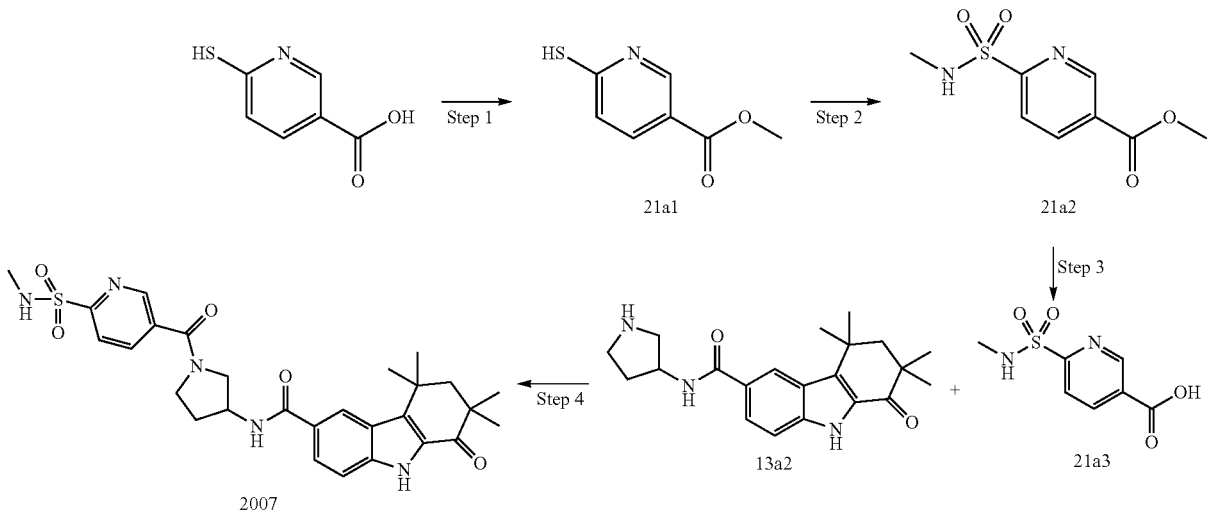

Step 1:

TMS-diazomethane (2M in Et$_2$O, 1.8 mL, 3.5 mmol) is added to a solution of 6-mercaptonicotinic acid (500 mg, 3.2 mmol, Aldrich) in Et$_2$O (30 mL). The reaction mixture is stirred for 1 h then the solvent is removed in vacuo. Purification by Combiflash (100% DCM to 10% MeOH/DCM) affords 21a1.

Step 2:

21a1 (50.0 mg, 0.3 mmol) is added to DCM (1.5 mL) and 1N HCl (1.5 mL) in a 25 mL Erlenmeyer flask over 10 min at −10 to −5° C. (internal temperature). A cold (~5° C.) solution of sodium hypochlorite (6% in water) is added with stirring, maintaining the internal temperature at −10 to −5° C. The reaction mixture is stirred for 15 min at this temperature, and then transferred to a separatory funnel (pre-cooled with ice water). The DCM layer is separated and collected in a clean 50 mL Erlenmeyer flask cooled in a dry ice-acetone bath. Methylamine (2.0 M/THF, 0.37 mL, 0.739 mmol) is added with stirring. The flask is removed to an ice-water bath and the reaction mixture is stirred for 2 h at 0° C., washed with 1M phosphoric acid, water and brine. The organic layer is dried with MgSO$_4$, filtered, concentrated, and purified by Combiflash (100% DCM to 10% MeOH/DCM) to provide 21a2.

Step 3:

To 21a2 (12.5 mg, 0.05 mmol) in DMSO (1.0 mL) is added 1N NaOH (0.22 mL, 0.22 mmol). The reaction mixture is stirred at RT for 2 h. The mixture is acidified with 1N HCl (~0.1 mL) and extracted with EtOAc (3×). The organic extracts are combined, washed with brine, dried over MgSO$_4$, filtered and concentrated to provide 21a3.

Step 4:

21a3 is reacted with 13a2 using a procedure analogous to that described in Example 14 (General Method B) to provide compound 2007.

Example 22

Preparation of Compound 2036

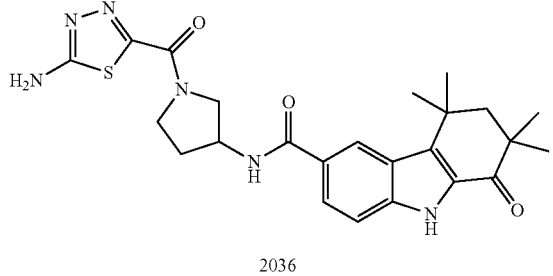

2036

Step 1:

To a solution of 22a1 (100 mg, 0.6 mmol, Oakwood) in DMSO (3.0 mL) is added 1N NaOH (3.5 mL, 3.5 mmol). The resulting mixture is stirred at RT overnight, then acidified with 1N HCl (~1.5 mL) and extracted with EtOAc (3×). The organic extracts are combined, washed with brine, dried over MgSO$_4$, filtered and concentrated to provide 22a2.

Step 2:

22a2 is reacted with 13a2 using a procedure analogous to that described in Example 14 (General Method B) to provide compound 2036.

Example 23

Preparation of Compound 2023

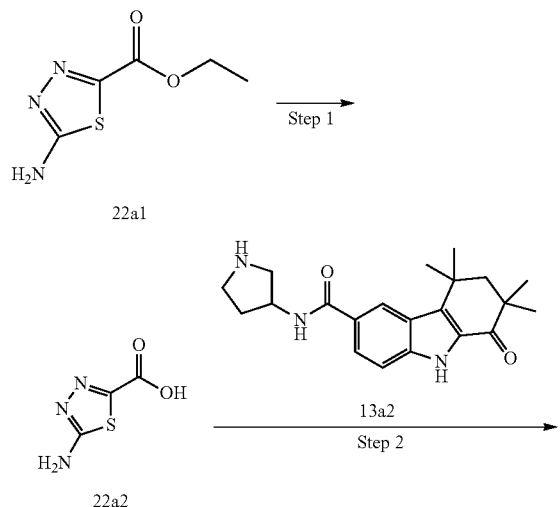

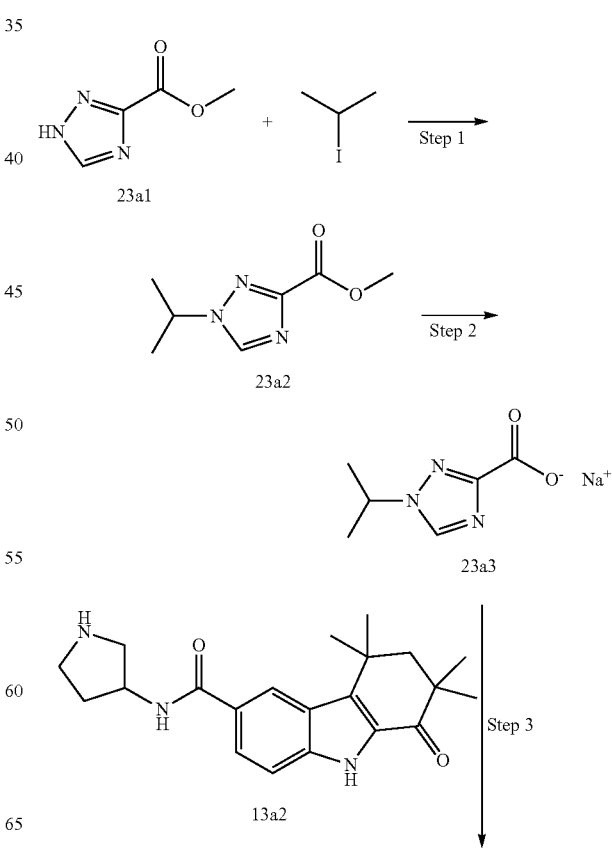

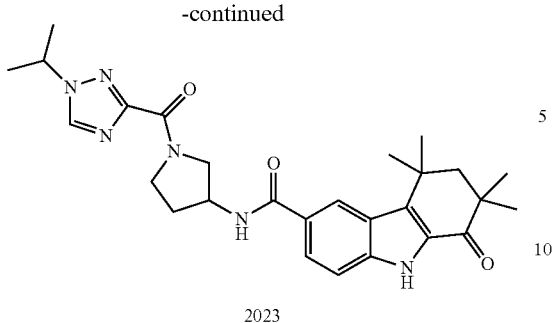

2023

Step 1:

To a solution of 23a1 (500 mg, 3.9 mmol, Aldrich) in DMF (7.5 mL) are added $K_2CO_3$ (598 mg, 4.3 mmol) and 2-iodopropane (0.79 mL, 7.9 mmol). The reaction mixture is stirred at RT for 3 days then quenched with 1N HCl until ~pH=5. The resulting solution is extracted with EtOAc (5×) and a 10% solution of MeOH in DCM (2×). The combined organic layers are washed with brine, dried with $MgSO_4$, filtered and concentrated. The crude mixture is diluted in DMSO/MeOH and purified by preparative RP-HPLC to provide 23a2.

Step 2:

To a solution of 23a2 (317 mg, 1.9 mmol) in THF (4.7 mL) and MeOH (1.6 mL) is added a 1N solution of NaOH (3.0 mL, 3.0 mmol). The reaction mixture is stirred for 1 h at RT. The solvent is evaporated in vacuo and the crude product purified by preparative RP-HPLC to provide 23a3.

Step 3:

23a2 is reacted with 13a2 using a procedure analogous to that described in Example 14 (General Method B) to provide compound 2023.

Example 24

Preparation of Compound 6003

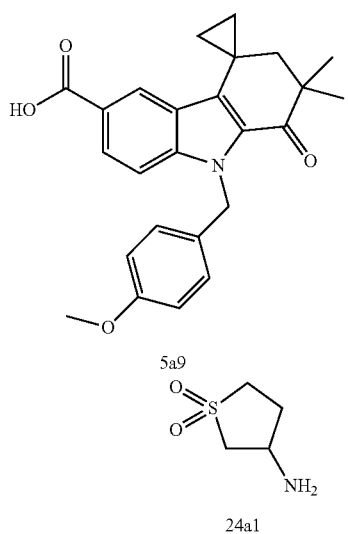

5a9

24a1

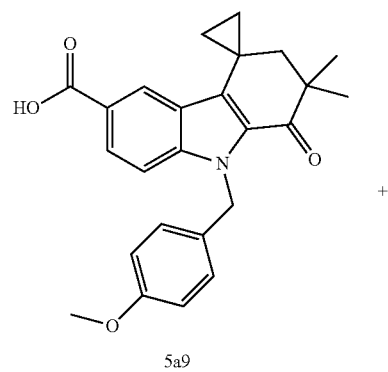

24a2

↓ step 2

6003

Step 1:

A solution of 24a1 (26 mg, 0.15 mmol, Intermed) and TEA (0.072 mL, 0.51 mmol) in DMSO (1 mL) is added to a solution of 5a9 (41 mg, 0.10 mmol) and HATU (45 mg, 0.12 mmol) in DMSO (0.5 mL). The resulting solution is stirred at RT overnight. The reaction mixture is diluted with EtOAc, washed with an aqueous solution of saturated $NaHCO_3$, $H_2O$ (2×) and brine, dried over $MgSO_4$, filtered and concentrated to afford 24a2.

Step 2:

A solution of 24a2 (52 mg, 0.10 mmol) in DCM (2 mL) is treated with TFA (1 mL). The resulting solution is stirred for 4 h at RT and then the solvent is evaporated in vacuo. The residue is dissolved in DMSO, filtered and purified by preparative RP-HPLC to provide compound 6003.

Example 25

Preparation of Compound 6001

5a9

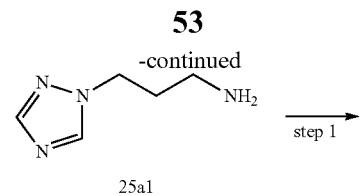

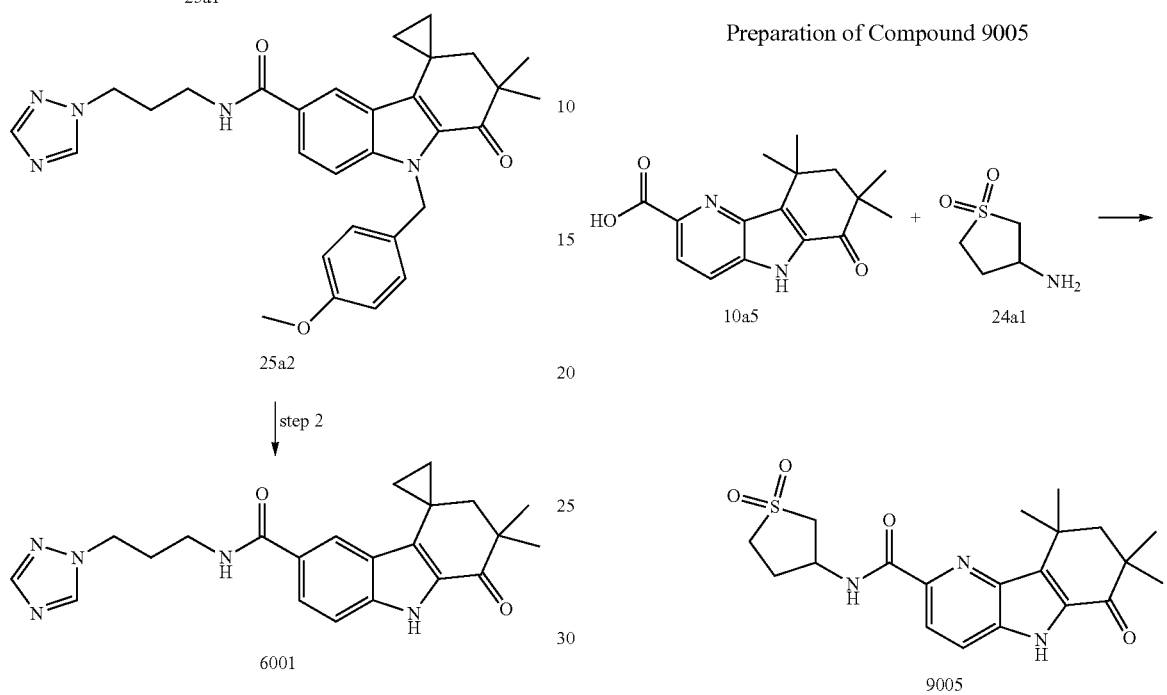

Step 1:

5a9 is reacted with 25a1 (Enamine) using a procedure analogous to that described in Example 24, Step 1 to provide 25a2.

Step 2:

6001 is obtained from 25a2 using a procedure analogous to that described in Example 24, Step 2.

Example 26

Preparation of Compound 5003

6a4 is coupled with 24a1 using a procedure analogous to that described in Example 15 to provide compound 5003.

Example 27

Preparation of Compound 9005

10a5 is coupled with 24a1 using a procedure analogous to that described in Example 15 to provide compound 9005.

Example 28

Preparation of Compound 9004

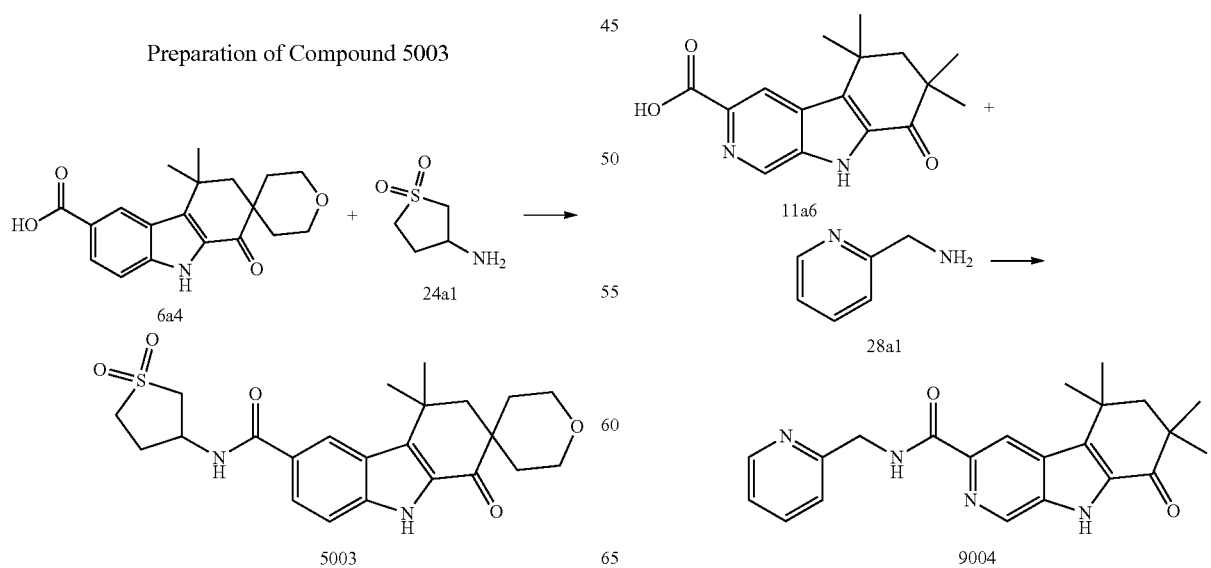

11a6 is coupled with 28a1 (Aldrich) using a procedure analogous to that described in Example 15 to provide compound 9004.

Example 29

Preparation of Intermediate 29a2

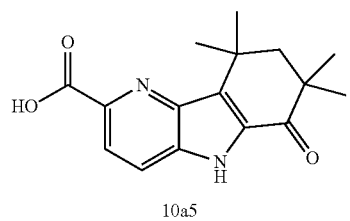

10a5

+

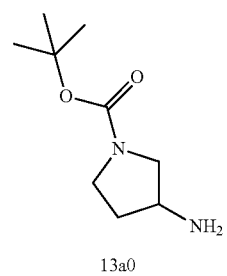

13a0

Step 1

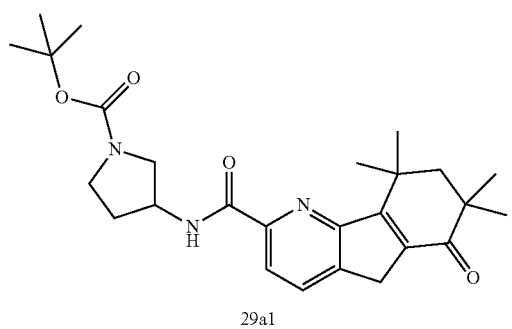

29a1

Step 2

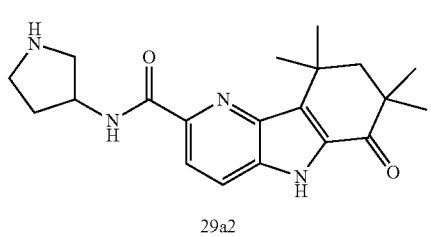

29a2

10a5 is coupled with 13a0 (step 1), followed by deprotection (step 2) using a procedure analogous to that described in Example 13 to afford intermediate 29a2.

Example 30

Preparation of Compound 9002

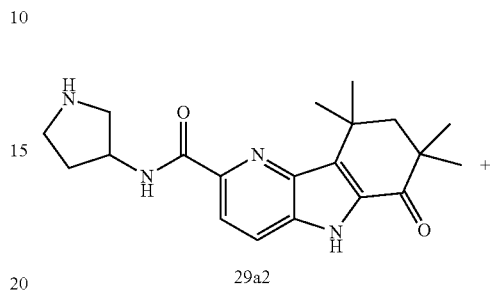

29a2

+

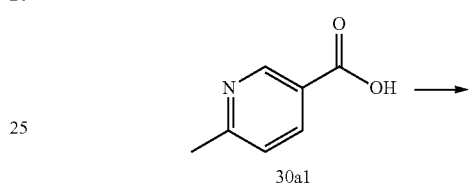

30a1

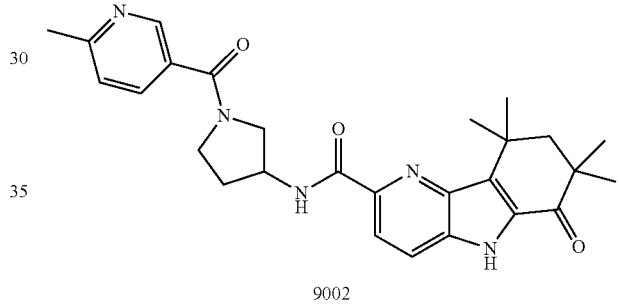

9002

29a2 is coupled with 30a1 (Aldrich) using a procedure analogous to that described in Example 14 to afford compound 9002.

Example 31

Preparation of Compound 5006

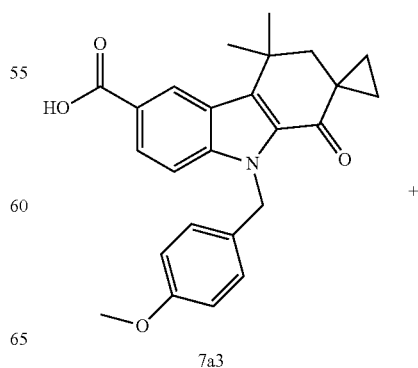

7a3

+

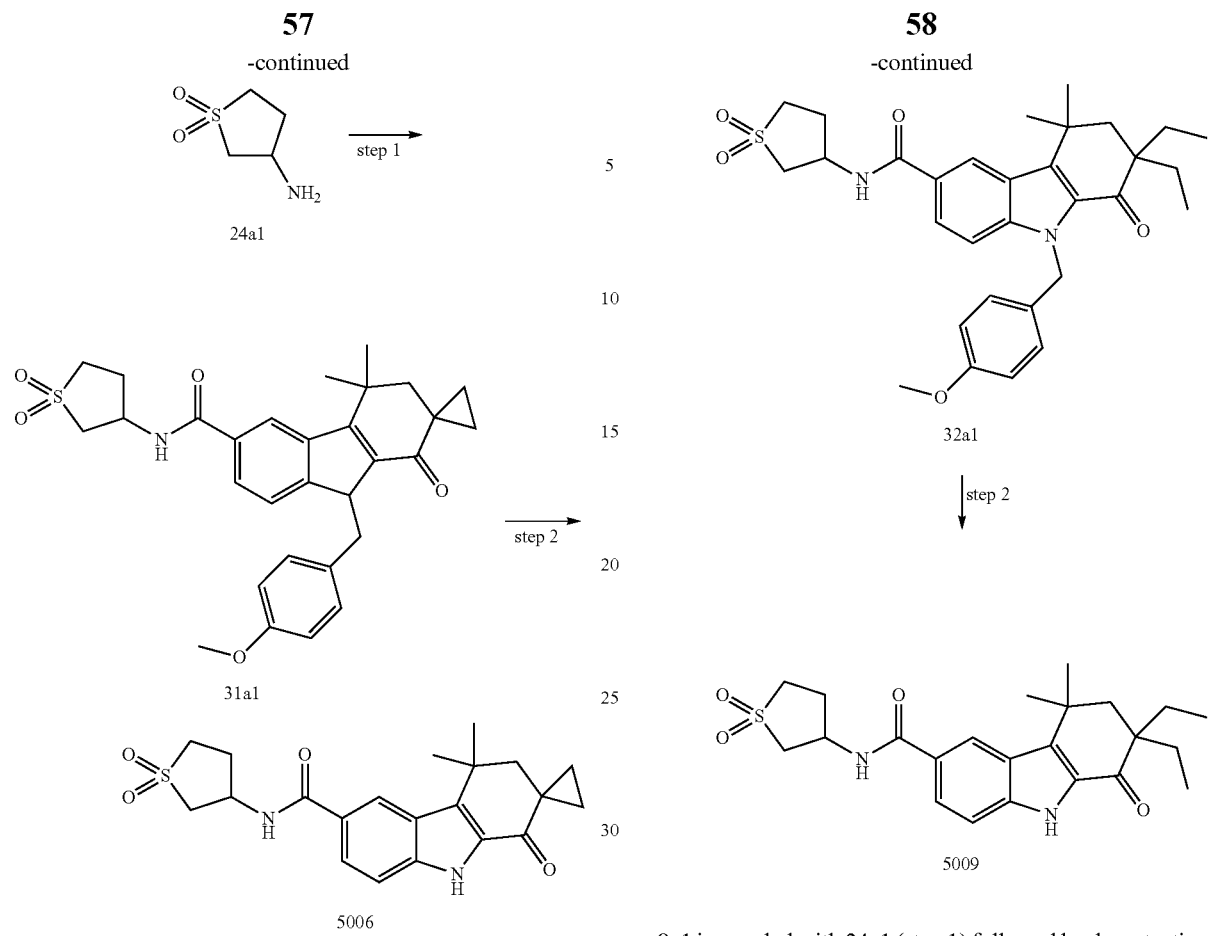
7a3 is coupled with 24a1 (step 1) followed by deprotection (step 2) using a procedure analogous to that described in Example 24 to provide compound 5006.
Example 32
Preparation of Compound 5009
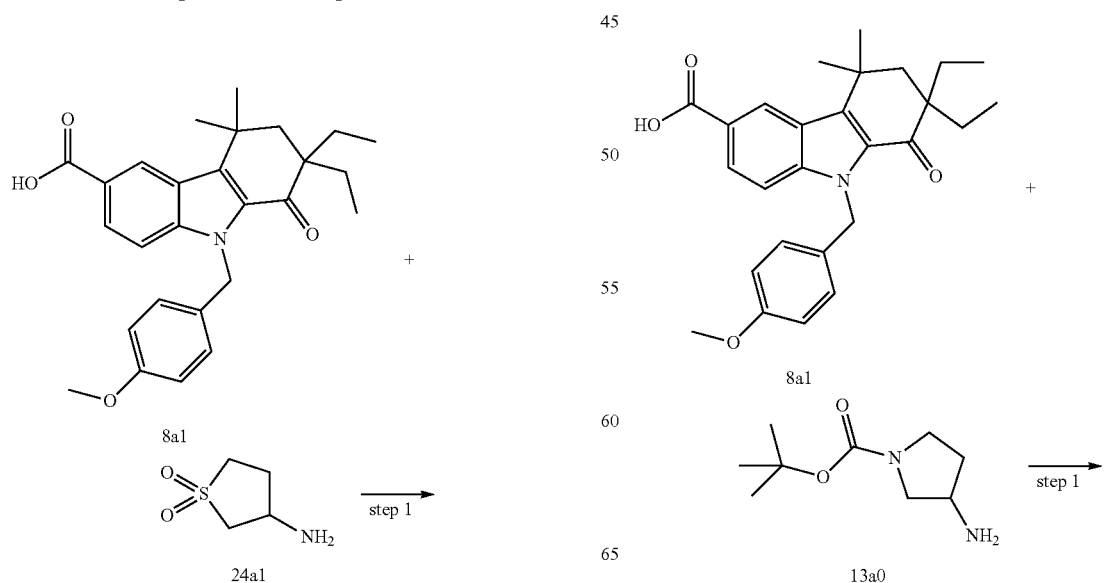
8a1 is coupled with 24a1 (step 1) followed by deprotection (step 2) using a procedure analogous to that described in Example 24 to provide compound 5009.
Example 33
Preparation of Intermediate 33a2

-continued

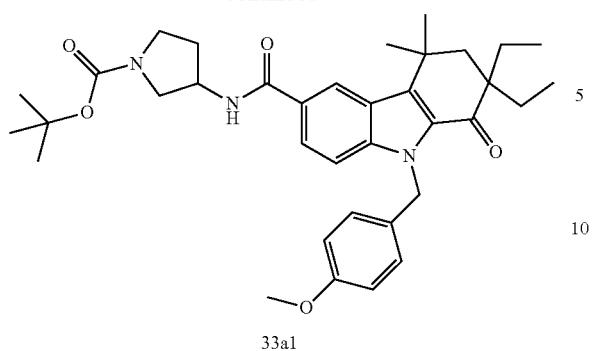

33a1

↓ step 2

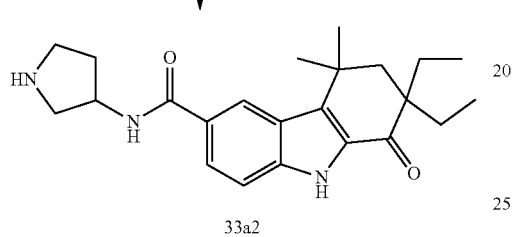

33a2

Step 1:

A solution of 13a0 (118 mg, 0.63 mmol) and TEA (0.44 mL, 3.16 mmol) in DMSO (1.5 mL) is added to a solution of 8a1 (275 mg, 0.63 mmol) and HATU (241 mg, 0.63 mmol) in DMSO (1.5 mL). The resulting solution is stirred for 3 h at RT. The reaction mixture is diluted with EtOAc and washed with an aqueous solution of saturated $NaHCO_3$, $H_2O$ (2×) and brine, dried over $MgSO_4$, filtered, concentrated and purified by Combiflash (60:40 Hex/EtOAc) to afford 33a1.

Step 2:

A solution of 33a1 (207 mg, 0.34 mmol) in DCM (2 mL) is treated with TFA (1 mL). The resulting solution is stirred for 7 h at RT. The solvent is evaporated in vacuo to provide 33a2.

Example 34

Preparation of Compound 5010

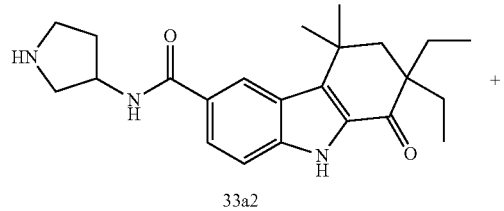

33a2

+

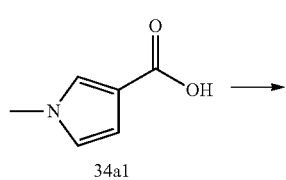

34a1

-continued

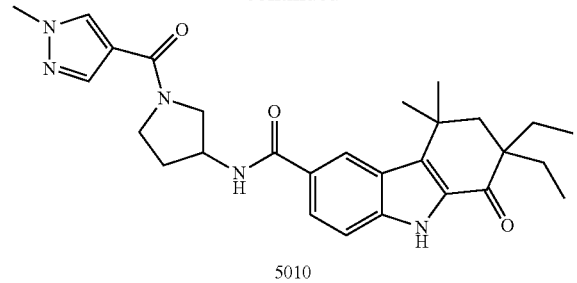

5010

33a2 is coupled with 34a1 (Aldrich) using a procedure analogous to that described in Example 14 to provide compound 5010.

Example 35

Preparation of Intermediate 35a2

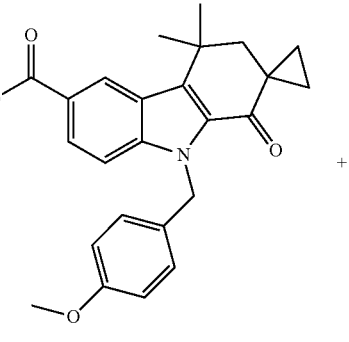

7a3

+

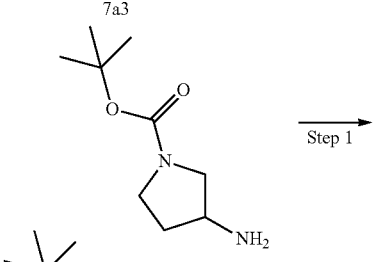

13a0

Step 1 →

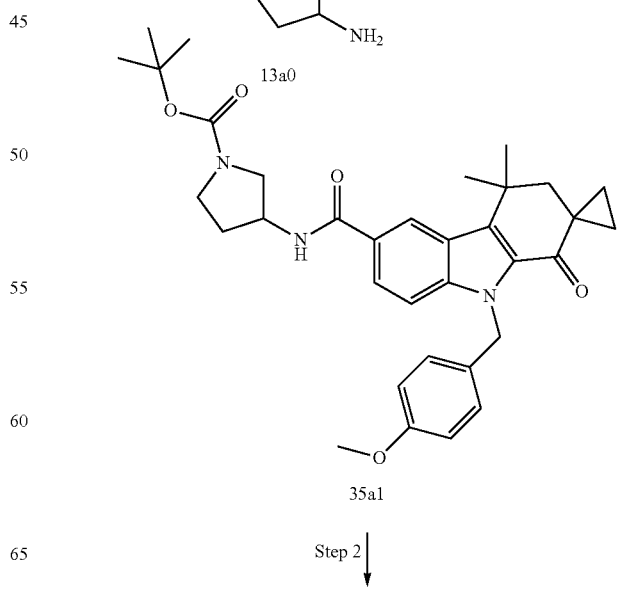

35a1

Step 2 ↓

-continued

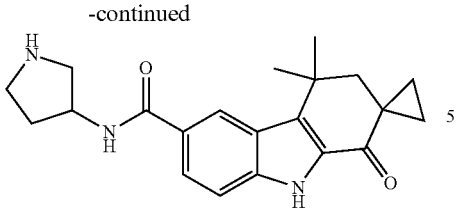
35a2

7a3 is coupled with 13a0 (step 1), followed by deprotection (step 2) using a procedure analogous to that described in Example 33 to afford intermediate 35a2.

Example 36

Preparation of Compound 5008

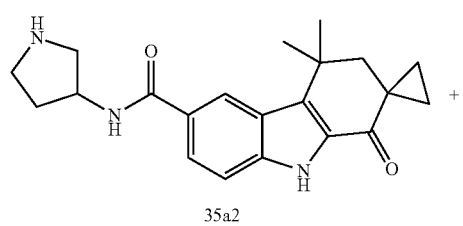
35a2

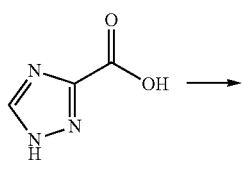
36a1

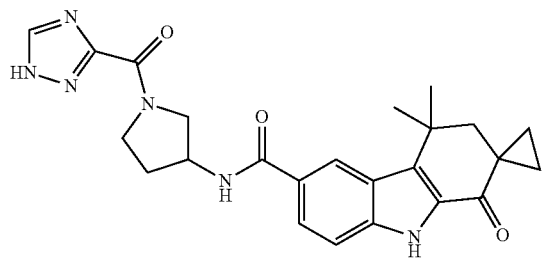
5008

35a2 is coupled with 36a1 (Aldrich) using a procedure analogous to that described in Example 14 to afford compound 5008.

Example 37

Preparation of Compound 6009

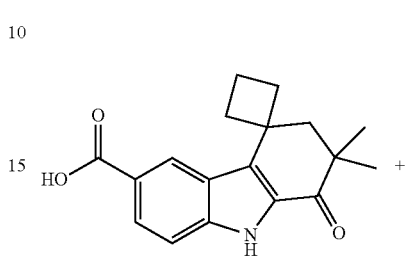
4a13

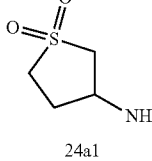
24a1

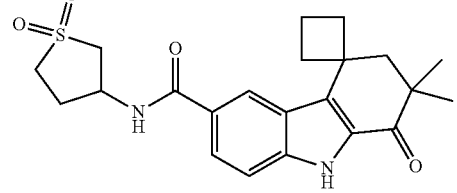
6009

4a13 is coupled with 24a1 using a procedure analogous to that described in Example 15 to provide compound 6009.

Example 38

Preparation of Intermediate 38a2

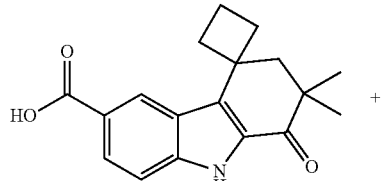
4a13

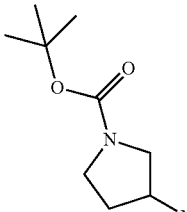
13a0

Step 1

63
-continued
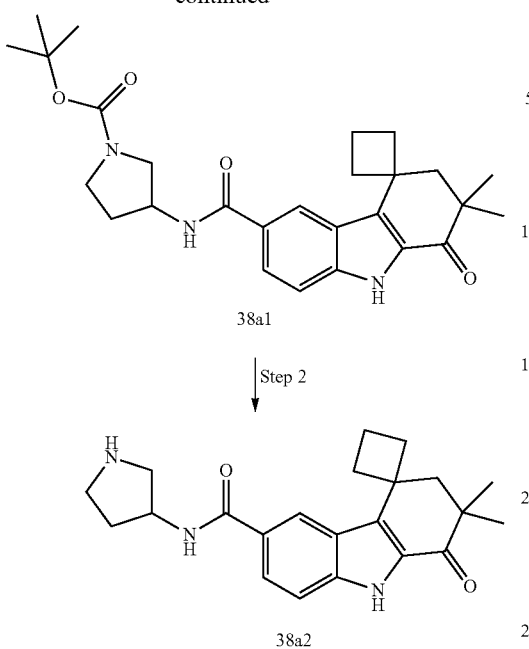
4a13 is coupled with 13a0 (step 1), followed by deprotection (step 2) using a procedure analogous to that described in Example 13 to provide intermediate 38a2.
Example 39
Preparation of Compound 6016
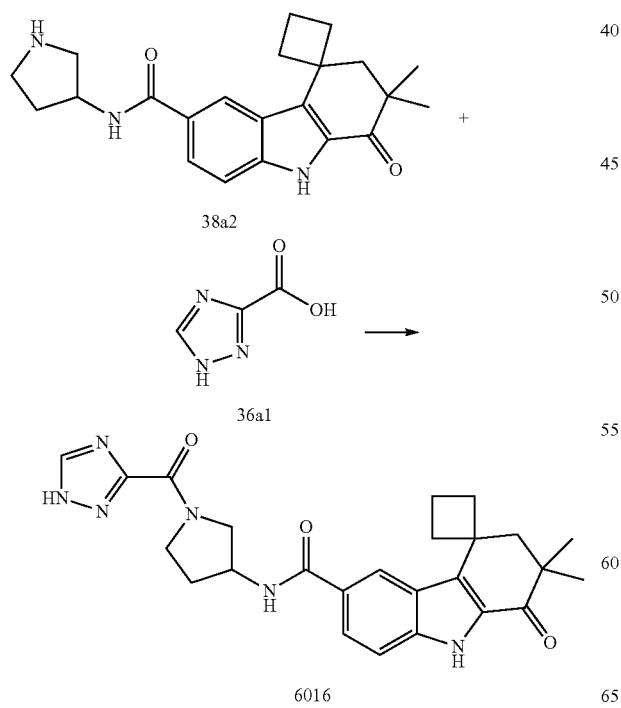
64
38a2 is coupled with 36a1 using a procedure analogous to that described in Example 14 to provide compound 6016.
Example 40
Preparation of Intermediate 40a3
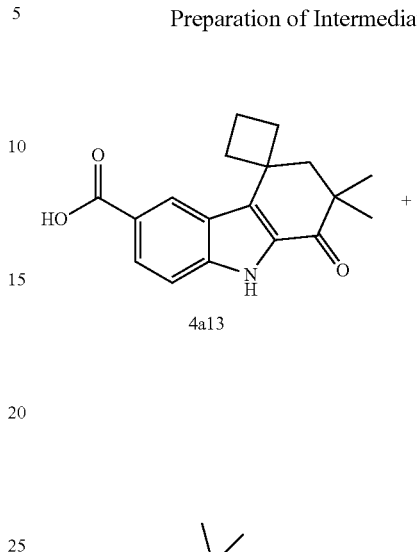
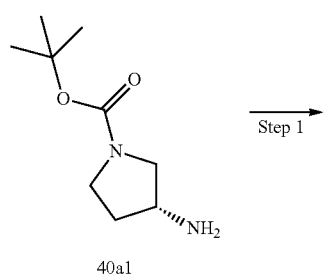
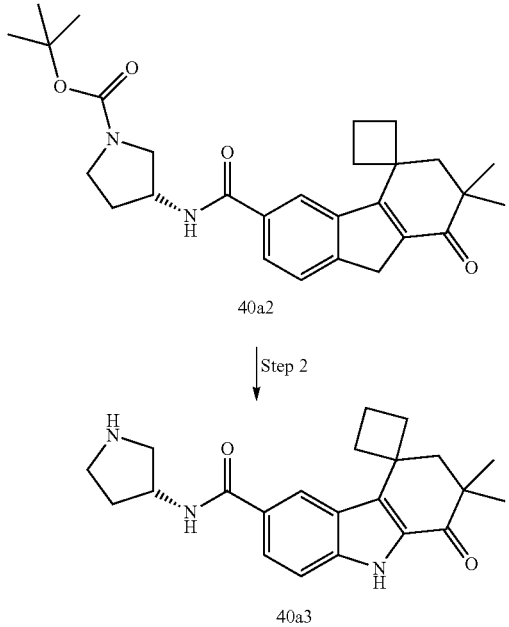

4a13 is coupled with 40a1 (Oakwood) (step 1), followed by deprotection (step 2) using a procedure analogous to that described in Example 13 to provide intermediate 40a3.

Example 41

Preparation of Compound 6004

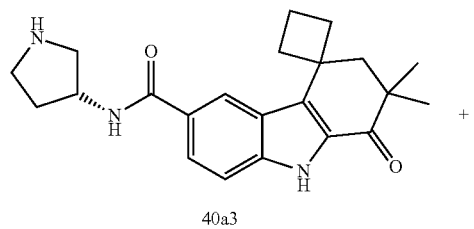
40a3

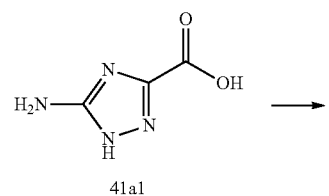
41a1

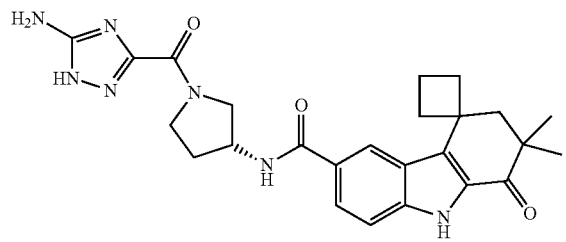
6004

40a3 is coupled with 41a1 (VWR) using a procedure analogous to that described in Example 14 to provide compound 6004.

Example 42

Preparation of Compound 7019

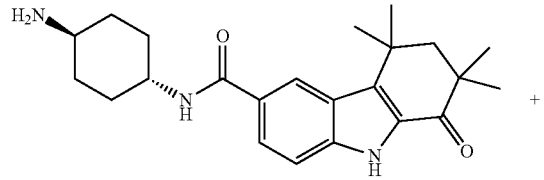
13i2

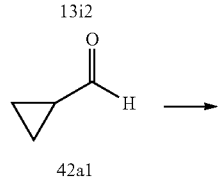
42a1

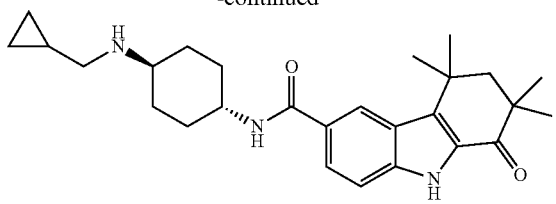
7019

AcOH (0.006 mL, 0.11 mmol) is added to a solution of 13i2 (25 mg, 0.07 mmol) and 42a1 (6.5 mg, 0.09 mmol, Aldrich) in DMF (1 mL). The resulting solution is stirred for 1 h at RT before adding sodium triacetoxyborohydride (69 mg, 0.33 mmol). After a period of 3 h, the reaction mixture is diluted with EtOAc, washed with an aqueous solution of saturated NaHCO$_3$ and H$_2$O (2×). The organic layer is dried over MgSO$_4$, filtered and concentrated under reduced pressure. The residue is dissolved in DMSO, filtered and purified by preparative RP-HPLC to give compound 7019.

Example 43

Preparation of Compound 3006

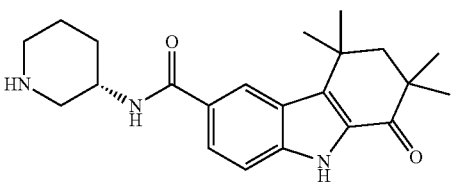
13e2

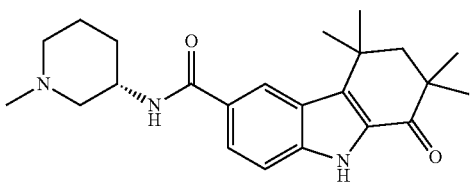
3006

To a solution of 13e2 (40.0 mg, 0.08 mmol) in DCM (1.00 mL), is added AcOH (0.10 mL) and formaldehyde (37% in aqueous solution, 16.9 μL, 0.21 mmol). The reaction mixture is stirred for 1 h at RT. Sodium triacetoxyborohydride (26.4 mg, 0.13 mmol) is added, and the solution is stirred for 2 h. DCM (30 mL) is added and the reaction mixture is washed with aqueous saturated NaHCO$_3$ and brine, then dried over

Example 44

Preparation of Compound 1103

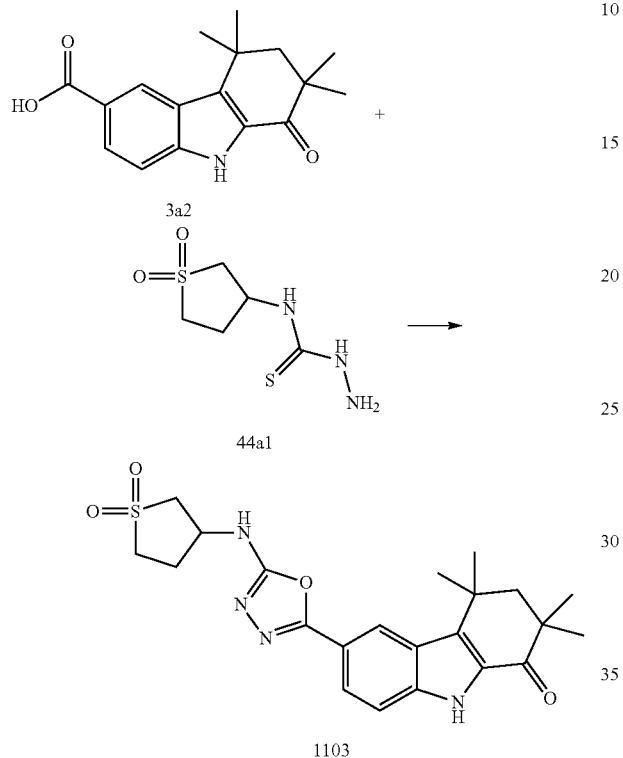

EDCI (150 mg, 0.78 mmol) is added to a solution of 44a1 (36 mg, 0.18 mmol, Princeton) and 3a2 (50 mg, 0.18 mmol) in DMF (2 mL). The reaction mixture is stirred at 80° C. for 18 h, quenched with AcOH (0.2 mL) and purified by RP-HPLC to provide compound 1103.

Example 45

Preparation of Intermediate 45a2

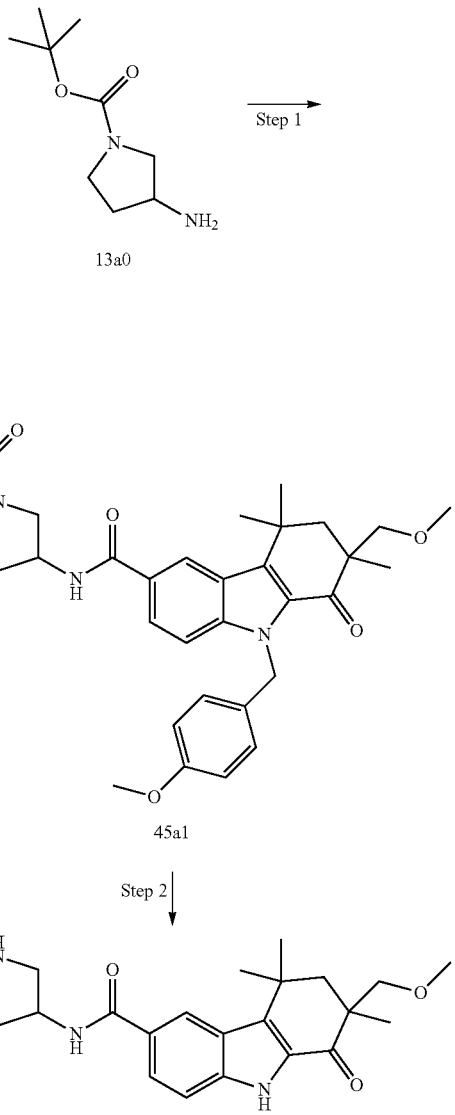

9a3 is coupled with 13a0 (step 1), followed by deprotection (step 2) using a procedure analogous to that described in Example 33 to provide intermediate 45a2.

Example 46

Preparation of Compound 5017

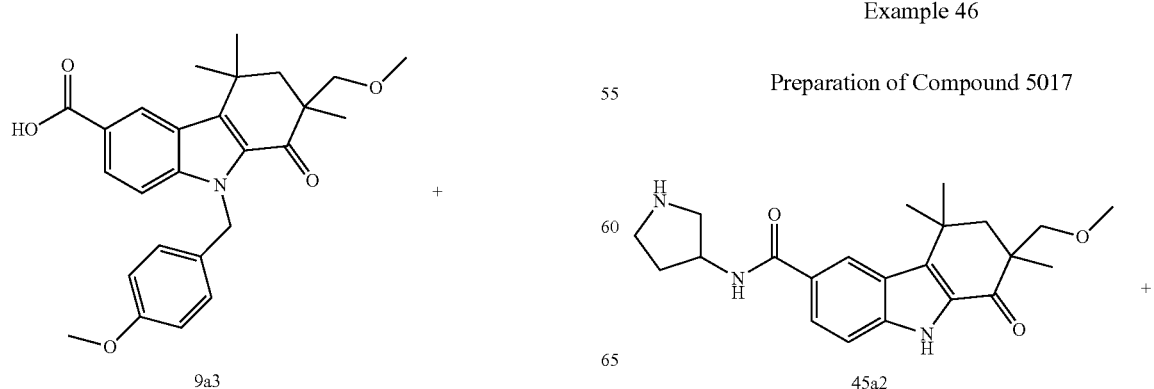

-continued

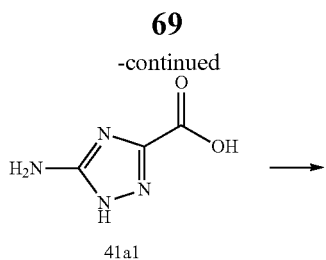
41a1

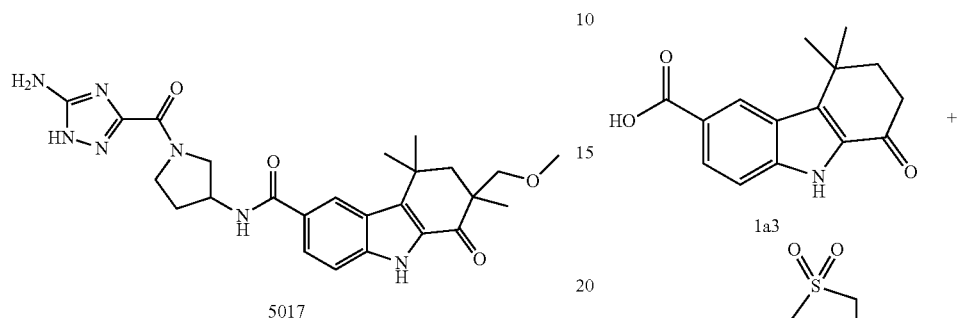
5017

45a2 is coupled with 41a1 using a procedure analogous to that described in Example 14 to provide compound 5017.

Example 47

Preparation of Compound 5014

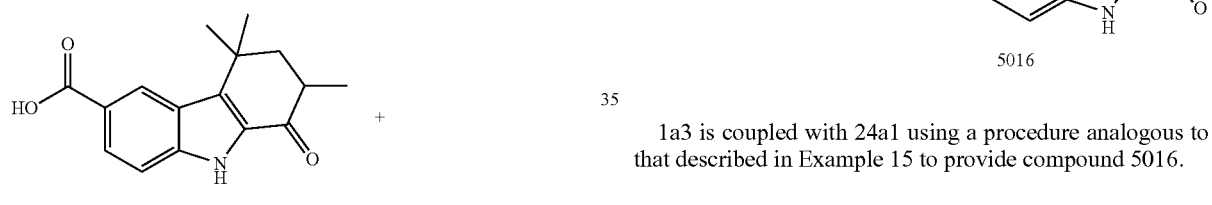

2a1 is coupled with 24a1 using a procedure analogous to that described in Example 15 to provide compound 5014.

Example 48

Preparation of Compound 5016

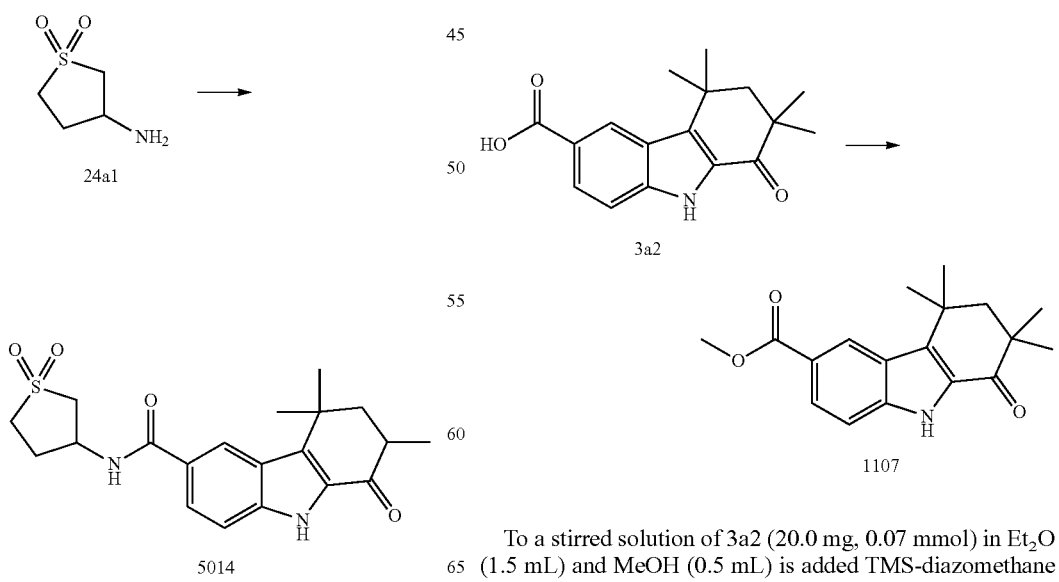

1a3 is coupled with 24a1 using a procedure analogous to that described in Example 15 to provide compound 5016.

Example 49

Preparation of Compound 1107

To a stirred solution of 3a2 (20.0 mg, 0.07 mmol) in Et$_2$O (1.5 mL) and MeOH (0.5 mL) is added TMS-diazomethane (2.0 M in ether, 46.0 μL, 0.08 mmol). The reaction mixture is stirred at RT overnight, and then the solvents are evaporated.

The residue is diluted in DMSO, filtered and purified by preparative RP-HPLC to provide compound 1107.

Example 50

Preparation of Compound 1104

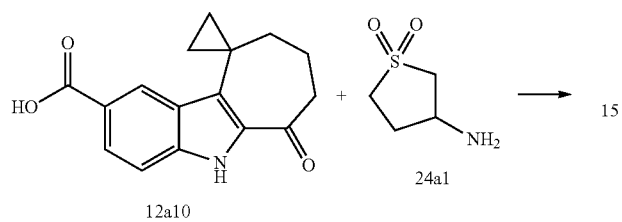

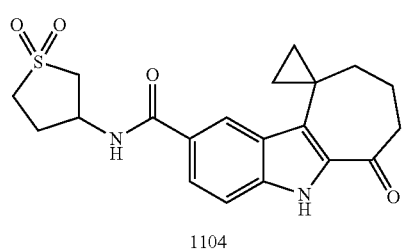

12a10 is coupled with 24a1 using a procedure analogous to that described in Example 15 to provide compound 1104.

Example 51

Preparation of Intermediate 51a2

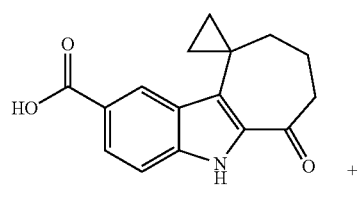

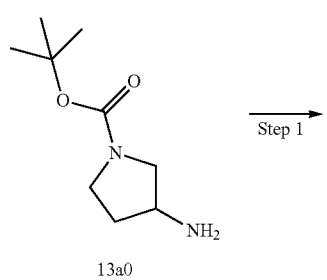

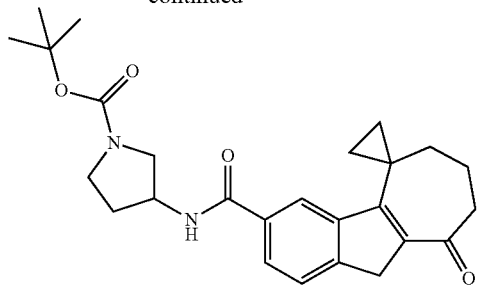

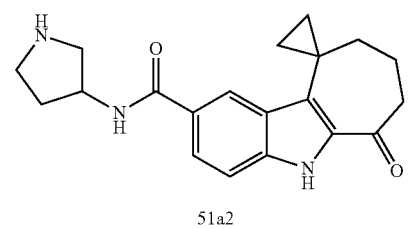

12a10 is coupled with 13a0 (step 1), followed by deprotection (step 2) using a procedure analogous to that described in Example 13 to provide intermediate 51a2.

Example 52

Preparation of Compound 1106

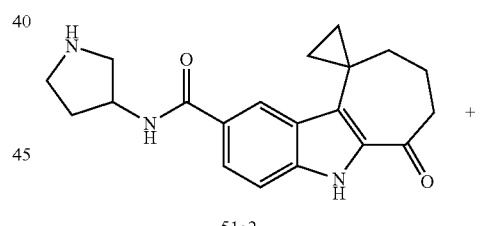

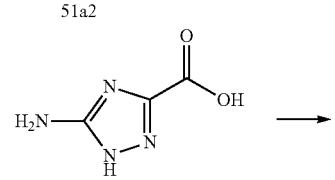

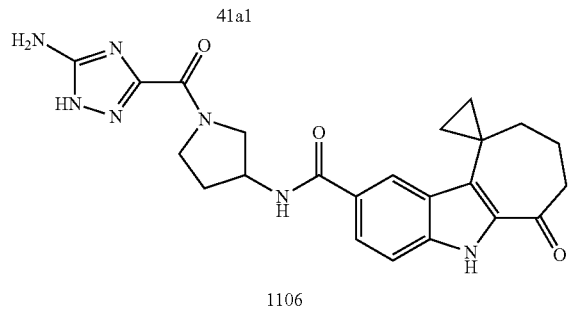

51a2 is coupled with 41a1 using a procedure analogous to that described in Example 14 to provide compound 1106.

Example 53

Preparation of Compound 7050

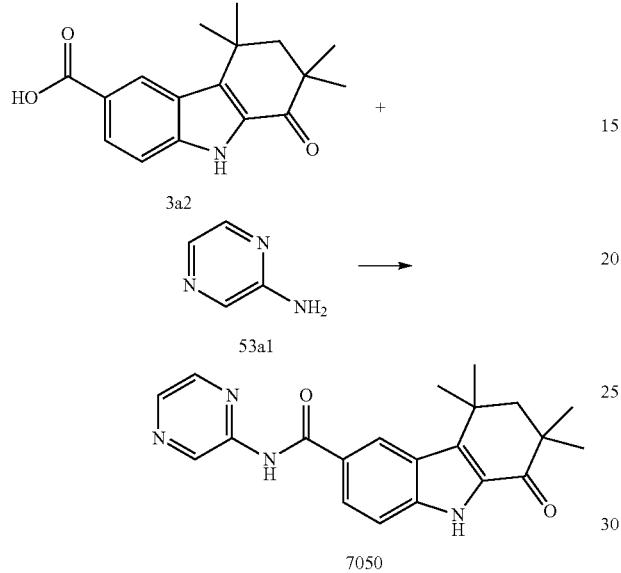

3a2 (40.0 mg, 0.14 mmol) and 53a1 (13.3 mg, 0.14 mmol, Aldrich) are dissolved in anhydrous pyridine (0.5 mL). The solution is cooled to −15° C. and phosphorus oxychloride (14.4 μL, 0.15 mmol) is added with stirring. The reaction mixture is stirred at −15° C. for 30 min, then at RT overnight. Pyridine (0.5 mL) and phosphorus oxychloride (14.4 μL, 0.15 mmol) are added to the reaction mixture that is then stirred for 16 h at RT. The reaction mixture is quenched with 1N HCl (0.5 mL) and extracted with DCM using a phase-separator. The solvents are evaporated and purification by preparative RP-HPLC provides compound 7050.

Example 54

Preparation of Intermediate 54a2

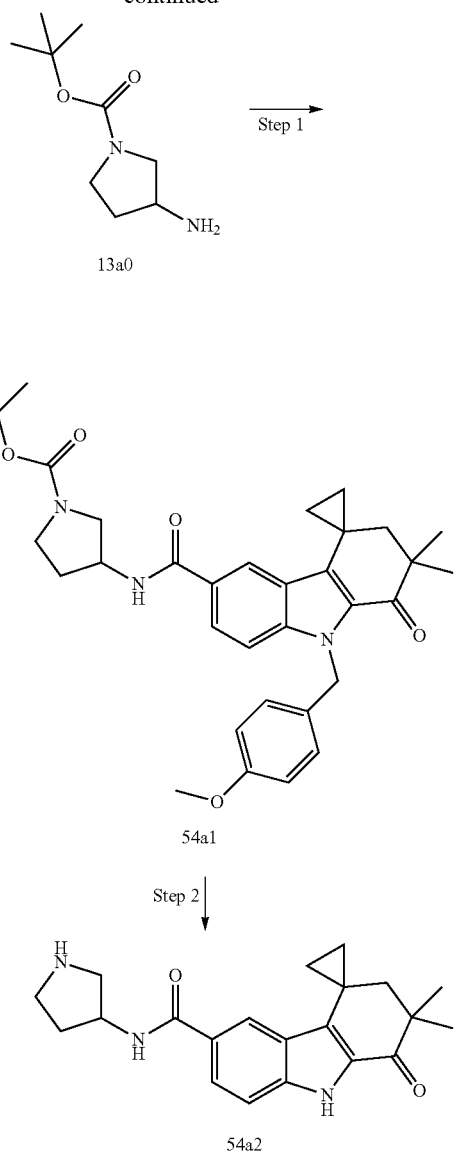

5a9 is coupled with 13a0 (step 1), followed by deprotection (step 2) using a procedure analogous to that described in Example 33 to afford intermediate 54a2.

Example 55

Preparation of Compound 6002

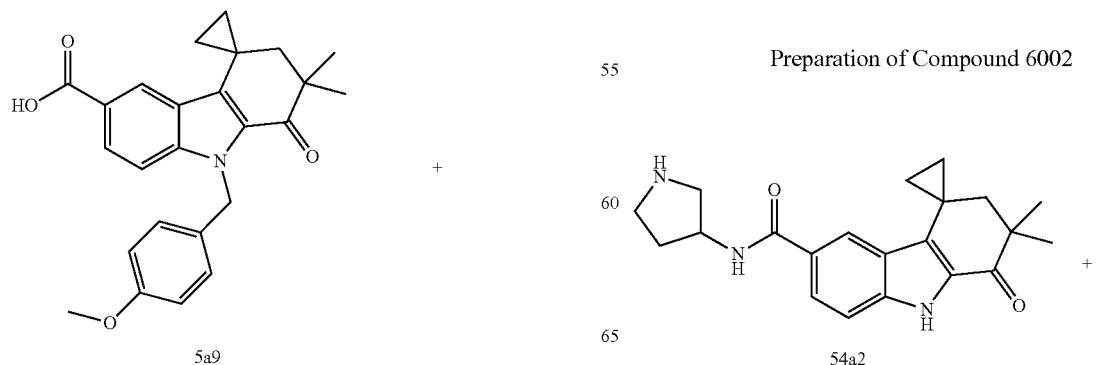

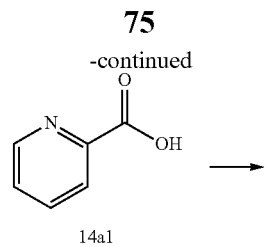

14a1

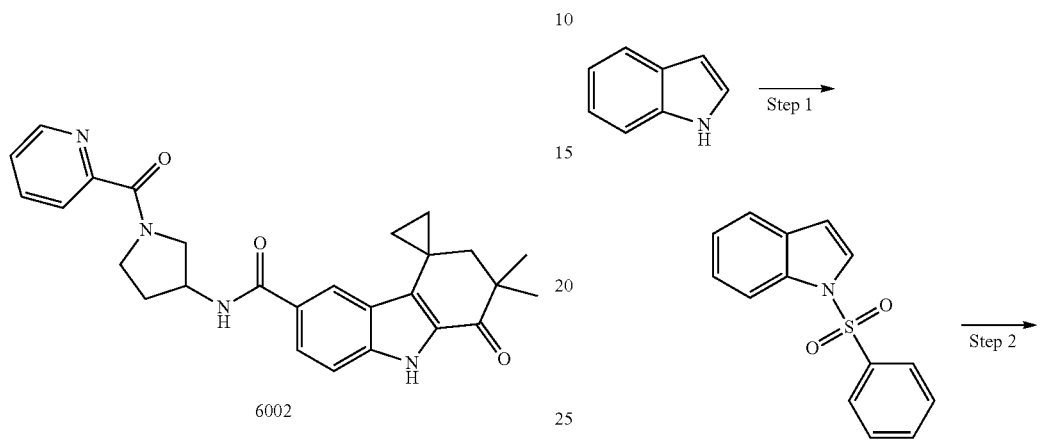

6002

54a2 is coupled with 14a1 using a procedure analogous to that described in Example 14 to afford compound 6002.

Example 56

Preparation of Compound 7038

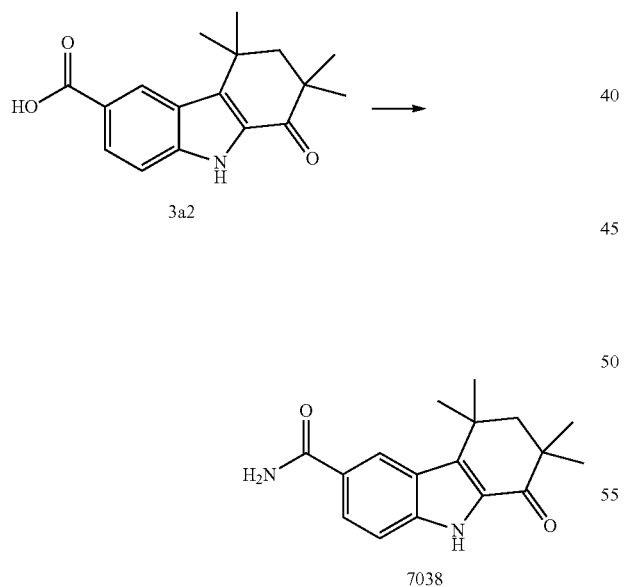

TEA (0.15 mL, 1.1 mmol) and HATU (200 mg 0.53 mmol) are added to a solution of ammonium bicarbonate (83.0 mg, 1.1 mmol) and 3a2 (100.0 mg, 0.35 mmol) in DMF (2 mL). The mixture is stirred for 15 h at RT and then diluted with EtOAc (50 mL) and washed with a saturated aqueous solution of $KHSO_4$ (20 mL) and brine. The organic phase is dried over $MgSO_4$, filtered and concentrated to dryness. The residue is dissolved in DMSO (2 mL) and purified by preparative RP-HPLC to provide compound 7038.

Example 57

Preparation of Compound 1101

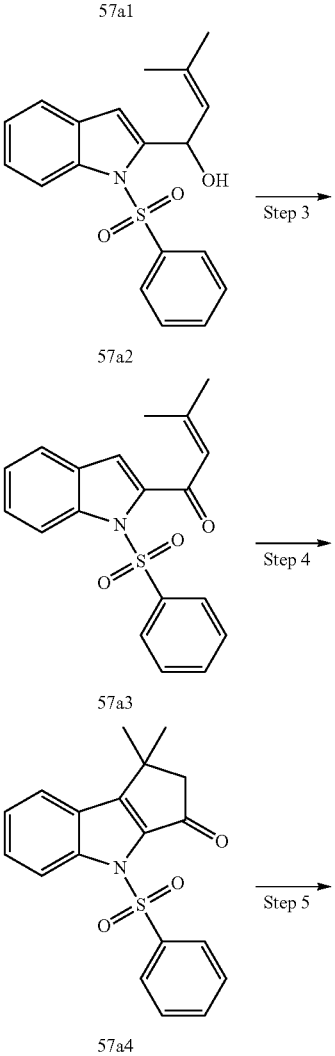

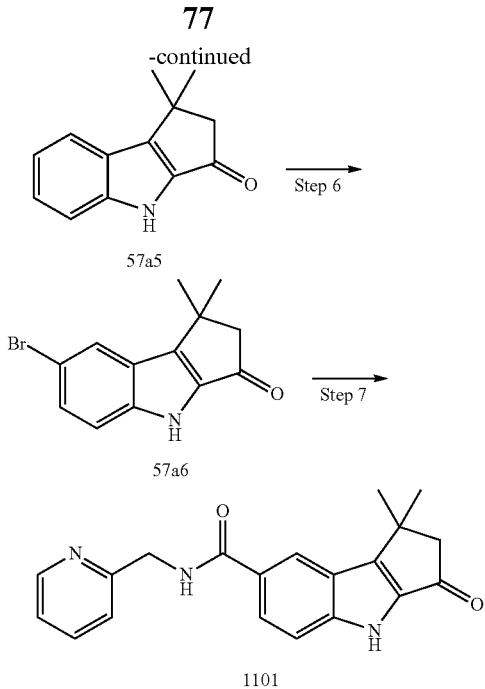

Step 1:
To a solution of indole (Aldrich, 50 g, 0.72 mol) in anhydrous THF (800 mL) is added NaH (60% in oil, 18.7 g, 0.47 mol) at 0° C. The reaction mixture is stirred at this temperature for 30 min, and then benzenesulfonyl chloride (82.9 g, 0.47 mol) is added. The reaction mixture is allowed to warm to RT and is stirred at RT overnight. The reaction mixture is quenched with water (100 mL), then extracted with EtOAc (2×), washed with brine, dried over $Na_2SO_4$ and concentrated. Purification by Combiflash (5%-10% EtOAc/Hex) affords 57a1.

Step 2:
To a solution of 57a1 (52.1 g, 0.20 mol) in anhydrous THF (1.5 L) at −78° C. is added a solution of t-BuLi (1.7M in pentane, 157 mL). The resulting solution is stirred at −78° C. for 1 h, and then a solution of 3-methyl-2-butenal (25.4 mL) in anhydrous THF (350 mL) is added over a period of 30 min. The reaction mixture is stirred at −78° C. for 45 min. After warming to RT, the reaction mixture is quenched with saturated $NH_4Cl$ (~1.5 L) and extracted with EtOAc. The combined organic layers are washed with brine, dried over $Na_2SO_4$ and concentrated in vacuo to provide crude 57a2 which is used as such.

Step 3:
To a solution of the curde 57a2 obtained in step 2 in anhydrous DCM (2 L) at RT is added 4-methyl morpholine N-oxide (35.5 g, 0.30 mol) and 4 Å molecular sieves powder (59 g). After 20 min, TPAP (3.5 g, 0.01 mol) is added and the mixture is stirred at RT overnight. The reaction mixture is filtered though a Celite pad with DCM washings. The filtrate is concentrated and purified by Combiflash (DCM/Hex) to provide 57a3.

Step 4:
To a solution of 57a3 (9.1 g, 26.81 mmol) in anhydrous toluene (300 mL) is added $BF_3·OEt_2$. The resulting mixture is heated to 120° C. and stirred at this temperature overnight. The reaction mixture is diluted with EtOAc, washed with brine, dried over $Na_2SO_4$ and filtered though a Celite pad. The filtrate is concentrated and purified by Combiflash (EtOAc/Hex) to provide 57a4.

Step 5:
A 5M NaOH aqueous solution (80 mL) is added to 57a4 (6.7 g, 0.02 mol) in MeOH (670 mL). The reaction mixture is heated to 80° C. and is maintained at this temperature for 90 min. The reaction mixture is concentrated and the residue is treated with DCM and water. The aqueous phase is back-extracted. The combined organic phases are washed with water and brine, dried over $Na_2SO_4$, and concentrated to provide 57a5.

Step 6:
To a solution of 57a5 (3.7 g, 18.57 mmol) in anhydrous DCM (80 mL) at −78° C. over 20 min is added pyridine (4.51 mL, 55.71 mmol) and a solution of bromine (2.86 mL, 55.71 mmol) in DCM (5 mL). The mixture is stirred at −78° C. for 3 min, then stirred at RT under an argon atmosphere for 60 min. The reaction mixture is cooled to −78° C., then Zn (6.07 g, 92.85 mmol) and HAc/THF (5.3 mL, 95.85 mmol) are added. The mixture is warmed to RT over 45 min, then stirred at RT for 30 min. DCM (200 mL) is added, and then 0.5N HCl (300 mL) is added to the mixture. The aqueous layer is extracted (2×) and the combined organic layers are concentrated and purified by Combiflash (5%-20% EtOAc/Hex) to provide 57a6.

Step 7:
To a solution of 57a6 (60.0 mg, 0.22 mmol) in DMF (4.00 mL) is added TEA (399.9 µL, 2.87 mmol) and 2-(aminomethyl)pyridine (73.9 µL, 0.72 mmol). The reaction mixture is degassed with argon for 5 min, then $Pd(dppf)Cl_2$-DCM adduct (23.4 mg, 0.029 mmol) is added. The reaction mixture is bubbled with CO(g) for 5 min. The reaction is kept under a (CO)g atmosphere (balloon), and heated to 85° C. for 18 h. The reaction mixture is cooled to RT and EtOAc is added. The mixture is washed with water, washed with brine (2×), dried over $MgSO_4$, filtered, concentrated and then purified by RP-HPLC to provide compound 1101.

Example 58

Production of HCV Pseudoparticles (HCVpp) and VSV Pseudoparticles (VSVpp)

Functional HCVpp are produced in 293FT cells (Invitrogen, Cat. No. R700-07) by co-transfection of HCV E1/E2 expression construct (pE1E2Con1#3) and a non-replicating HIV-1 based reporter vector (pNL4.3LucE-R-Δ725). The pNL4.3LucE-R-Δ725 reporter vector is generated by deleting a 725 pb DNA fragment within the gp160 encoding sequence corresponding to the StuI/BsaI restriction fragment of the original reporter vector (pNL4.3LucE-R-: NIH AIDS Research & Reference Reagent Program, Cat. No. 3418). The pE1E2Con1#3 expression vector encodes the HCV envelope gene (residues 171-746) (HCV isolate Con1, accession number AJ238799) cloned (HindIII/XbaI) into the pcDNA™ 3.1/Hygro(+) expression vector (Invitrogen Cat. No. V870-20). For HCVpp production, 293FT cells are co-transfected with pNL4.3LucE-R-Δ725 reporter vector and pE1/E2Con1#3 expression vector in a 30:1 (µg:µg) ratio using Lipofectamine™ 2000 (Invitrogen Cat. No. 11668-027) in serum-free Opti-MEM®I medium (Invitrogen Cat. No. 31985-070). Six hours post-transfection, the transfection medium is replaced with DMEM medium (Invitrogen, Cat. No. 319-005-CL) supplemented with 3% FBS (HyClone, Cat. No. SH30396.03) and 0.1 mM NEAA (Invitrogen, Cat. No. 11140-050). Cell culture supernatants containing HCVpp are collected at 48 hours post-transfection and centrifuged at 1000×g for 10 min to remove cellular debris. HEPES buffer (1M, pH7.5, Invitrogen Cat. No. 15630-080) is added at a final concentration of 10 mM to the clarified viral HCVpp containing supernatants, aliquoted and stored at −80° C. VSV pseudoparticles (VSVpp) for evaluating specificity of the compounds, are generated accoding to the above transfection protocol using a pLP-VSVG (Invitrogen, Cat. No. K4975-00) expression vector encoding the G envelope gene of VSV rather than the pE1E2Con1#3 expression vector.

Infection with HCV Pseudoparticles (HCVpp)

HCVpp incorporating a lentiviral backbone harboring the luciferase gene are used to assay for HCV entry as follows. Hep3B2.1-7 (ATCC number HB-8064) cells seeded in 96-well plates (Black 96-well ViewPlate™, Packard Cat. No. 6005182) are incubated with a concentration range of the tested compounds and supernatent containing HCVpp and polybrene. Typically the different reagents are mixed as follows: 10 µL of cells (1×10$^6$ cells/mL in DMEM medium supplemented with 3% FBS and 0.1 mM NEAA), 15 µL of compound solution (DMEM medium supplemented with 3% FBS, 0.1 mM NEAA and 3% DMSO) and 50 µL of undiluted supernatant containing HCVppto which a solution of polybrene is added (Sequa-brene, Sigma Cat. No. S2667, final concentration of 4.5 mg/mL). The plates are centrifuged for 60 min at 400×g and then incubated for 4 h at 37° C. (5% CO$_2$) before addition of 10 µL of DMEM medium supplemented with 20% FBS and 0.1 mM NEAA. Seventy-two hours after infection the luciferase level is evaluated by a standard luminescences assay. Compounds that reduce viral entry limit the amount of HCVpp that is transduced into the host cells and thus reduce the luciferase levels and the resulting luminescence signal. The most efficacious compounds induce the most significant reduction in luminescence.

Specificity of the compounds is tested by evaluating the inhibitory effect on VSVpp, according to the infection protocol described above for HCVpp, except that the supernatant containing VSVpp is diluted in media to generate a similar signal as generated using the supernatant containing undiluted HCVpp. Compounds that inhibit HCVpp entry significantly more (10-fold) than infections mediated by VSVpp are considered to be specific. All the compounds listed in Tables 1 to 10 are found to significantly reduce viral entry as measured by the HCVpp/luciferase assay, and are specific when assayed against the inhibitory effect on VSVpp.

The compounds of the invention show EC$_{50}$ values in the range of 1 µM or less tested in the assay of Example 58. Representative data is shown below:

| Cmpd # | EC$_{50}$ (nM) (Ex. 58) |
|---|---|
| 1103 | 34 |
| 1104 | 122 |
| 1107 | 195 |
| 2003 | 117 |
| 2026 | 36 |
| 2058 | 39 |
| 3006 | 102 |
| 5003 | 385 |
| 5008 | 22 |
| 5014 | 187 |
| 5017 | 9.3 |
| 6001 | 66 |
| 6016 | 3.4 |
| 7008 | 201 |
| 7010 | 126 |
| 7019 | 82 |
| 7050 | 88 |
| 9004 | 85 |

Tables of Compounds

The following tables list compounds representative of the invention. All of the compounds in Tables 1 to 10 are synthesized analogously to the Examples described above. For each compound in the tables, the analogous synthetic route to prepare each compound is identified by Example number. It will be apparent to a skilled person that the analogous synthetic routes may be used, with appropriate modifications, to prepare the compounds of the invention as described herein.

Retention times (t$_R$) for each compound are measured using the standard analytical HPLC or UPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC or UPLC instruments. Even when measured on the same instrument, the values may vary when measured, for example, using different individual HPLC or UPLC columns, or, when measured on the same instrument and the same individual column, the values may vary, for example, between individual measurements taken on different occasions.

TABLE 1

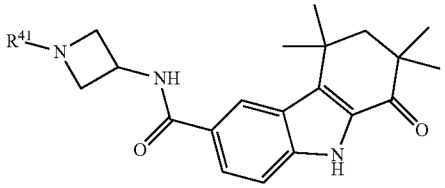

| Cmpd # | R$^{41}$ | t$_R$ (min) | (M + H)$^+$ | Synthesis Method |
|---|---|---|---|---|
| 1001 | 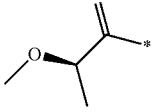 | 1.77 | 426.3 | 13b2 & Ex. 14 |
| 1002 | 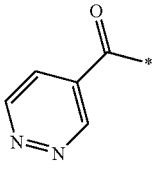 | 1.55 | 398.2 | Ex. 15 |
| 1003 | 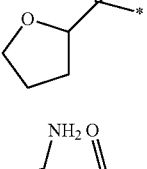 | 1.66 | 446.3 | 13b2 & Ex. 14 |
| 1004 | 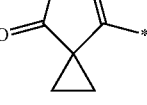 | 1.8 | 438.3 | 13b2 & Ex. 14 |
| 1005 |  | 1.65 | 451.3 | 13b2 & Ex. 14 |

TABLE 1-continued

[Structure: R41-N-azetidine-NH-C(O)-tetrahydrocarbazolone with gem-dimethyl groups]

| Cmpd # | R41 | $t_R$ (min) | (M + H)+ | Synthesis Method |
|---|---|---|---|---|
| 1006 | imidazo[1,2-a]pyrimidin-2-yl-C(O)- | 1.7 | 485.3 | 13b2 & Ex. 14 |
| 1007 | (4-methylpyrazol-1-yl)CH2-C(O)- | 1.83 | 462.3 | 13b2 & Ex. 14 |
| 1008 | (4-methyloxazol-5-yl)-C(O)- | 1.79 | 449.3 | 13b2 & Ex. 14 |
| 1009 | (pyridin-3-yl)CH2-C(O)- | 1.7 | 459.3 | 13b2 & Ex. 14 |
| 1010 | (3,5-dimethylisoxazol-4-yl)-C(O)- | 1.81 | 463.3 | 13b2 & Ex. 14 |
| 1011 | (5-methyl-1H-1,2,4-triazol-3-yl)-C(O)- | 1.72 | 449.3 | 13b2 & Ex. 14 |
| 1012 | pyrazolo[1,5-a]pyrimidin-3-yl-C(O)- | 1.74 | 485.3 | 13b2 & Ex. 14 |
| 1013 | (1-methyl-1H-pyrazol-5-yl)-C(O)- | 1.81 | 448.3 | 13b2 & Ex. 14 |
| 1014 | (isoxazol-5-yl)-C(O)- | 1.77 | 435.3 | 13b2 & Ex. 14 |
| 1015 | (2-methylaminopyrimidin-5-yl)-C(O)- | 1.77 | 475.3 | 13b2 & Ex. 14 |
| 1016 | (3-methylisoxazol-5-yl)CH2-C(O)- | 1.75 | 463.3 | 13b2 & Ex. 14 |
| 1017 | (1-methyl-1H-pyrazol-4-yl)-C(O)- | 1.7 | 448.3 | 13b2 & Ex. 14 |
| 1018 | (4-methyl-1H-imidazol-2-yl)-C(O)- | 1.84 | 448.3 | 13b2 & Ex. 14 |
| 1019 | (5-isopropyl-1H-1,2,4-triazol-3-yl)-C(O)- | 1.86 | 477.3 | 13b2 & Ex. 14 |
| 1020 | (3-methylisoxazol-4-yl)-C(O)- | 1.81 | 449.3 | 13b2 & Ex. 14 |

TABLE 1-continued

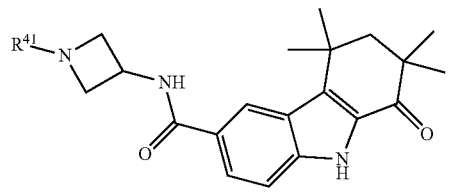

| Cmpd # | R41 | tR (min) | (M + H)+ | Synthesis Method |
|---|---|---|---|---|
| 1021 | 3-pyridinyl-C(O)- | 1.74 | 445.3 | 13b2 & Ex. 14 |
| 1022 | 4-methyl-1,2,5-oxadiazol-3-yl-C(O)- | 1.98 | 450.2 | 13b2 & Ex. 14 |
| 1023 | 1-methyl-1H-pyrazolo[3,4-b]pyridin-3-yl-C(O)- | 1.97 | 499.3 | 13b2 & Ex. 14 |
| 1024 | 6-methylpyridin-3-yl-C(O)- | 1.81 | 459.3 | 13b2 & Ex. 14 |
| 1025 | cinnolin-4-yl-C(O)- | 1.82 | 496.3 | 13b2 & Ex. 14 |
| 1026 | 5-(methylsulfonyl)pyridin-3-yl-C(O)- | 1.72 | 523.3 | 13b2 & Ex. 14 |
| 1027 | 3-methoxyisoxazol-5-yl-C(O)- | 1.87 | 465.3 | 13b2 & Ex. 14 |

TABLE 1-continued

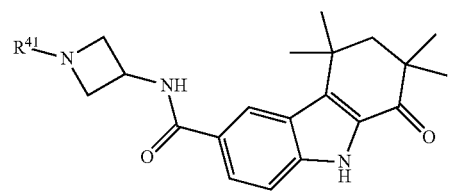

| Cmpd # | R41 | tR (min) | (M + H)+ | Synthesis Method |
|---|---|---|---|---|
| 1028 | 3-methylisoxazol-5-yl-C(O)- | 1.83 | 449.3 | 13b2 & Ex. 14 |

TABLE 2

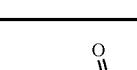

| Cmpd # | R41 | tR (min) | (M + H)+ | Synthesis Method |
|---|---|---|---|---|
| 2001 | 5-(trifluoromethyl)-4H-1,2,4-triazol-3-yl-C(O)- | 2.00 | 517.4 | Ex. 14 |
| 2002 | 5-amino-4H-1,2,4-triazol-3-yl-C(O)- | 1.65 | 464.4 | Ex. 14 |
| 2003 | 3-fluoropropyl | 1.51 | 400.3 | Ex. 18 |
| 2004 | 2-methoxyethyl | 1.52 | 412.3 | Ex. 18 |
| 2005 | pyridin-3-ylmethyl | 1.53 | 445.3 | Ex. 18 |

TABLE 2-continued

| Cmpd # | R41 | $t_R$ (min) | (M+H)+ | Synthesis Method |
|---|---|---|---|---|
| 2006 | acetyl | 1.73 | 396.1 | Ex. 14 |
| 2007 | N-methylsulfamoyl pyridinyl carbonyl | 1.71 | 552.4 | Ex. 21 |
| 2008 | 5-hydroxypyridin-2-yl carbonyl | 1.79 | 475.4 | Ex. 14 |
| 2009 | [1,2,4]triazolo[1,5-a]pyrimidin-2-yl carbonyl | 1.7 | 500.4 | Ex. 14 |
| 2010 | 1H-1,2,3-triazol-4-yl carbonyl | 1.71 | 449.4 | Ex. 14 |
| 2011 | 1-(2-methoxyethyl)-1H-pyrazol-3-yl carbonyl | 1.81 | 506.5 | Ex. 14 |
| 2012 | pyridazin-3-yl carbonyl | 1.71 | 460.3 | Ex. 14 |
| 2013 | pyrimidin-5-yl carbonyl | 1.71 | 460.3 | Ex. 14 |
| 2014 | pyrimidin-2-yl carbonyl | 1.71 | 460.4 | Ex. 14 |
| 2015 | 5-(methylsulfonyl)pyridin-3-yl carbonyl | 1.72 | 537.5 | Ex. 14 |
| 2016 | thiazol-5-yl carbonyl | 1.76 | 465.3 | Ex. 14 |
| 2017 | 1-methyl-1H-pyrazol-3-yl carbonyl | 1.78 | 462.4 | Ex. 14 |
| 2018 | 5-amino-1,3,4-oxadiazol-2-yl carbonyl | 1.7 | 465.4 | Ex. 14 |
| 2019 | pyrazin-2-yl carbonyl | 1.8 | 460.2 | Ex. 14 |
| 2020 | pyridin-3-yl carbonyl | 1.73 | 459.3 | Ex. 14 |
| 2021 | 6-amino-2-methylpyridin-3-yl carbonyl | 1.6 | 488.5 | Ex. 14 |
| 2022 | 1,3-dimethyl-1H-pyrazol-4-yl carbonyl | 1.77 | 476.4 | Ex. 14 |
| 2023 | 1-isopropyl-1H-1,2,4-triazol-3-yl carbonyl | 1.82 | 491.5 | Ex. 23 |

TABLE 2-continued

| Cmpd # | R41 | $t_R$ (min) | (M + H)+ | Synthesis Method |
|---|---|---|---|---|
| 2024 | 5-methylpyrazin-2-yl carbonyl | 1.84 | 474.3 | Ex. 14 |
| 2025 | 1H-imidazol-2-yl carbonyl | 1.78 | 448.4 | Ex. 14 |
| 2026 | pyridin-2-yl carbonyl | 1.8 | 459.3 | Ex. 14 |
| 2027 | 5-aminopyridin-2-yl carbonyl | 1.72 | 474.4 | Ex. 14 |
| 2028 | pyridazin-4-yl carbonyl | 1.67 | 460.3 | Ex. 14 |
| 2029 | pyridin-4-yl carbonyl | 1.73 | 459.3 | Ex. 14 |
| 2030 | imidazo[1,2-a]pyrimidin-2-yl carbonyl | 1.76 | 499.2 | Ex. 14 |
| 2031 | tert-butoxycarbonyl | 2.08 | 452.2 (M − H)+ | Ex. 13/13a1 |
| 2032 | 6-aminopyridin-3-yl carbonyl | 1.69 | 474.3 | Ex. 14 |
| 2033 | oxazol-5-yl carbonyl | 1.76 | 449.3 | Ex. 14 |
| 2034 | 5-aminopyrazin-2-yl carbonyl | 1.73 | 475.4 | Ex. 14 |
| 2035 | 1H-pyrazol-4-yl carbonyl | 1.69 | 448.3 | Ex. 14 |
| 2036 | 2-amino-1,3,4-thiadiazol-5-yl carbonyl | 1.74 | 481.4 | Ex. 22 |
| 2037 | 1-methyl-1H-pyrazol-5-yl carbonyl | 1.82 | 462.3 | Ex. 14 |
| 2038 | 6-methylpyridin-3-yl carbonyl | 1.83 | 473.3 | Ex. 14 |
| 2039 | 1H-imidazol-4-yl carbonyl | 1.67 | 448.4 | Ex. 14 |
| 2040 | 6-acetamidopyridin-3-yl carbonyl | 1.75 | 516.5 | Ex. 14 |
| 2041 | 1-methyl-1H-imidazol-2-yl carbonyl | 1.79 | 462.4 | Ex. 14 |
| 2042 | 3-amino-1H-pyrazol-4-yl carbonyl | 1.69 | 463.4 | Ex. 14 |

TABLE 2-continued

| Cmpd # | R41 | $t_R$ (min) | (M+H)+ | Synthesis Method |
|---|---|---|---|---|
| 2043 | | 1.72 | 463.4 | Ex. 14 |
| 2044 | | 1.72 | 463.4 | Ex. 14 |
| 2045 | | 1.74 | 464.4 | Ex. 14 |
| 2046 | | 1.85 | 476.4 | Ex. 14 |
| 2047 | | 1.78 | 449.3 | Ex. 14 |
| 2048 | | 1.76 | 462.3 | Ex. 14 |
| 2049 | | 1.73 | 449.3 | Ex. 14 |
| 2050 | | 1.75 | 537.3 | Ex. 14 |
| 2051 | | 1.72 | 463.4 | Ex. 14 |
| 2052 | | 1.79 | 463.4 | Ex. 14 |
| 2053 | | 1.72 | 463.4 | Ex. 14 |
| 2054 | | 1.79 | 465.2 | Ex. 14 |
| 2055 | | 1.85 | 491.3 | Ex. 14 |
| 2056 | | 1.73 | 448.4 | Ex. 14 |
| 2057 | | 1.7 | 537.4 | Ex. 14 |
| 2058 | | 1.73 | 432.2 | Ex. 19 |

TABLE 3

| Cmpd # | R4 | $t_R$ (min) | (M+H)+ | Synthesis Method |
|---|---|---|---|---|
| 3001 | | 1.75 | 488.4 | 13f2 & Ex. 14 |

TABLE 3-continued

| Cmpd # | R⁴ | $t_R$ (min) | (M + H)⁺ | Synthesis Method |
|---|---|---|---|---|
| 3002 | (pyridin-2-yl-carbonyl)-3-methylpiperidine | 1.82 | 473.3 | 13e2 & Ex. 14 |
| 3003 | (tetrahydrofuran-3-yl-carbonyl)-3-methylpiperidine | 1.87 | 480.4 | 13f2 & Ex. 14 |
| 3004 | (6-aminopyridin-3-yl-carbonyl)-3-methylpiperidine | 1.78 | 502.4 | 13f2 & Ex. 14 |
| 3005 | 1-acetyl-3-methylpiperidine | 1.78 | 410.3 | 13e2 & Ex. 14 |
| 3006 | 1,3-dimethylpiperidine | 2.01 | 382.3 | Ex. 43 |
| 3007 | (pyridazin-4-yl-carbonyl)-3-methylpiperidine | 1.72 | 474.3 | 13e2 & Ex. 14 |
| 3008 | 3-methylpiperidine | 1.55 | 382.4 | 13f2 & Ex. 14 |
| 3009 | 1-(methylsulfonyl)-3-methylpiperidine | 2.44 | 446.1 | 13e2 & Ex. 19 |
| 3010 | (pyridin-3-yl-carbonyl)-3-methylpiperidine | 1.78 | 473.3 | 13e2 & Ex. 14 |

TABLE 3-continued

| Cmpd # | R⁴ | $t_R$ (min) | (M + H)⁺ | Synthesis Method |
|---|---|---|---|---|
| 3011 | 1-(2-methoxyethyl)-3-methylpiperidine | 1.57 | 426.4 | 13e2 & Ex. 18 |
| 3012 | 1-(2-fluoroethyl)-3-methylpiperidine | 1.55 | 414.3 | 13e2 & Ex. 18 |
| 3013 | (pyridin-3-yl-carbonyl)-3-methylpiperidine | 1.83 | 487.4 | 13f2 & Ex. 14 |
| 3014 | 1-(pyridin-3-ylmethyl)piperidine | 2.16 | 459.2 | 13e2 & Ex. 18 |
| 3015 | 1-(methylsulfonyl)-3-methylpiperidine | 1.77 | 446.3 | 13g2 & Ex. 19 |
| 3016 | 1-(2-fluoroethyl)-3-methylpiperidine | 1.55 | 414.3 | 13e2 & Ex. 18 |

TABLE 4

| Cmpd # | R⁴¹ | $t_R$ (min) | (M + H)⁺ | Synthesis Method |
|---|---|---|---|---|
| 4001 | H | 1.49 | 368.2 | 13h2 |
| 4002 | (S)-2-hydroxypropanoyl | 1.74 | 440.3 | Ex. 15 |

TABLE 4-continued
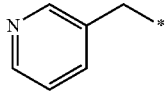
| Cmpd # | R⁴¹ | $t_R$ (min) | (M + H)⁺ | Synthesis Method |
|---|---|---|---|---|
| 4003 | CH₃ | 2.35 | 382.2 | 13h2 & Ex. 18 |
| 4004 | 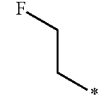 | 1.52 | 459.3 | 13h2 & Ex. 18 |
| 4005 |  | 1.50 | 414.3 | 13h2 & Ex. 18 |
| 4006 | 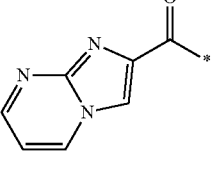 | 1.75 | 410.3 | 13h2 & Ex. 14 |
| 4007 |  | 1.66 | 513.4 | 13h2 & Ex. 14 |
| 4008 | 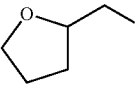 | 1.77 | 446.2 | 13h2 & Ex. 19 |
| 4009 | 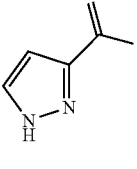 | 1.57 | 452.4 | 13h2 & Ex. 18 |
| 4010 | 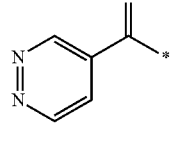 | 1.74 | 462.4 | 13h2 & Ex. 14 |
| 4011 | 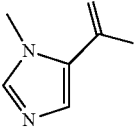 | 1.70 | 474.1 | 13h2 & Ex. 14 |
| 4012 | 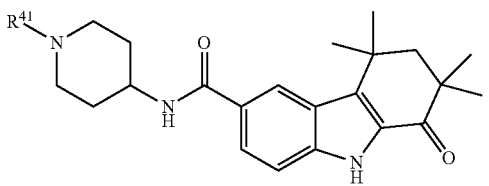 | 1.70 | 476.4 | 13h2 & Ex. 14 |
| 4013 | 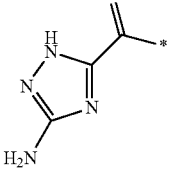 | 1.68 | 478.3 | 13h2 & Ex. 14 |
| 4014 | 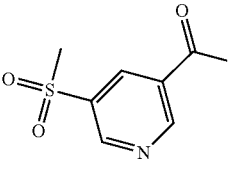 | 1.74 | 463.3 | 13h2 & Ex. 14 |
| 4015 | 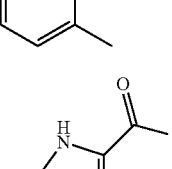 | 1.75 | 551.3 | 13h2 & Ex. 14 |
| 4016 | 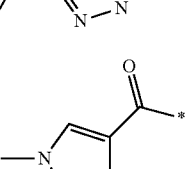 | 2.54 | 487.5 | 13h2 & Ex. 14 |
| 4017 | 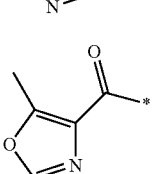 | 1.85 | 505.4 | 13h2 & Ex. 14 |
| 4018 | 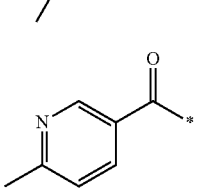 | 1.74 | 476.4 | 13h2 & Ex. 14 |
| 4019 |  | 1.89 | 491.4 | 13h2 & Ex. 14 |
| 4020 |  | 2.52 | 487.4 | 13h2 & Ex. 14 |

TABLE 4-continued

| Cmpd # | R⁴¹ | $t_R$ (min) | (M + H)⁺ | Synthesis Method |
|---|---|---|---|---|
| 4021 | isoxazol-5-yl-carbonyl | 1.80 | 463.3 | 13h2 & Ex. 14 |
| 4022 | thiazol-5-yl-carbonyl | 1.78 | 479.3 | 13h2 & Ex. 14 |

TABLE 5

| Cmpd # | R⁴ | R⁵ | R⁶ | $t_R$ (min) | (M + H)⁺ | Synthesis Method |
|---|---|---|---|---|---|---|
| 5001 | 3-methyl-1,1-dioxo-tetrahydrothiophen-3-yl | tetrahydropyran-4-yl | | 1.5 | 459.3 | Ex. 26 |
| 5002 | 3-(1,2,4-triazol-1-yl)propyl | tetrahydropyran-4-yl | | 1.47 | 436.3 | Ex. 26 |
| 5003 | 1,1-dioxo-tetrahydrothiophen-3-yl | tetrahydropyran-4-yl | | 1.45 | 445.2 | Ex. 26 |
| 5004 | 2-(tetrahydropyran-4-yl)ethyl | CH₃ | H | 1.86 | 383.2 | Ex. 47 |
| 5005 | 1-(1H-pyrazol-3-yl-carbonyl)pyrrolidin-3-yl | *CH₂OCH₃ | CH₃ | 2.24 | 478.2 | Ex. 46 |
| 5006 | 1,1-dioxo-tetrahydrothiophen-3-yl | 1-methyl-cyclopropyl | | 2.23 | 401.2 | Ex. 31 |

TABLE 5-continued

| Cmpd # | R⁴ | R⁵ | R⁶ | t_R (min) | (M + H)⁺ | Synthesis Method |
|---|---|---|---|---|---|---|
| 5007 | 3-pyridyl-C(O)-pyrrolidin-3-yl | spiro-cyclopropyl | | 2.29 | 457.3 | Ex. 36 |
| 5008 | (1H-1,2,4-triazol-3-yl)-C(O)-pyrrolidin-3-yl | spiro-cyclopropyl | | 2.22 | 447.4 | Ex. 36 |
| 5009 | 1,1-dioxo-tetrahydrothiophen-3-yl | * | * | 2.62 | 431.4 | Ex. 32 |
| 5010 | (1-methyl-1H-pyrazol-4-yl)-C(O)-pyrrolidin-3-yl | * | * | 2.64 | 490.5 | Ex. 34 |
| 5011 | (3-amino-1H-1,2,4-triazol-5-yl)-C(O)-pyrrolidin-3-yl | * | * | 2.55 | 492.4 | Ex. 34 |
| 5012 | pyridin-2-ylmethyl | CH₃ | H | 1.76 | 362.2 | Ex. 47 |
| 5013 | (6-trifluoromethylpyridin-3-yl)methyl | H | CH₃ | 1.94 | 430.2 | Ex. 47 |
| 5014 | 1,1-dioxo-tetrahydrothiophen-3-yl | H | CH₃ | 3.65 | 389.1 | Ex. 47 |
| 5015 | (6-trifluoromethylpyridin-3-yl)methyl | H | H | 2.977 | 416.1 | Ex. 48 |

TABLE 5-continued

| Cmpd # | R⁴ | R⁵ | R⁶ | t_R (min) | (M + H)⁺ | Synthesis Method |
|---|---|---|---|---|---|---|
| 5016 | (1,1-dioxo-tetrahydrothiophen-3-yl) | H | H | 1.44 | 375.1 | Ex. 48 |
| 5017 | (5-amino-1H-1,2,4-triazol-3-yl)carbonyl-pyrrolidin-3-yl | *–CH₂–O–CH₃ | CH₃ | 494.2 | 494.2 | Ex. 46 |

TABLE 6

| Cmpd # | R⁴ | R¹/R² group | t_R (min) | (M + H)⁺ | Synthesis Method |
|---|---|---|---|---|---|
| 6001 | 1H-1,2,4-triazol-1-yl-propyl | cyclopropyl | 1.59 | 392.4 | Ex. 25 |
| 6002 | pyridin-2-ylcarbonyl-pyrrolidin-3-yl | cyclopropyl | 2.41 | 457.4 | Ex. 55 |
| 6003 | (1,1-dioxo-tetrahydrothiophen-3-yl) | cyclopropyl | 2.23 | 401.3 | Ex. 24 |
| 6004 | (5-amino-1H-1,2,4-triazol-3-yl)carbonyl-(3R)-pyrrolidin-3-yl | cyclobutyl | 1.72 | 476.4 | Ex. 41 |

TABLE 6-continued
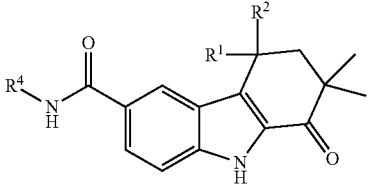
| Cmpd # | R⁴ | R¹ R² | $t_R$ (min) | (M + H)⁺ | Synthesis Method |
|---|---|---|---|---|---|
| 6005 | 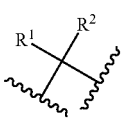 | 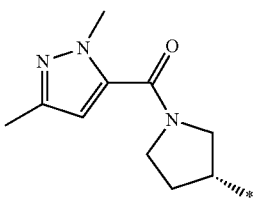 [SMILES: *[C@@H]1CCN(C(=O)c2cc(C)nn2C)C1] | 1.91 | 488.5 | Ex. 41 |
| 6006 | 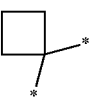 | 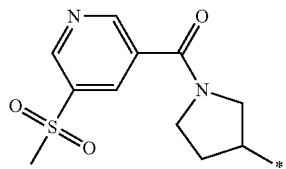 [SMILES: *C1CCN(C(=O)c2cncc(S(C)(=O)=O)c2)C1] | 1.71 | 549.5 | Ex. 39 |
| 6007 | 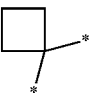 | 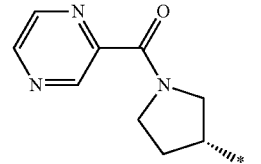 [SMILES: *[C@@H]1CCN(C(=O)c2cnccn2)C1] | 1.77 | 472.2 | Ex. 41 |
| 6008 | 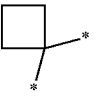 | 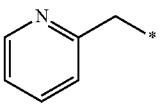 [SMILES: *Cc1ccccn1] | 1.89 | 388.4 | Ex. 37 |
| 6009 | 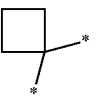 | 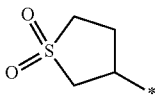 | 1.78 | 415.3 | Ex. 37 |
| 6010 | 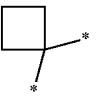 | 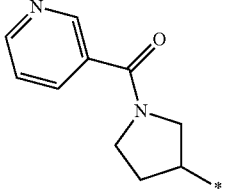 [SMILES: *C1CCN(C(=O)c2cccnc2)C1] | 1.81 | 471.4 | Ex. 39 |
| 6011 | 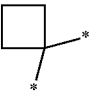 | 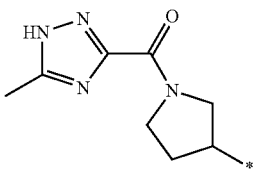 [SMILES: *C1CCN(C(=O)c2n[nH]c(C)n2)C1] | 1.80 | 475.3 | Ex. 39 |

TABLE 6-continued

| Cmpd # | R⁴ | R¹R² group | t_R (min) | (M + H)⁺ | Synthesis Method |
|---|---|---|---|---|---|
| 6012 | 1H-1,2,4-triazol-3-yl-C(O)-pyrrolidin-3-yl | cyclopropyl | 2.23 | 447.4 | Ex. 55 |
| 6013 | 6-methylpyridin-3-yl-C(O)-pyrrolidin-3-yl | cyclobutyl | 1.86 | 485.4 | Ex. 39 |
| 6014 | 3-methylisoxazol-4-yl-C(O)-pyrrolidin-3-yl | cyclobutyl | 1.86 | 475.3 | Ex. 39 |
| 6015 | 1H-1,2,4-triazol-3-yl-C(O)-(S)-pyrrolidin-3-yl | cyclobutyl | 1.77 | 461.4 | Ex. 41 |
| 6016 | 1H-1,2,4-triazol-3-yl-C(O)-pyrrolidin-3-yl | cyclobutyl | 1.77 | 461.3 | Ex. 39 |
| 6017 | 6-(methylsulfonyl)pyridin-3-yl-C(O)-(S)-pyrrolidin-3-yl | cyclobutyl | 1.77 | 549.5 | Ex. 41 |
| 6018 | 6-(methylsulfonyl)pyridin-3-yl-C(O)-pyrrolidin-3-yl | cyclobutyl | 1.78 | 549.4 | Ex. 39 |

TABLE 7

| Cmpd # | R⁴ | R³ | $t_R$ (min) | (M + H)⁺ | Synthesis Method |
|---|---|---|---|---|---|
| 7001 | tetrahydrothiophene 1,1-dioxide-3-yl | CH₃ | 1.66 | 417.1 | Ex. 15 |
| 7002 | 4-hydroxy-tetrahydrothiophene 1,1-dioxide-3-yl | CH₃ | 1.65 | 433.2 | Ex. 15 |
| 7003 | 4,4-dimethyl-tetrahydrothiophene 1,1-dioxide-3-yl | CH₃ | 1.77 | 431.2 | Ex. 15 |
| 7004 | trans-4-aminocyclohexyl | H | 2.08 | 382.4 | 13i2 |
| 7005 | 2-oxopyrrolidin-3-yl | H | 1.66 | 368.3 | Ex. 15 |
| 7006 | 2,2-dimethyl-3-morpholinopropyl | H | 1.66 | 426.4 | Ex. 15 |
| 7007 | (1-(methylsulfonyl)piperidin-2-yl)methyl | H | 2.51 | 460.4 | 13j2 & Ex. 19 |
| 7008 | 1,1-dioxotetrahydro-2H-thiopyran-4-yl | H | 2.32 | 417.2 | Ex. 20 |
| 7009 | (S)-pyrrolidin-2-ylmethyl | H | 1.51 | 368.3 | Ex. 13 |

TABLE 7-continued
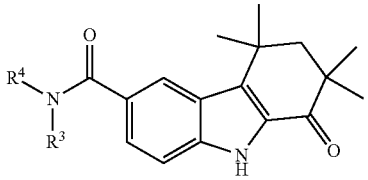
| Cmpd # | R⁴ | R³ | t_R (min) | (M + H)⁺ | Synthesis Method |
|---|---|---|---|---|---|
| 7010 | 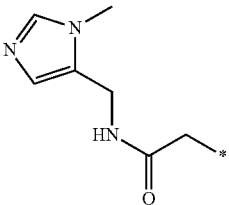 [SMILES: *CC(=O)NCc1cncn1C] | H | 1.45 | 436.3 | Ex. 17 |
| 7011 | 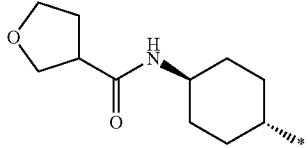 [SMILES: *[C@H]1CC[C@H](NC(=O)C2CCOC2)CC1] | H | 1.72 | 394.2 | Ex. 15 |
| 7012 | 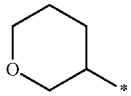 | H | 1.77 | 480.5 | 13i2 & Ex. 14 |
| 7013 | 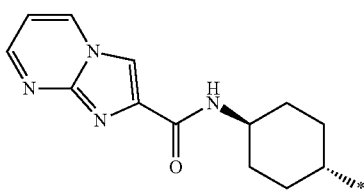 [SMILES: *[C@H]1CC[C@H](NC(=O)c2cn3cccnc3n2)CC1] | H | 1.85 | 369.3 | Ex. 15 |
| 7014 | 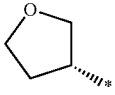 | H | 2.56 | 527.5 | 13i2 & Ex. 14 |
| 7015 | 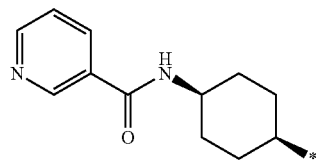 [SMILES: *[C@H]1CC[C@@H](NC(=O)c2cccnc2)CC1] | H | 1.79 | 355.3 | Ex. 15 |
| 7016 | 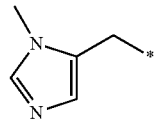 [SMILES: *Cc1cncn1C] | H | 2.56 | 487.5 | 13k2 & Ex. 14 |
| 7017 |  | H | 1.48 | 379.3 | Ex. 15 |

TABLE 7-continued

| Cmpd # | R⁴ | R³ | t_R (min) | (M + H)⁺ | Synthesis Method |
|---|---|---|---|---|---|
| 7018 | 1H-1,2,4-triazol-3-yl-C(=O)-NH-cyclohexyl-* | H | 2.48 | 477.5 | 13k2 & Ex. 14 |
| 7019 | cyclopropyl-CH2-NH-cyclohexyl-* | H | 2.22 | 436.5 | Ex. 42 |
| 7020 | pyridazin-4-yl-C(=O)-NH-cyclohexyl-* | H | 2.53 | 488.4 | 13i2 & Ex. 14 |
| 7021 | imidazo[1,2-a]pyrimidin-2-yl-C(=O)-NH-cyclohexyl-* | H | 2.6 | 527.5 | 13k2 & Ex. 14 |
| 7022 | 1-(methylsulfonyl)pyrrolidin-2-yl-CH2-* | H | 1.66 | 446.4 | 13l2 & Ex. 19 |
| 7023 | 1-(6-methylpyridine-3-carbonyl)pyrrolidin-2-yl-CH2-* | H | 1.72 | 487.4 | 13l2 & Ex. 14 |
| 7024 | 1H-1,2,4-triazol-1-yl-(CH2)3-* | H | 1.72 | 394.2 | Ex. 15 |

TABLE 7-continued
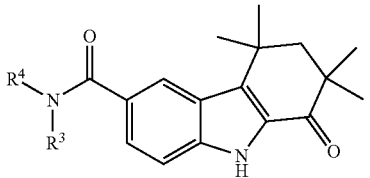
| Cmpd # | R⁴ | R³ | t_R (min) | (M + H)⁺ | Synthesis Method |
|---|---|---|---|---|---|
| 7025 | 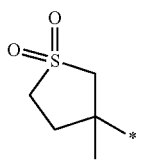 | H | 1.76 | 417.1 | Ex. 15 |
| 7026 | 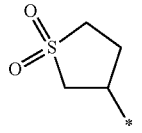 | H | 1.71 | 403.1 | Ex. 15 |
| 7027 | 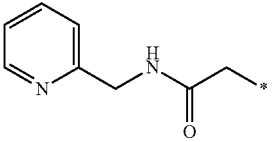 [SMILES: *CC(=O)NCc1ccccn1] | H | 1.7 | 433.3 | Ex. 17 |
| 7028 | 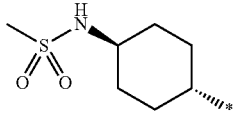 [SMILES: *[C@H]1CC[C@H](NS(C)(=O)=O)CC1] | H | 2.44 | 460.4 | 13i2 & Ex. 19 |
| 7029 | 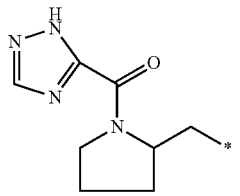 [SMILES: *CC1CCCN1C(=O)c1ncn[nH]1] | H | 1.64 | 463.4 | 13l2 & Ex. 14 |
| 7030 | 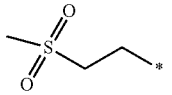 | H | 1.67 | 391.1 | Ex. 15 |
| 7031 | 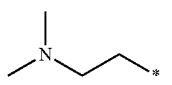 [SMILES: *CCN(C)C] | H | 1.46 | 356.2 | Ex. 15 |
| 7032 | 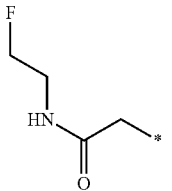 [SMILES: *CC(=O)NCCF] | H | 1.67 | 388.3 | Ex. 17 |

TABLE 7-continued

| Cmpd # | R⁴ | R³ | $t_R$ (min) | (M + H)⁺ | Synthesis Method |
|---|---|---|---|---|---|
| 7033 | pyrazine-carboxamide-ethyl | H | 1.82 | 448.3 | 13m2 & Ex. 14 |
| 7034 | dimethylsulfamoyl-ethyl | H | 1.76 | 420.3 | Ex. 15 |
| 7035 | nicotinamide-ethyl | H | 1.74 | 433.4 | 13m2 & Ex. 14 |
| 7036 | methylsulfonamido-ethyl | H | 1.65 | 406.3 | 13m2 & Ex. 19 |
| 7037 | 6-acetamido-nicotinamide-ethyl | H | 1.76 | 490.3 | 13m2 & Ex. 14 |
| 7038 | H | H | 1.66 | 285.2 | Ex. 56 |
| 7039 | isopropylsulfonyl-ethyl | H | 1.78 | 419.4 | Ex. 15 |
| 7040 | pyrazolo[1,5-a]pyrimidine-2-carboxamide-ethyl | H | 1.75 | 473.3 | 13m2 & Ex. 14 |
| 7041 | pyrimidine-4-carboxamide-ethyl | H | 1.75 | 434.3 | 13m2 & Ex 14 |

TABLE 7-continued
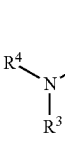
| Cmpd # | R⁴ | R³ | $t_R$ (min) | (M + H)⁺ | Synthesis Method |
|---|---|---|---|---|---|
| 7042 | 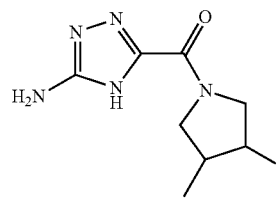 | H | 1.73 | 478.4 | 13c2 & Ex. 14 |
| 7043 | 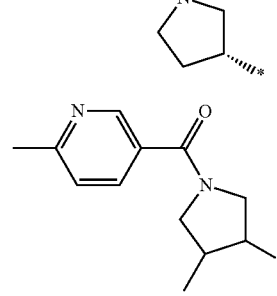 | H | 1.73 | 459.1 | 13d2 & Ex. 14 |
| 7044 | 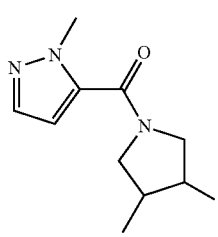 | H | 1.86 | 487.5 | 13c2 & Ex. 14 |
| 7045 | 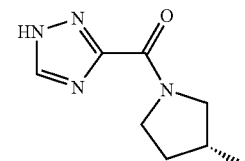 | H | 1.85 | 476.4 | 13c2 & Ex. 14 |
| 7046 | 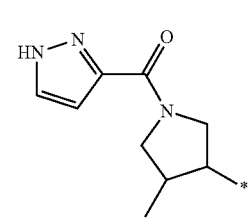 [SMILES: *C1CN(C(=O)c2cc[nH]n2)CC1C] | H | 1.7 | 449.3 | 13d2 & Ex. 14 |
| 7047 | 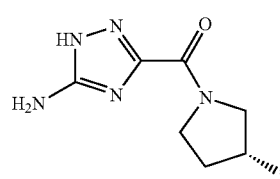 | H | 1.8 | 462.4 | 13c2 & Ex. 14 |
| 7048 |  | H | 1.67 | 464.3 | 13d2 & Ex. 14 |

TABLE 7-continued

| Cmpd # | R⁴ | R³ | t_R (min) | (M + H)⁺ | Synthesis Method |
|---|---|---|---|---|---|
| 7049 | *N,N-dimethyl-3-aminotetrahydrothiophene-3-methyl* | H | 1.57 | 428.3 | Ex. 15 |
| 7050 | *pyrazin-2-yl* | H | 1.92 | 363.3 | Ex. 53 |
| 7051 | *3-methyl-1H-1,2,4-triazol-5-yl* | H | 1.98 | 366.4 | Ex. 53 |
| 7052 | *1-ethyl-1H-pyrazol-5-yl* | H | 1.85 | 379.4 | Ex. 53 |
| 7053 | *(1,1-dioxidotetrahydrothiophen-3-yl)methyl* | H | 1.68 | 417.1 | Ex. 15 |
| 7054 | *(6-methylpyridin-3-yl)carbonyl-3,3-dimethylpyrrolidin-yl* | H | 2.53 | 487.4 | 13n2 & Ex. 14 |
| 7055 | *pyrazin-2-ylcarbonyl-3,3-dimethylpyrrolidin-yl* | H | 2.51 | 474.3 | 13n2 & Ex. 14 |
| 7056 | *(1H-1,2,4-triazol-5-yl)carbonyl-3,3-dimethylpyrrolidin-yl* | H | 2.39 | 463.3 | 13n2 & Ex. 14 |
| 7057 | *pyridin-3-ylcarbonyl-azepan-yl* | H | 2.46 | 487.2 | 13o2 & Ex. 14 |

TABLE 7-continued
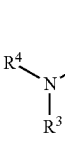
| Cmpd # | R⁴ | R³ | t_R (min) | (M + H)⁺ | Synthesis Method |
|---|---|---|---|---|---|
| 7058 | 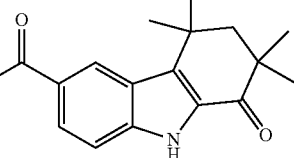 | H | 2.55 | 501.3 | 13o2 & Ex. 14 |
| 7059 | 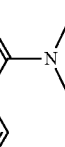 | H | 2.46 | 488.2 | 13o2 & Ex. 14 |
| 7060 | 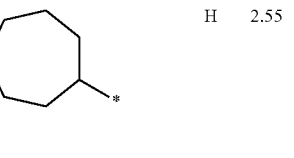 | H | 2.37 | 477.2 | 13o2 & Ex. 14 |
TABLE 8
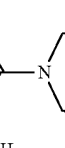
| Cmpd # | Rᵃ | t_R (min) | (M + H)⁺ | Synthesis Method |
|---|---|---|---|---|
| 8001 | 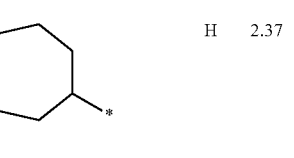 | 3.5 | 387 | Ex. 15 |
| 8002 | 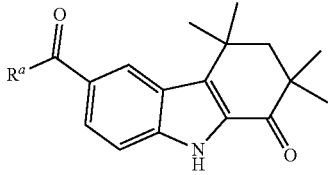 | 1.8 | 388.2 | Ex. 15 |
TABLE 9
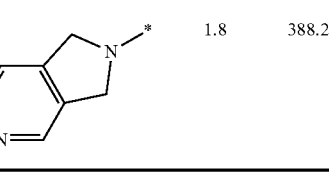
| Cmpd # | R⁴ | X¹ | X² | t_R (min) | (M + H)⁺ | Synthesis Method |
|---|---|---|---|---|---|---|
| 9001 | 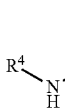 | N | CH | 1.7 | 450.4 | Ex. 30 |
| 9002 | 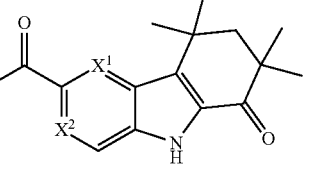 | N | CH | 1.0 | 474.3 | Ex. 30 |

TABLE 9-continued

[Structure: R⁴-NH-C(=O) attached to a bicyclic pyrido-indole system with X¹, X² positions, gem-dimethyl groups and ketone]

| Cmpd # | R⁴ | X¹ | X² | $t_R$ (min) | (M + H)⁺ | Synthesis Method |
|---|---|---|---|---|---|---|
| 9003 | 5-methyl-1H-1,2,4-triazol-3-yl-ethyl | N | CH | 1.0 | 395.3 | Ex. 27 |
| 9004 | pyridin-2-ylmethyl | CH | N | 0.91 | 377.1 | Ex. 28 |
| 9005 | 1,1-dioxotetrahydrothiophen-3-yl | N | CH | 1.3 | 404.3 | Ex. 27 |
| 9006 | pyridin-2-ylmethyl | N | CH | 1.0 | 377.3 | Ex. 27 |
| 9007 | pyrazin-2-ylmethyl | N | CH | 1.3 | 378.3 | Ex. 27 |
| 9008 | 5-methylpyrazin-2-ylmethyl | N | CH | 1.3 | 392.3 | Ex. 27 |

TABLE 10

| Cmpd # | Structure | $t_R$ (min) | (M + H)⁺ | Synthesis Method |
|---|---|---|---|---|
| 1101 | [pyridin-2-ylmethyl amide of 1,1-dimethyl-3-oxo-cyclopenta-indole-7-carboxamide] | 1.43 | 334 | Ex. 57 |
| 1102 | [7-(5-methylamino-1,3,4-oxadiazol-2-yl)-2,2,4,4-tetramethyl-tetrahydrocarbazol-1-one] | 1.2 | 339.2 | Ex. 44 |
| 1103 | [7-(5-((1,1-dioxotetrahydrothiophen-3-yl)amino)-1,3,4-oxadiazol-2-yl)-2,2,4,4-tetramethyl-tetrahydrocarbazol-1-one] | 1.8 | 443.3 | Ex. 44 |

TABLE 10-continued

| Cmpd # | Structure | $t_R$ (min) | $(M + H)^+$ | Synthesis Method |
|---|---|---|---|---|
| 1104 | 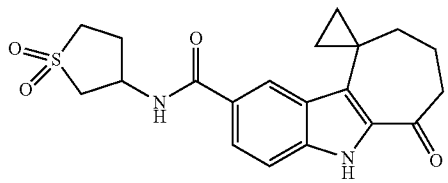 [SMILES: O=C(NC1CCS(=O)(=O)C1)c1ccc2[nH]c3c(c2c1)C1(CCCC3=O)CC1] | 1.49 | 387.3 | Ex. 50 |
| 1105 | 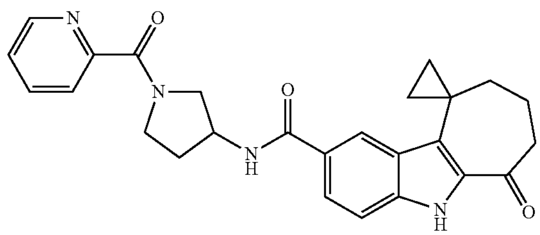 [SMILES: O=C(NC1CCN(C(=O)c2ccccn2)C1)c1ccc2[nH]c3c(c2c1)C1(CCCC3=O)CC1] | 1.62 | 443.3 | Ex. 52 |
| 1106 | 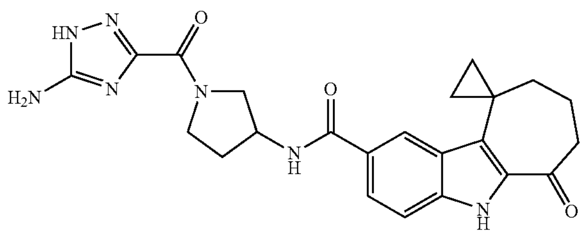 [SMILES: Nc1nc(C(=O)N2CCC(NC(=O)c3ccc4[nH]c5c(c4c3)C3(CCCC5=O)CC3)C2)n[nH]1] | 1.44 | 448.3 | Ex. 52 |
| 1107 | 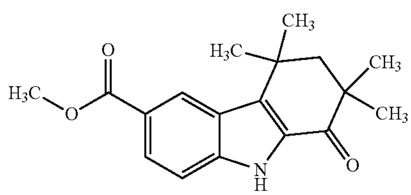 | 3.39 | 300.2 | Ex. 49 |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of Formula (I) or salt thereof:

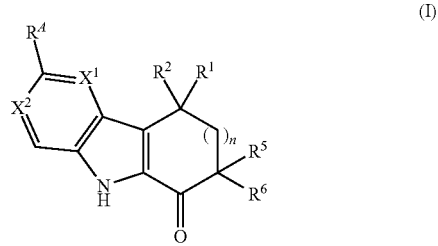

(I)

wherein:

$X^1$ and $X^2$ are each $CR^B$;

$R^B$ is H, $(C_{1-6})$alkyl, $(C_{1-6})$haloalkyl, halo, —O—$(C_{1-6})$alkyl, $NH_2$, $NH(C_{1-6})$alkyl or $N((C_{1-6})$alkyl$)_2$;

$R^1$ and $R^2$ are each independently $(C_{1-6})$alkyl optionally mono- or di-substituted with —O—$(C_{1-6})$alkyl, $NH_2$, $NH(C_{1-6})$alkyl or $N((C_{1-6})$alkyl$)_2$; or $R^1$ and $R^2$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl;

$R^A$ is —C(=O)N($R^3$)($R^4$), —C(=O)O($R^4$), heterocyclyl or heteroaryl, wherein each said heterocyclyl and heteroaryl is optionally substituted 1 to 3 times with $R^{41}$;

$R^3$ is H or $(C_{1-6})$alkyl optionally mono- or di-substituted with —O—$(C_{1-6})$alkyl, $NH_2$, $NH(C_{1-6})$alkyl, $N((C_{1-6})$alkyl$)_2$, —C(=O)—$(C_{1-6})$alkyl, —$SO_2NH_2$, —$SO_2$—$NH(C_{1-6})$alkyl, —$SO_2$—$N((C_{1-6})$alkyl$)_2$, —$SO_2(C_{1-6})$alkyl, —C(=O)—$NH_2$, —C(=O)—$NH(C_{1-6})$alkyl or —C(=O)—$N((C_{1-6})$alkyl$)_2$;

$R^4$ is H, $(C_{1-6})$alkyl, $(C_{3-7})$cycloalkyl, —$(C_{1-6})$alkyl-aryl, —$(C_{1-6})$alkyl-heterocyclyl, —$(C_{1-6})$alkyl-heteroaryl, aryl, heterocyclyl or heteroaryl, wherein each said alkyl, cycloalkyl, aryl or heterocyclyl, either alone or in combination with another radical, is optionally substituted 1 to 3 times with $R^{41}$, and each heteroaryl is mono-substituted with —C(=O)—$R^{42}$; or $R^3$ and $R^4$, together with the N atom to which they are attached, are linked to form a heterocyclyl or heteroaryl, wherein said heterocyclyl and heteroaryl are optionally substituted 1 to 3 times with $R^{41}$;

$R^{41}$ is each independently selected from the group consisting of halo, oxo, cyano, nitro, $R^{42}$, —C(=O)—$R^{42}$, —C(=O)O$R^{42}$, —O$R^{42}$, —S$R^{42}$, —SO$R^{42}$, —SO$_2R^{42}$, —N($R^{43}$)$R^{42}$, —C(=O)—N($R^{43}$)$R^{42}$, —N($R^{43}$)—C(=O)$R^{42}$, —O—C(=O)—N($R^3$)$R^{42}$ and —SO$_2$—N($R^{43}$)$R^{42}$;

$R^{42}$ is each independently selected from the group consisting of H, $(C_{1-6})$alkyl, $(C_{3-7})$cycloalkyl, —$(C_{1-6})$alkyl-aryl, —$(C_{1-6})$alkyl-heterocyclyl, —$(C_{1-6})$alkyl-heteroaryl, aryl, heterocyclyl and heteroaryl, wherein each said alkyl, cycloalkyl, aryl, heterocyclyl and heteroaryl, either alone or in combination with another radical, is optionally substituted with 1 to 3 substituents each independently selected from the group consisting of:

halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —SO$_2$NH$_2$, —SO$_2$—NH$(C_{1-6})$alkyl, —SO$_2$—N$((C_{1-6})$alkyl)$_2$, —SO$_2(C_{1-6})$alkyl, —C(=O)—NH$_2$, —C(=O)—NH$(C_{1-6})$alkyl, —C(=O)—N$((C_{1-6})$alkyl)$_2$, —NH$_2$, —NH$(C_{1-6})$alkyl, —N$((C_{1-6})$alkyl)$_2$, —NH—C(=O)$(C_{1-6})$alkyl and $(C_{1-6})$alkyl optionally mono- or di-substituted with OH or —O—$(C_{1-6})$alkyl;

$R^{43}$ is H or $(C_{1-6})$alkyl;

$R^5$ and $R^6$ are each independently H or $(C_{1-6})$alkyl optionally mono- or di-substituted with —O—$(C_{1-6})$alkyl, NH$_2$, NH$(C_{1-6})$alkyl or N$((C_{1-6})$alkyl)$_2$; or $R^5$ and $R^6$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl; and n is 1.

2. The compound according to claim 1, or a pharmaceutically acceptable salt thereof, wherein $X^1$ and $X^2$ are each $CR^B$;

$R^B$ is H, $(C_{1-6})$alkyl, $(C_{1-6})$haloalkyl, halo, —O—$(C_{1-6})$alkyl, NH$_2$, NH$(C_{1-6})$alkyl or N$((C_{1-6})$alkyl)$_2$;

$R^1$ and $R^2$ are each independently $(C_{1-6})$alkyl optionally mono- or di-substituted with —O—$(C_{1-6})$alkyl, NH$_2$, NH$(C_{1-6})$alkyl or N$((C_{1-6})$alkyl)$_2$; or $R^1$ and $R^2$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl;

$R^A$ is —C(=O)N($R^3$)($R^4$);

$R^3$ is H or $(C_{1-6})$alkyl optionally mono- or di-substituted with —O—$(C_{1-6})$alkyl, NH$_2$, NH$(C_{1-6})$alkyl, N$((C_{1-6})$alkyl)$_2$, —C(=O)—$(C_{1-6})$alkyl, —SO$_2$NH$_2$, —SO$_2$—NH$(C_{1-6})$alkyl, —SO$_2$—N$((C_{1-6})$alkyl)$_2$, —SO$_2(C_{1-6})$alkyl, —C(=O)—NH$_2$, —C(=O)—NH$(C_{1-6})$alkyl or —C(=O)—N$((C_{1-6})$alkyl)$_2$;

$R^4$ is $(C_{3-7})$cycloalkyl, aryl, heterocyclyl or heteroaryl, wherein each said cycloalkyl, aryl, heterocyclyl and heteroaryl, either alone or in combination with another radical, is mono-substituted with —C(=O)—$R^{42}$;

$R^{42}$ is each independently selected from the group consisting of $(C_{1-6})$alkyl, $(C_{3-7})$cycloalkyl, —$(C_{1-6})$alkyl-aryl, —$(C_{1-6})$alkyl-heterocyclyl, —$(C_{1-6})$alkyl-heteroaryl, aryl and heteroaryl, wherein each said alkyl, cycloalkyl, aryl, heterocyclyl and heteroaryl, either alone or in combination with another radical, is optionally substituted with 1 to 3 substituents each independently selected from the group consisting of:

halo, cyano, OH, —COOH, —O—$(C_{1-6})$alkyl, $(C_{3-7})$cycloalkyl, $(C_{1-6})$haloalkyl, —C(=O)—$(C_{1-6})$alkyl, —SO$_2$NH$_2$, —SO$_2$—NH$(C_{1-6})$alkyl, —SO$_2$—N$((C_{1-6})$alkyl)$_2$, —SO$_2(C_{1-6})$alkyl, —C(=O)—NH$_2$, —C(=O)—NH$(C_{1-6})$alkyl, —C(=O)—N$((C_{1-6})$alkyl)$_2$, —NH$_2$, —NH$(C_{1-6})$alkyl, —N$((C_{1-6})$alkyl)$_2$, —NH—C(=O)$(C_{1-6})$alkyl and $(C_{1-6})$alkyl optionally mono- or di-substituted with OH or —O—$(C_{1-6})$alkyl;

$R^5$ and $R^6$ are each independently H or $(C_{1-6})$alkyl optionally mono- or di-substituted with —O—$(C_{1-6})$alkyl, NH$_2$, NH$(C_{1-6})$alkyl or N$((C_{1-6})$alkyl)$_2$; or $R^5$ and $R^6$, together with the carbon to which they are attached, are linked to form a $(C_{3-7})$cycloalkyl group or a 3- to 7-membered heterocyclyl, said cycloalkyl and heterocyclyl being optionally mono- or di-substituted with —$(C_{1-6})$alkyl; and n is 1.

3. The compound according to claim 1, or a pharmaceutically acceptable salt thereof, wherein $X^1$ and $X^2$ are CH.

4. The compound according to claim 1, or a pharmaceutically acceptable salt thereof, wherein $R^1$ and $R^2$ are each independently $(C_{1-3})$alkyl optionally mono-substituted with —O—$(C_{1-3})$alkyl, NH$_2$, NH$(C_{1-3})$alkyl or N$((C_{1-3})$alkyl)$_2$; or $R^1$ and $R^2$ and the carbon to which they are attached are linked to form a $(C_{3-7})$cycloalkyl group.

5. The compound according to claim 4 or a pharmaceutically acceptable salt thereof, wherein $R^1$ and $R^2$ are each independently $(C_{1-3})$alkyl optionally mono-substituted with —O—$(C_{1-3})$alkyl; or $R^1$ and $R^2$ and the carbon to which they are attached are linked to form a $(C_{3-4})$cycloalkyl group.

6. The compound according to claim 1, or a pharmaceutically acceptable salt thereof, wherein $R^A$ is —C(=O)N($R^3$)($R^4$).

7. The compound according to claim 1, or a pharmaceutically acceptable salt thereof, wherein $R^3$ is H.

8. The compound according to claim 1, or a pharmaceutically acceptable salt thereof, wherein $R^4$ is heterocyclyl mono-substituted with —C(=O)—$R^{42}$;

$R^{42}$ is each independently selected from the group consisting of $(C_{5-7})$cycloalkyl, —$(C_{1-4})$alkyl-heterocyclyl, —$(C_{1-4})$alkyl-heteroaryl and heteroaryl, wherein each said alkyl, cycloalkyl, heterocyclyl and heteroaryl, either alone or in combination with another radical, is optionally mono- or di-substituted with substitutents each independently selected from the group consisting of:

halo, OH, —O—$(C_{1-6})$alkyl, —SO$_2$NH$_2$, —SO$_2$—NH$(C_{1-6})$alkyl, —SO$_2$—N$((C_{1-6})$alkyl)$_2$, —SO$_2(C_{1-6})$alkyl, —NH$_2$, —NH$(C_{1-6})$alkyl, —N$((C_{1-6})$alkyl)$_2$, —NH—C(=O)$(C_{1-6})$alkyl and $(C_{1-6})$alkyl.

9. The compound according to claim 8, or a pharmaceutically acceptable salt thereof, wherein $R^4$ is heterocyclyl mono-substituted with —C(=O)-heteroaryl, wherein said heteroaryl is optionally mono- or di-substituted with substitutents each independently selected from the group consisting of:

halo, OH, —O—$(C_{1-6})$alkyl, —SO$_2$NH$_2$, —SO$_2$—NH$(C_{1-6})$alkyl, —SO$_2$—N$((C_{1-6})$alkyl)$_2$, —SO$_2(C_{1-6})$alkyl, —NH$_2$, —NH$(C_{1-6})$alkyl, —N$((C_{1-6})$alkyl)$_2$, —NH—C(=O)$(C_{1-6})$alkyl and $(C_{1-6})$alkyl.

10. The compound according to claim 1, or a pharmaceutically acceptable salt thereof, wherein $R^5$ and $R^6$ are each independently $(C_{1-3})$alkyl optionally mono-substituted with —O—$(C_{1-3})$alkyl; or $R^5$ and $R^6$ and the carbon to which they are attached are linked to form a $(C_{3-4})$cycloalkyl group or a 4- to 6-membered heterocyclyl.

11. A method for the treatment of hepatitis C viral infection in a human being, comprising administering to said human being a therapeutically effective amount of a compound according to claim 1 or a pharmaceutically acceptable salt thereof.

12. A pharmaceutical composition comprising a compound according to claim 1, or a pharmaceutically acceptable salt thereof, and a pharmaceutically acceptable carrier.

13. The pharmaceutical composition according to claim 12 further comprising a therapeutically effective amount of at least one other antiviral agent.

* * * * *